(12) United States Patent
Doronina et al.

(10) Patent No.: US 8,288,352 B2
(45) Date of Patent: Oct. 16, 2012

(54) AURISTATINS HAVING AN AMINOBENZOIC ACID UNIT AT THE N TERMINUS

(75) Inventors: Svetlana O. Doronina, Snohomish, WA (US); Brian A. Mendelsohn, Bellevue, WA (US)

(73) Assignee: Seattle Genetics, Inc., Bothell, WA (US)

( * ) Notice: Subject to any disclaimer, the term of this patent is extended or adjusted under 35 U.S.C. 154(b) by 1219 days.

(21) Appl. No.: 11/667,437

(22) PCT Filed: Nov. 14, 2005

(86) PCT No.: PCT/US2005/041514
§ 371 (c)(1),
(2), (4) Date: Apr. 4, 2008

(87) PCT Pub. No.: WO2006/132670
PCT Pub. Date: Dec. 14, 2006

(65) Prior Publication Data
US 2008/0300192 A1     Dec. 4, 2008

Related U.S. Application Data

(60) Provisional application No. 60/627,207, filed on Nov. 12, 2004.

(51) Int. Cl.
*A61K 38/08* (2006.01)
*A61K 39/00* (2006.01)

(52) U.S. Cl. .................... 514/21.8; 530/330; 424/185.1; 424/193.1

(58) Field of Classification Search ................. None
See application file for complete search history.

(56) References Cited

U.S. PATENT DOCUMENTS

| | | | |
|---|---|---|---|
| 4,753,894 A | 6/1988 | Frankel et al. |
| 4,943,628 A | 7/1990 | Rosen et al. |
| 4,978,744 A | 12/1990 | Pettit et al. |
| 5,169,774 A | 12/1992 | Frankel et al. |
| 5,286,637 A | 2/1994 | Veronese et al. |
| 5,410,024 A | 4/1995 | Pettit et al. |
| 5,629,197 A | 5/1997 | Ring et al. |
| 5,635,483 A | 6/1997 | Pettit et al. |
| 5,654,399 A | 8/1997 | Sakakibara et al. |
| 5,767,237 A | 6/1998 | Sakakibara et al. |
| 5,780,588 A | 7/1998 | Pettit et al. |
| 5,821,337 A | 10/1998 | Carter et al. |
| 5,840,699 A | 11/1998 | Sakakibara et al. |
| 6,004,934 A | 12/1999 | Sakakibara et al. |
| 6,048,720 A | 4/2000 | Dalborg et al. |
| 6,054,297 A | 4/2000 | Carter et al. |
| 6,054,561 A | 4/2000 | Ring |
| 6,124,431 A | 9/2000 | Sakakibara et al. |
| 6,214,345 B1 | 4/2001 | Firestone et al. |
| 6,407,213 B1 | 6/2002 | Carter et al. |
| 6,569,834 B1 | 5/2003 | Pettit et al. |
| 6,620,911 B1 | 9/2003 | Petit et al. |
| 6,639,055 B1 | 10/2003 | Carter et al. |
| 6,884,869 B2 | 4/2005 | Senter et al. |
| 7,498,298 B2 | 3/2009 | Doronina et al. |
| 7,659,241 B2 | 2/2010 | Senter et al. |
| 7,745,394 B2 | 6/2010 | Doronina et al. |
| 7,829,531 B2 | 11/2010 | Senter et al. |
| 7,851,437 B2 | 12/2010 | Senter et al. |
| 7,964,566 B2 | 6/2011 | Doronina et al. |
| 7,964,567 B2 | 6/2011 | Doronina et al. |
| 7,968,687 B2 | 6/2011 | McDonagh et al. |
| 7,994,135 B2 | 8/2011 | Doronina et al. |
| 2002/0001587 A1 | 1/2002 | Erickson et al. |
| 2003/0083263 A1* | 5/2003 | Doronina et al. ............ 514/17 |
| 2003/0096743 A1 | 5/2003 | Senter et al. |
| 2003/0130189 A1 | 7/2003 | Senter et al. |
| 2004/0018194 A1 | 1/2004 | Francisco et al. |
| 2004/0157782 A1 | 8/2004 | Doronina et al. |
| 2004/0235068 A1 | 11/2004 | Levinson |
| 2005/0009751 A1 | 1/2005 | Senter et al. |
| 2005/0106644 A1 | 5/2005 | Cairns et al. |
| 2005/0107595 A1 | 5/2005 | Cairns et al. |
| 2005/0113308 A1 | 5/2005 | Senter et al. |
| 2005/0232929 A1 | 10/2005 | Kadkhodayan et al. |
| 2005/0238649 A1 | 10/2005 | Doronina et al. |
| 2005/0238650 A1 | 10/2005 | Crowley et al. |
| 2005/0256030 A1 | 11/2005 | Feng |
| 2005/0272665 A1 | 12/2005 | Schmid et al. |
| 2006/0073152 A1 | 4/2006 | Dennis |
| 2006/0074008 A1 | 4/2006 | Senter et al. |
| 2006/0128970 A1 | 6/2006 | Bliss et al. |
| 2006/0182751 A1 | 8/2006 | Gazzard et al. |
| 2006/0233794 A1 | 10/2006 | Law et al. |
| 2007/0092520 A1 | 4/2007 | Dennis et al. |
| 2007/0134243 A1 | 6/2007 | Gazzard et al. |
| 2007/0212356 A1 | 9/2007 | Chen et al. |
| 2009/0018086 A1 | 1/2009 | Doronina et al. |
| 2009/0111757 A1 | 4/2009 | Lin et al. |
| 2011/0312088 A1 | 12/2011 | McDonagh et al. |

FOREIGN PATENT DOCUMENTS

| | | |
|---|---|---|
| CA | 2114156 C | 7/1994 |
| JP | 06-234790 A | 8/1994 |
| JP | 09-77791 A | 3/1997 |
| WO | WO 99/35164 A1 | 7/1999 |
| WO | WO 01/18032 A2 | 3/2001 |
| WO | WO 01/18032 A3 | 3/2001 |
| WO | WO 02/088172 A2 | 11/2002 |
| WO | WO 02/088172 A3 | 11/2002 |
| WO | WO 03/008378 A1 | 1/2003 |
| WO | WO 03/034903 A2 | 5/2003 |

(Continued)

OTHER PUBLICATIONS

Vippagunta, et al. Adv. Drug Delivery Rev. (2001) 48, pp. 3-26.*
Afar, D.E.H. et al., "Preclinical Validation of Anti-TMEFF2-Auristatin E-Conjugated Antibodies in the Treatment of Prostate Cancer," *Molecular Cancer Therapeutics*, Aug. 2004, vol. 3, No. 8, pp. 921-932.

(Continued)

*Primary Examiner* — Karlheinz R Skowronek
*Assistant Examiner* — Satyanarayana R Gudibande
(74) *Attorney, Agent, or Firm* — Kilpatrick Townsend & Stockton LLP

(57) ABSTRACT

Auristatin-type peptides are disclosed which are highly cytotoxic, synthetically accessible, and can be conjugated to antibodies and other ligands.

28 Claims, 2 Drawing Sheets

FOREIGN PATENT DOCUMENTS

| | | |
|---|---|---|
| WO | WO 03/034903 A3 | 5/2003 |
| WO | WO 03/043583 A2 | 5/2003 |
| WO | WO 03/043583 A3 | 5/2003 |
| WO | WO 2004/032828 A2 | 4/2004 |
| WO | WO 2004/032828 A3 | 4/2004 |
| WO | WO 2004/073656 A2 | 9/2004 |
| WO | WO 2006/034488 A2 | 3/2006 |
| WO | WO 2006/034488 A3 | 3/2006 |
| WO | WO 2006/083936 A2 | 8/2006 |
| WO | WO 2006/083936 A3 | 8/2006 |
| WO | WO 2007/001851 A2 | 1/2007 |
| WO | WO 2007/001851 A3 | 1/2007 |
| WO | WO 2007/008603 A1 | 1/2007 |
| WO | WO 2007/008848 A2 | 1/2007 |
| WO | WO 2007/109567 A1 | 9/2007 |

OTHER PUBLICATIONS

Alley, S. et al., "Controlling the Location of Drug Attachment in Antibody-Drug Conjugates," *Proceedings of the AACR*, Mar. 2004, vol. 45, Abstract No. 627, 1 page.

Bhaskar, V. et al., "E-Selectin Up-Regulation Allows for Targeted Drug Delivery in Prostate Cancer," *Cancer Research*, Oct. 1, 2003, vol. 63, pp. 6387-6394.

Carter, P., "Improving the Efficacy of Antibody-Based Cancer Therapies," *Nature Reviews*, Nov. 2001, vol. 1, pp. 118-129.

Dillman, "Monoclonal Antibodies for Treating Cancer," *Annals of Internal Medicine*, Oct. 1, 1989, vol. 111, No. 7, pp. 592-603.

Doronina, S.O. et al., "Development of Potent Monoclonal Antibody Auristatin Conjugates for Cancer Therapy," *Nature Biotechnology*, Jul. 2003, vol. 21, No. 7, pp. 778-784, Erratum, *Nature Biotechnology*, 2003, vol. 21, No. 8, p. 941.

Doronina, S. et al., "Immunoconjugates Comprised of Drugs With Impaired Cellular Permeability: A New Approach to Targeted Therapy," SciFinder search result, abstract of paper from 228th ACS National Meeting held in Philadelphia, PA, Aug. 22-26, 2004, 1 page.

Doronina, S.O. et al., "Enhanced Activity of Monomethylauristatin F Through Monoclonal Antibody Delivery: Effects of Linker Technology on Efficacy and Toxicity," *Bioconjugate Chem.*, 2006, vol. 17, No. 1, pp. 114-124.

Emery, S.C. et al., "Humanized Monoclonal Antibodies for Therapeutic Applications," *Exp. Opin. Invest. Drugs*, 1994, vol. 3, No. 3, pp. 241-251.

Francisco, J.A. et al., "cAC10-vcMMAE, an Anti-CD30-monomethyl Auristatin E Conjugate With Potent and Selective Antitumor Activity," *Blood*, Aug. 15, 2003, vol. 102, No. 4, pp. 1458-1465.

Gaertner, H.F. et al., "Site-Specific Attachment of Functionalized Poly (ethylene glycol) to the Amino Terminus of Proteins," *Bioconjugate Chem.*, 1996, vol. 7, No. 1, pp. 38-44.

Genet, J. P., "Recent Studies on Asymmetric Hydrogenation. New Catalysts and Synthetic Applications in Organic Synthesis," *Pure Appl. Chem.*, 2002, vol. 74, No. 1, pp. 77-83.

Hamblett, K.J. et al., "Effect of Drug Loading on the Pharmacology, Pharmacokinetics, and Toxicity of an Anti-CD30 Antibody-Drug Conjugate," *Proceedings of the AACR*, Mar. 2004, vol. 45, Abstract No. 624, 1 page.

Inada, Y. et al., "Modification of Proteins With Polyethylene Glycol Derivatives," *Methods Enzymology*, 1994, vol. 242, pp. 65-90.

International Search Report mailed on Oct. 2, 2006, for PCT Application No. PCT/US04/38392 filed on Nov. 5, 2004, 6 pages.

International Search Report mailed on Nov. 27, 2006, for PCT Application No. PCT/US06/26352, filed on Jul. 7, 2006, 1 page.

International Search Report mailed on May 23, 2007, for PCT Application No. PCT/US05/41514, filed on Nov. 14, 2005, 1 page.

Kline, T. et al., "Novel Antitumor Prodrugs Designed for Activation by Matrix Metalloproteinases-2 and -9," *Molecular Pharmaceutics*, 2004, vol. 1, No. 1, pp. 9-22.

Klussman, K. et al., "Secondary mAb—vcMMAE Conjugates Are Highly Sensitive Reporters of Antibody Internalization via the Lysosome Pathway," *Bioconjugate Chem.*, 2004, vol. 15, No. 4, pp. 765-773.

Law, C-L. et al., "CD70 is Expressed on Renal Cell Carcinoma and is a Potential Target for Tumor Cell Elimination by Antibody-Drug Conjugates," *Proceedings of the AACR*, Mar. 2004, vol. 45, Abstract No. 625, 1 page.

Mao, W. et al., "EphB2 as a Therapeutic Antibody Drug Target for the Treatment of Colorectal Cancer," *Cancer Research*, Feb. 1, 2004, vol. 64, pp. 781-788.

Meyer, D.L. et al., "Recent Advances in Antibody Drug Conjugates for Cancer Therapy," *Annual Reports in Medical Chemistry*, 2003, vol. 38, Chapter 23, pp. 229-237.

Miyazaki, K. et al., "Synthesis and Antitumor Activity of Novel Dolastatin 10 Analogs," *Chem. Pharm. Bull.*, Oct. 1995, vol. 43, No. 10, pp. 1706-1718.

Natsume, T. et al., "Characterization of the Interaction of TZT-1027, a Potent Antitumor Agent, With Tubulin," *Jpn. J. Cancer*, Jul. 2000, vol. 91, pp. 737-747.

Pettit, G.R. et al., "The Absolute Configuration and Synthesis of Natural (−)-Dolastatin 10," *J. Am. Chem. Soc.*, 1989, vol. 111, No. 14, pp. 5463-5465.

Pettit, G.R. et al., "Antineoplastic Agents 337. Synthesis of Dolastatin 10 Structural Modifications," *Anti-Cancer Drug Design*, 1995, vol. 10, pp. 529-544.

Pettit, G.R. et al., "Dolastatins 24. Synthesis of (−)-Dolastatin 10. X-Ray Molecular Structure of N,N-dimethylvalyl-valyl-dolaisoleuine tert-butyl Ester," *J. Chem. Soc. Perkin Trans.1*, 1996, vol. 5, pp. 859-863.

Pettit, G.R. et al., "Antineoplastic Agents 365. Dolastatin 10 SAR Probes," *Anti-Cancer Drug Design*, 1998, vol. 13, No. 4, pp. 243-277.

Pettit, G.R. et al., "A Cobalt-Phosphine Complex Directed Reformatsky Approach to a Stereospecific Synthesis of the Dolastatin 10 Unit Dolaproine (Dap)," *J. Org. Chem.*, 2001, vol. 66, No. 25, pp. 8640-8642.

Pettit, R.K. et al., "Specific Activities of Dolastatin 10 and Peptide Derivatives Against *Cryptococcus neoformans*," *Antimicrobial Agents and Chemotherapy*, 1998, vol. 42, No. 11, pp. 2961-2965.

Press Release, "Seattle Genetics, Inc. (SGEN) to Present Advances in Preclinical Research at American Cancer Research Annual Meeting," Mar. 24, 2004, downloaded from internet on Aug. 31, 2004, located at <http://www.biospace.com/ccis/news_story.cfm?StoryIDS=15536520&full=1>, 2 pages.

Schöffski, P. et al., "Phase I and Pharmacokinetic Study of TZT-1027, a Novel Synthetic Dolastatin 10 Derivative, Administered as a 1-Hour Intravenous Infusion Every 3 Weeks in Patients With Advanced Refractory Cancer," *Annals of Oncology*, 2004, vol. 15, pp. 671-679.

Senter, P. et al., "Immunoconjugates Composed of Drugs With Impaired Cellular Permeability: A New Approach to Targeted Therapy," *Proceedings of the AACR*, Mar. 2004, Abstract No. 623, 2 pages.

Thornber, C.W., "Isoterism and Molecular Modification in Drug Design," *Chem. Soc. Rev.*, 1979, vol. 8, No. 4, pp. 563-580.

Toki, B.E. et al., "Protease-Mediated. Fragmentation of p-Amidobenzyl Ethers: A New Strategy for the Activation of Anticancer Prodrugs," *J. Org. Chem.*, 2002, vol. 67, No. 6, pp. 1866-1872.

Vippagunta, S.R. et al., "Crystalline Solids," *Advanced Drug Delivery Reviews*, 2001, vol. 48, pp. 3-26.

Woyke, T. et al., "In Vitro Activities and Postantifungal Effects of the Potent Dolastatin 10 Derivative Auristatin PHE," *Antimicrobial Agents and Chemotherapy*, Dec. 2001, vol. 45, No. 12, pp. 3580-3584.

Woyke, T. et al., "Effect of Auristatin PHE on Microtube Integrity and Nuclear Localization in *Cryptococcus neoformans*," *Antimicrobial Agents and Chemotherapy*, Dec. 2002, vol. 46, No. 12, pp. 3802-3808.

Written Opinion mailed on Oct. 2, 2006, for PCT Application No. PCT/US04/38392 filed on Nov. 5, 2004, 6 pages.

\* cited by examiner

AURISTATINS HAVING AN AMINOBENZOIC ACID UNIT AT THE N TERMINUS

CONTINUITY

This application claims the benefit of U.S. Provisional Patent Application No. 60/627,207, filed Nov. 12, 2004, the disclosure of which is incorporated by reference herein.

BACKGROUND

The delivery of drugs and other agents to target cells or tissues for the treatment of cancer and other diseases has been the focus of considerable research for many years. Most agents currently administered to a patient parenterally are not targeted, resulting in systemic delivery of the agent to cells and tissues of the body where it is unnecessary, and often undesirable. This may result in adverse drug side effects, and often limits the dose of a drug (e.g., chemotherapeutic (anti-cancer), cytotoxic, enzyme inhibitor agents and antiviral or antimicrobial drugs) that can be administered. Although oral administration of drugs is considered to be a convenient and economical mode of administration, it shares the same concerns of non-specific toxicity to non-target cells once the drug has been absorbed into the systemic circulation. Further complications involve problems with oral bioavailability and residence of drug in the gut leading to additional exposure of gut to the drug and hence risk of gut toxicities.

Accordingly, a major goal has been to develop methods for specifically targeting agents to cells and tissues. The benefits of such treatment include avoiding the general physiological effects of inappropriate delivery of such agents to other cells and tissues, such as uninfected cells. Intracellular targeting may be achieved by methods, compounds and formulations which allow accumulation or retention of agents, i.e. cytotoxic or cytostatic agents, inside cells. The use of antibody-drug conjugates for the local delivery of cytotoxic or cytostatic agents (e.g., drugs to kill or inhibit tumor cells in the treatment of cancer) can allow targeted delivery of the drug moiety to tumors, and intracellular accumulation therein. In contrast, systemic administration of unconjugated drug agents may result in unacceptable levels of toxicity to normal cells as well as the tumor cells sought to be eliminated.

In antibody drug conjugates, the drug can be linked directly to the antibody (e.g., via a cysteine residue) or indirectly via a linker. Internalization of the target antibody following antigen binding carries the drug into the target cell. Once internalized, the drug can be released from the antibody by cleavage in the lysozme or by other cellular mechanism. To facilitate drug release, a cleavable site can be included in the linker. In some conjugates, a portion of a linker may remain attached to the drug after cleavage. To avoid this, a self-immolative spacer has been included in the linker. A self-immolative spacer is a bifunctional chemical moiety which is capable of covalently linking together two spaced chemical moieties into a normally stable tripartate molecule (e.g., an antibody-linker-drug conjugate). Following cleavage, the spacer spontaneously cleaves itself from the remainder of the molecule to release the other of said spaced chemical moieties. (See U.S. Pat. No. 6,214,345.) For example, one self-immolative spacer unit is p-aminobenzylcarbamoyl (PABC).

However, there is a need for an antibody drug conjugate which does not require a self-immolative spacer for efficient drug release from the antibody drug conjugate when linked through an enzymatically cleavable linker. These and other limitations and problems of the past are solved by the present invention. The recitation of any reference in this application is not an admission that the reference is prior art to this application.

BRIEF SUMMARY OF THE INVENTION

The present invention provides Conjugate Compounds of general Formula Ia:

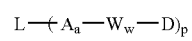

and pharmaceutically acceptable salts and solvates thereof; wherein,

L- is a Ligand unit;

-$A_a$-$W_w$— is a Linker unit (LU), wherein the Linker unit includes:

-A- is a Stretcher unit, a is 0 or 1, each —W— is independently an Amino Acid unit, w is an integer ranging from 0 to 12, p ranges from 1 to about 20; and -D is a Drug unit of the following formula:

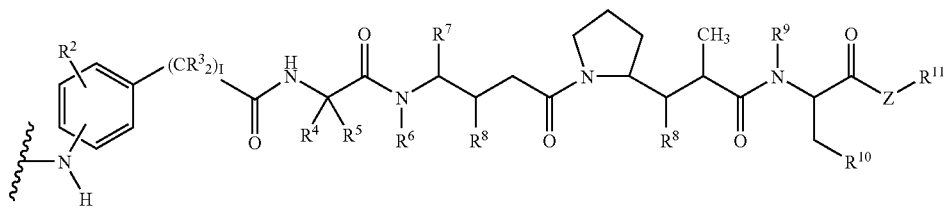

wherein, independently at each location:

$R^2$ is selected from -hydrogen and —$C_1$-$C_8$ alkyl, —O—($C_1$-$C_8$ alkyl), -halogen, —$NO_2$, —COOH, and —C(O)$OR^{11}$;

each $R^3$ is selected independently from -hydrogen and —$C_1$-$C_8$ alkyl;

l is an integer ranging from 0-10;

$R^4$ is selected from -hydrogen, —$C_1$-$C_8$ alkyl, —$C_3$-$C_8$ carbocycle, aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle), and $R^5$ is selected from —H and -methyl; or $R^4$ and $R^5$ jointly have the formula —$(CR^aR^b)_n$—, wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl($C_3$-$C_8$ heterocycle);

each $R^8$ is independently selected from —H, —OH, —$C_1$-$C_8$ alkyl, —$C_3$-$C_8$ carbocycle, —O-alkyl-($C_1$-$C_8$ carbocycle) and —O—($C_1$-$C_8$ alkyl);

$R^9$ is selected from —H and —$C_1$-$C_8$ alkyl;

$R^{10}$ is selected from aryl group or —$C_3$-$C_8$ heterocycle;

Z is —O—, —S—, —NH—, or —$NR^{12}$— where $R^{12}$ is $C_1$-$C_8$ alkyl or aryl; and $R^{11}$ is selected from —H, $C_1$-$C_8$ alkyl, aryl, —$C_3$-$C_8$ heterocycle, —$(CH_2CH_2O)_r$—H, —$(CH_2CH_2O)_r$—$CH_3$, —$(CH_2CH_2O)_r$—$CH_2CH_2C(O)OH$; wherein r is an integer ranging from 1-10.

In some embodiments, the Linker Unit has the general Formula Ib:

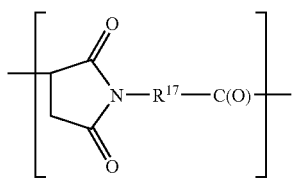

Ib wherein $R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_r$—, and —$(CH_2CH_2O)_r$—$CH_2$—; and r is an integer ranging from 1-100.

In another aspect, Drug Compounds of general Formula I are provided:

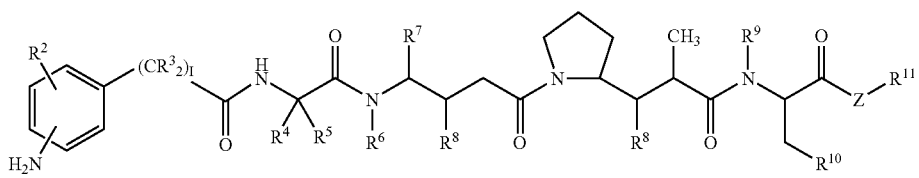

I and pharmaceutically acceptable salts or solvates thereof; wherein, independently at each location:

$R^2$ is selected from -hydrogen and —$C_1$-$C_8$ alkyl, —O—($C_1$-$C_8$ alkyl), -halogen, —$NO_2$, —COOH, and —$C(O)OR^{11}$;

each $R^3$ is selected independently from -hydrogen and —$C_1$-$C_8$ alkyl;

l is an integer ranging from 0-10;

$R^4$ is selected from -hydrogen, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle), and $R^5$ is selected from —H and -methyl; or $R^4$ and $R^5$ jointly have the formula —$(CR^aR^b)_n$— wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl($C_3$-$C_8$ heterocycle);

each $R^8$ is independently selected from —H, —OH, —$C_1$-$C_8$ alkyl, —$C_3$-$C_8$ carbocycle, —O-alkyl-($C_1$-$C_8$ carbocycle) and —O—($C_1$-$C_8$ alkyl);

$R^9$ is selected from —H and —$C_1$-$C_8$ alkyl;

$R^{10}$ is selected from aryl group or —$C_3$-$C_8$ heterocycle;

Z is —O—, —S—, —NH—, —$NR^{12}$— where $R^{12}$ is $C_1$-$C_8$ alkyl or aryl; and $R^{11}$ is selected from —H, $C_1$-$C_8$ alkyl, aryl, —$C_3$-$C_8$ heterocycle, —$(CH_2CH_2O)_r$—H, —$(CH_2CH_2O)_r$—$CH_3$, —$(CH_2CH_2O)_r$—$CH_2CH_2C(O)OH$; where r is an integer ranging from 1-10.

In another aspect, compositions are provided including an effective amount of a Conjugate Compound or Drug Compound and a pharmaceutically acceptable carrier or vehicle.

In yet another aspect, methods for killing or inhibiting the multiplication of a tumor cell or cancer cell are provided. The methods include administering to a patient in need thereof an effective amount of a Conjugate Compound, a Drug Linker Compound or a Drug Compound.

In still another aspect, methods for killing or inhibiting the replication of a cell that expresses an autoimmune antibody are provided. The methods include administering to a patient in need thereof an effective amount of a Conjugate Compound, a Drug-Linker Compound or a Drug Compound.

In still another aspect, methods for treating an infectious disease are provided. The methods include administering to a patient in need thereof an effective amount of a Conjugate Compound, a Drug-Linker Compound or a Drug Compound.

In another aspect, the invention provides intracellular metabolites of a Conjugate Compound, such as a Drug Compound, a Drug-Linker Compound or a Drug-Linker fragment.

The invention is further understood by reference to the following detailed description of the exemplary embodiments, taken in conjunction with the accompanying drawings, figures, and schemes. The discussion below is descriptive, illustrative and exemplary and is not to be taken as limiting the scope defined by any appended claims.

DEFINITIONS AND ABBREVIATIONS

Figure 1:
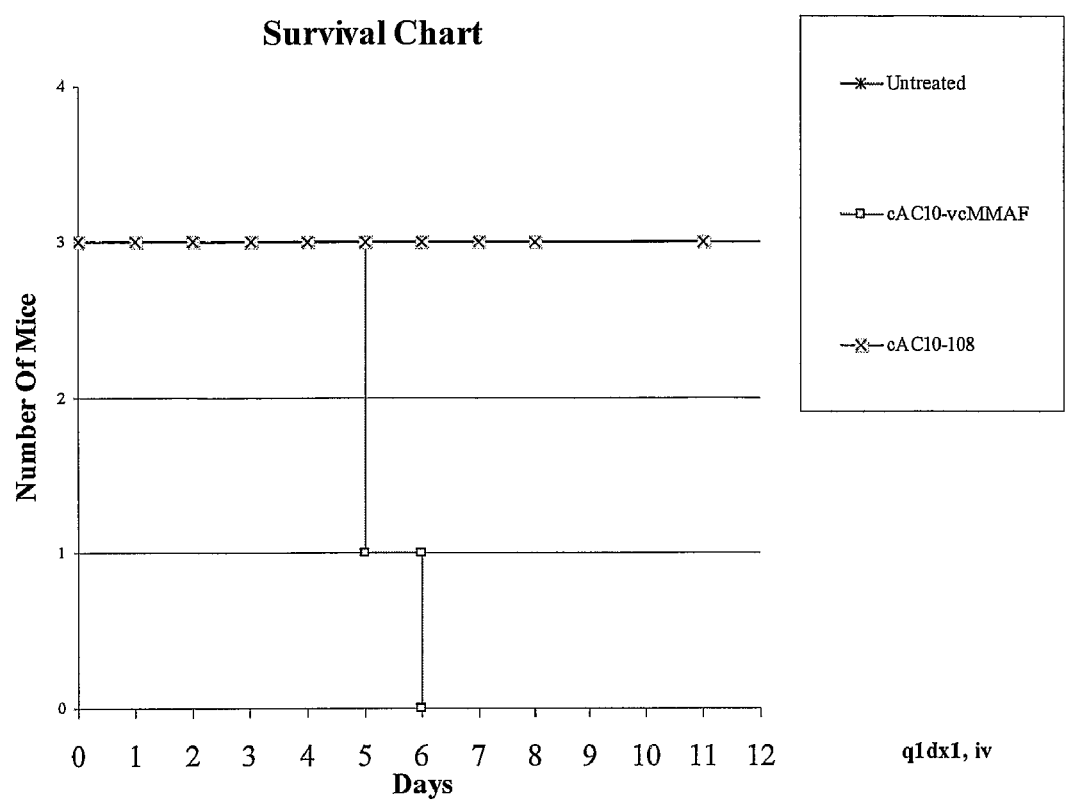
FIG. 1 shows toxicity of cAC10-108 conjugate in mice.

Unless stated otherwise, the following terms and phrases as used herein are intended to have the following meanings. When trade names are used herein, applicants intend to independently include the trade name product formulation, the generic drug, and the active pharmaceutical ingredient(s) of the trade name product.

The term "antibody" herein is used in the broadest sense and specifically covers intact monoclonal antibodies, polyclonal antibodies, multispecific antibodies (e.g., bispecific antibodies) formed from at least two intact antibodies, and antibody fragments, so long as they exhibit the desired biological activity. The term "antibody" refers to a full-length immunoglobulin molecule or a functionally active portion of a full-length immunoglobulin molecule, i.e., a molecule that contains an antigen binding site that immunospecifically binds an antigen of a target of interest or part thereof. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect the immunoglobulin is of human, murine, or rabbit origin. In another aspect, the antibodies are polyclonal, monoclonal, multi-specific (e.g., bispecific), human, humanized or chimeric antibodies, linear antibodies, single chain antibodies, diabodies, maxibodies, minibodies, Fv, Fab fragments, F(ab') fragments, F(ab')$_2$ fragments, fragments produced by a Fab expression library, anti-idiotypic (anti-Id) antibodies, CDR's, and epitope-binding fragments of any of the above which immunospecifically bind to a target antigen.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies (see, e.g., U.S. Pat. No. 4,816,567; and Morrison et al., 1984, Proc. Natl. Acad. Sci. USA 81:6851-6855). Monoclonal antibodies also include humanized antibodies may contain a completely human constant region and a CDRs from a nonhuman source.

An "intact" antibody is one which comprises an antigen-binding variable region as well as a light chain constant domain (CL) and heavy chain constant domains, $C_H1$, $C_H2$ and $C_H3$. The constant domains may be native sequence constant domains (e.g., human native sequence constant domains) or amino acid sequence variant thereof.

An intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity (CDC_; Fc receptor binding; antibody-dependent cell-mediated cytotoxicity (ADCC); phagocytosis; down regulation of cell surface receptors (e.g., B cell receptor; BCR), etc. In some embodiments, the antibody lacks effector function.

"Antibody fragments" comprise a portion of an intact antibody, preferably comprising the antigen-binding or variable region thereof. Examples of antibody fragments include Fab, Fab', F(ab')$_2$, and Fv fragments; diabodies; linear antibodies; single-chain antibody molecules; maxibodies; minibodies; and multispecific antibodies formed from antibody fragment(s).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" an antigen of interest is one capable of binding that antigen with sufficient affinity such that the antibody is useful in targeting a cell expressing the antigen.

A "native sequence" polypeptide is one which has the same amino acid sequence as a polypeptide derived from nature. Such native sequence polypeptides can be isolated from nature or can be produced by recombinant or synthetic means. Thus, a native sequence polypeptide can have the amino acid sequence of naturally-occurring human polypeptide, murine polypeptide, or polypeptide from any other mammalian species.

The term "amino acid sequence variant" refers to polypeptides having amino acid sequences that differ to some extent from a native sequence polypeptide. Ordinarily, amino acid sequence variants will possess at least about 70% homology with at least one receptor binding domain of a native ligand, or with at least one ligand binding domain of a native receptor and preferably, they will be at least about 80%, more preferably, at least about 90% homologous with such receptor or ligand binding domains. The amino acid sequence variants possess substitutions, deletions, and/or insertions at certain positions within the amino acid sequence of the native amino acid sequence.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12 to obtain nucleotide sequences homologous to a nucleic acid encoding a protein of interest. BLAST protein searches can be performed with the XBLAST program, score=50, wordlength=3 to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. (See, e.g., Internet web site address: www.ncbi.nim.nih.gov.)

A "disorder" is any condition that would benefit from treatment of the present invention. This includes chronic and acute disorders or diseases including those pathological conditions which predispose the mammal to the disorder in question. Non-limiting examples of disorders to be treated herein include benign and malignant tumors; leukemia and lymphoid malignancies, in particular breast, ovarian, stomach, endometrial, salivary gland, lung, kidney, colon, thyroid, pancreatic, prostate or bladder cancer; neuronal, glial, astrocytal, hypothalamic and other glandular, macrophagal, epithelial, stromal and blastocoelic disorders; and inflammatory, angiogenic and immunologic disorders.

The term "effective amount" refers to an amount of a drug effective to prevent growth of and/or kill existing cancer cells. For cancer therapy, efficacy can, for example, be measured by assessing the time to disease progression (TTP) and/or determining the response rate (RR).

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "substantial amount" refers to a majority, i.e. >50% of a population, of a collection or a sample.

The term "intracellular metabolite" refers to a compound resulting from a metabolic process or reaction inside a cell on a Conjugate Compound (e.g., an antibody drug conjugate (ADC)). The metabolic process or reaction may be an enzymatic process such as proteolytic cleavage of a peptide linker of the Conjugate Compound, or hydrolysis of a functional group such as a hydrazone, ester, or amide. Intracellular metabolites include, but are not limited to, antibodies and free drug which have undergone intracellular cleavage after entry, diffusion, uptake or transport into a cell.

The terms "intracellularly cleaved" and "intracellular cleavage" refer to a metabolic process or reaction inside a cell on a Conjugate Compound whereby the covalent attachment, e.g., the linker, between the drug moiety (D) and the Ligand (e.g., an antibody) is broken, resulting in the free drug dissociated from the antibody inside the cell. The cleaved moieties of the Conjugate Compound are thus intracellular metabolites (e.g., Ligand-Linker fragment, Drug-Linker fragment or Drug).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The term "cytotoxic activity" refers to a cell-killing, cytostatic or anti-proliferation effect of a Conjugate Compound, Drug Compound or an intracellular metabolite. Cytotoxic activity may be expressed as the $IC_{50}$ value which is the concentration (molar or mass) per unit volume at which half the cells survive.

The term "cytotoxic agent" as used herein refers to a substance that inhibits or prevents the function of cells and/or causes destruction of cells. The term is intended to include radioactive isotopes (e.g., $^{211}At$, $^{131}I$, $^{125}I$, $^{90}Y$, $^{186}Re$, $^{188}Re$, $^{153}Sm$, $^{212}Bi$, $^{32}P$, $^{60}C$, and radioactive isotopes of Lu), chemotherapeutic agents, and toxins such as small molecule toxins or enzymatically active toxins of bacterial, fungal, plant or animal origin, including synthetic analogs and derivatives thereof. In some embodiments, a cytotoxic agent is not a radioactive isotope.

A "chemotherapeutic agent" is a chemical compound useful in the treatment of cancer.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

An "isolated" molecule is a molecule that is identified and separated from at least one contaminant molecule with which it is ordinarily associated in its natural source. An isolated molecule is other than in the form or setting in which it is found in nature. Isolated molecules therefore are distinguished from molecule as it exists in natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, a DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking can be accomplished by ligation at convenient restriction sites. If such sites do not exist, synthetic oligonucleotide adaptors or linkers can be used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers.

It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The terms "cancer" and "cancerous" refer to or describe the physiological condition in mammals that is typically characterized by unregulated cell growth. A "tumor" comprises one or more cancerous cells.

An "autoimmune disease" herein is a disease or disorder arising from and directed against an individual's own tissues or a co-segregate or manifestation thereof or resulting condition therefrom.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Examples of a "patient" include, but are not limited to, a human, rat, mouse, guinea pig, monkey, pig, goat, cow, horse, dog, cat, bird and fowl. In an exemplary embodiment, the patient is a human.

The term "Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

The term "$C_1$-$C_8$ alkyl" refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl; unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl, methyl, ethyl, propyl, isopropyl, n-butyl, isobutyl, sec-butyl, tert-butyl, n-pentyl, isopentyl, neopentyl, n-hexyl, isohexyl, 2-methylpentyl, 3-methylpentyl, 2,2-dimethylbutyl, 2,3-dimethylbutyl, 2,2-dimethylpentyl, 2,3-dimethylpentyl, 3,3-dimethylpentyl, 2,3,4-trimethylpentyl, 3-methylhexyl, 2,2-dimethylhexyl, 2,4-dimethylhexyl, 2,5-dimethylhexyl, 3,5-dimethylhexyl, 2,4-dimethylpentyl, 2-methylheptyl, 3-methylheptyl, n-heptyl, isoheptyl, n-octyl, and isooctyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —SO$_3$R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

The term "$C_3$-$C_8$ carbocycle" refers to a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$, —NHC(O)R', —S(O)$_2$R', —S(O)R', —OH, halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

The term "$C_1$-$C_{10}$ alkylene" refers to a straight chain, saturated hydrocarbon group of the formula —(CH$_2$)$_{1-10}$—. Examples of a $C_1$-$C_{10}$ alkylene include methylene, ethylene, propylene, butylene, pentylene, hexylene, heptylene, ocytylene, nonylene and decalene.

The term "arylene" refers to an aryl group which has two covalent bonds and can be in the ortho, meta, or para configurations as shown in the following structures:

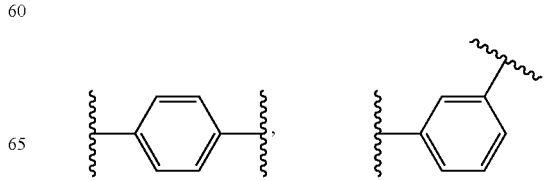

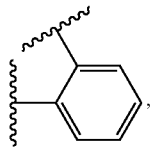

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$, —NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

The term "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$, —NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

The term "$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), aryl, —C(O)R', —OC(O)R', —C(O)OR', —C(O)$NH_2$, —C(O)NHR', —C(O)N(R')$_2$, —NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

Examples of a "hydroxyl protecting group" include, but are not limited to, methoxymethyl ether, 2-methoxyethoxymethyl ether, tetrahydropyranyl ether, benzyl ether, p-methoxybenzyl ether, trimethylsilyl ether, triethylsilyl ether, triisopropyl silyl ether, t-butyldimethyl silyl ether, triphenylmethyl silyl ether, acetate ester, substituted acetate esters, pivaloate, benzoate, methanesulfonate and p-toluenesulfonate.

"Leaving group" refers to a functional group that can be substituted by another functional group. Such leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "pharmaceutically acceptable salt" refers to a pharmaceutically acceptable organic or inorganic salt of, for example, a Conjugate Compound, Linker Drug Conjugate or a Drug. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

The term "pharmaceutically acceptable solvate" or "solvate" refer to an association of one or more solvent molecules and a compound of the invention, e.g., a Conjugate Compound, Linker-Drug Conjugate, or a Drug. Examples of solvents that form pharmaceutically acceptable solvates include, but are not limited to, water, isopropanol, ethanol, methanol, DMSO, ethyl acetate, acetic acid, and ethanolamine.

The terms "treat" or "treatment," unless otherwise indicated by context, refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

In the context of cancer, the term "treating" includes any or all of: preventing growth of tumor cells, cancer cells, or of a tumor; preventing replication of tumor cells or cancer cells, lessening of overall tumor burden or decreasing the number of cancerous cells, and ameliorating one or more symptoms associated with the disease.

In the context of an autoimmune disease, the term "treating" includes any or all of: preventing replication of cells associated with an autoimmune disease state including, but not limited to, cells that produce an autoimmune antibody, lessening the autoimmune-antibody burden and ameliorating one or more symptoms of an autoimmune disease.

In the context of an infectious disease, the term "treating" includes any or all of: preventing the growth, multiplication or replication of the pathogen that causes the infectious disease and ameliorating one or more symptoms of an infectious disease.

The following abbreviations are used herein and have the indicated definitions: Boc is N-(t-butoxycarbonyl), cit is citrulline, dap is dolaproine, DEPC is diethylphosphorylcyanidate, DIAD is diisopropylazodicarboxylate, DIEA is N,N- diisopropylethylamine, dil is dolaisoleuine, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN(CH$_3$CN) is acetonitrile, MeOH is methanol, Mtr is 4-anisyldiphenylmethyl (or 4-methoxytrityl), nor is (1S,2R)-(+)-norephedrine, PAB is p-aminobenzyl, PBS is phosphate-buffered saline (pH 7.4), PEG is polyethylene glycol, Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TBTU is O-benzotriazol-1-yl-N,N,N,N-tetramethyluronium tetrafluoroborate, TFA is trifluoroacetic acid, TLC is thin layer chromatography, UV is ultraviolet, and val is valine.

The following linker abbreviations are used herein and have the indicated definitions: Val Cit is a valine-citrulline, dipeptide site in protease cleavable linker; (Me)vc is N-methyl-valine citrulline, where the linker peptide bond has been modified to prevent its cleavage by cathepsin B; MC(PEG)6-OH is maleimidocaproyl-polyethylene glycol; SPP is N-Succinimidyl 4-(2-pyridylthio)pentanoate; and SMCC is N-Succinimidyl 4-(N-maleimidomethyl)cyclohexane-1 carboxylate.

The following cytotoxic drug abbreviations are used herein and have the indicated definitions: MMAE is mono-methyl auristatin E (MW 718); MMAF is N-methylvaline-valine-dolaisoleuine-dolaproine-phenylalanine (MW 731.5); MMAF-DMAEA is MMAF with DMAEA (dimethylaminoethylamine) in an amide linkage to the C-terminal phenylalanine (MW 801.5); MMAF-TEG is MMAF with tetraethylene glycol esterified to the phenylalanine; and MMAF-NtBu is N-t-butyl, attached as an amide to C-terminus of MMAF.

DETAILED DESCRIPTION OF THE INVENTION

The present invention provides Drug Compounds comprising an aminobenzoic acid unit. Also provided are Conjugate Compounds and Linker Drug Compounds comprising a Drug Compound.

In some embodiments, the Conjugate Compounds have the general Formula Ia:

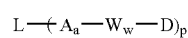

Ia and pharmaceutically acceptable salts and solvates thereof;
wherein:
L- is a Ligand unit;
-A$_a$-W$_w$— is a Linker unit (LU), wherein the Linker unit includes:
-A- is a Stretcher unit,
a is 0 or 1,
each —W— is independently an Amino Acid unit,
w is an integer ranging from 0 to 12,
p ranges from 1 to about 20; and
-D is a Drug unit of the following formula

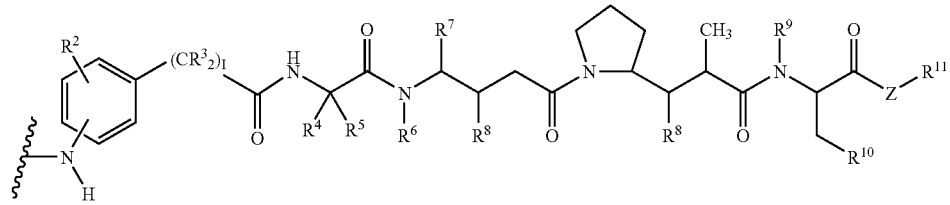

I wherein, independently at each location:
R$^2$ is selected from -hydrogen-C$_1$-C$_8$ alkyl, —O—(C$_1$-C$_8$ alkyl), -halogen, —NO$_2$, —COOH, and —C(O)OR$^{11}$;
each R$^3$ is selected independently from -hydrogen and —C$_1$-C$_8$ alkyl;
l is an integer ranging from 0-10;
R$^4$ is selected from -hydrogen, —C$_1$-C$_8$ alkyl, —C$_3$-C$_8$ carbocycle, aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle), and R$^5$ is selected from —H and -methyl; or R$^4$ and R$^5$ jointly have the formula -(CR$^a$R$^b$)$_n$—, wherein R$^a$ and R$^b$ are independently selected from —H, —C$_1$-C$_8$ alkyl and —C$_3$-C$_8$ carbocycle and n is selected from 2, 3, 4, 5 and 6, and form a ring with the carbon atom to which they are attached;
R$^6$ is selected from —H and —C$_1$-C$_8$ alkyl;
R$^7$ is selected from —H, —C$_1$-C$_8$ alkyl, —C$_3$-C$_8$ carbocycle, aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl(C$_3$-C$_8$ heterocycle);
each R$^8$ is independently selected from —H, —OH, —C$_1$-C$_8$ alkyl, —C$_3$-C$_8$ carbocycle, —O-alkyl-(C$_1$-C$_8$ carbocycle) and —O—(C$_1$-C$_8$ alkyl);
R$^9$ is selected from —H and —C$_1$-C$_8$ alkyl;
R$^{10}$ is selected from aryl or —C$_3$-C$_8$ heterocycle;
Z is —O—, —S—, —NH—, or —NR$^{12}$— where R$^{12}$ is C$_1$-C$_8$ alkyl or aryl; and
R$^{11}$ is selected from —H, C$_1$-C$_8$ alkyl, aryl, —C$_3$-C$_8$ heterocycle, —(CH$_2$CH$_2$O)$_r$—H, —(CH$_2$CH$_2$O)$_r$—CH$_3$, and —(CH$_2$CH$_2$O)$_r$—CH$_2$CH$_2$C(O)OH; wherein r is an integer ranging from 1-10.

In some embodiments, the Drug unit is of the following formula Ic:

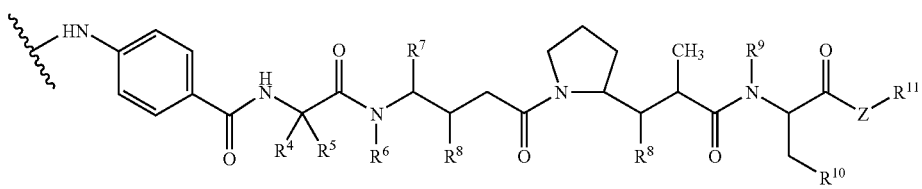

I wherein, independently at each location:

$R^4$ is selected from -hydrogen, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle), and $R^5$ is selected from —H and -methyl; or $R^4$ and $R^5$ jointly have the formula -($CR^aR^b$)$_n$—, wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl($C_3$-$C_8$ heterocycle);

each $R^8$ is independently selected from —H, —OH, —$C_1$-$C_8$ alkyl, —$C_3$-$C_8$ carbocycle, —O-alkyl-($C_1$-$C_8$ carbocycle) and —O—($C_1$-$C_8$ alkyl);

$R^9$ is selected from —H and —$C_1$-$C_8$ alkyl;

$R^{10}$ is selected from aryl or —$C_3$-$C_8$ heterocycle;

Z is —O—, —S—, —NH—, or —$NR^{12}$— where $R^{12}$ is $C_1$-$C_8$ alkyl or aryl; and $R^{11}$ is selected from —H, $C_1$-$C_8$ alkyl, aryl, —$C_3$-$C_8$ heterocycle, —($CH_2CH_2O$)$_r$—H, —($CH_2CH_2O$)$_r$—$CH_3$, and —($CH_2CH_2O$)$_r$—$CH_2CH_2C(O)OH$; wherein r is an integer ranging from 1-10.

In some embodiments, the Drug unit is of the following formula Id:

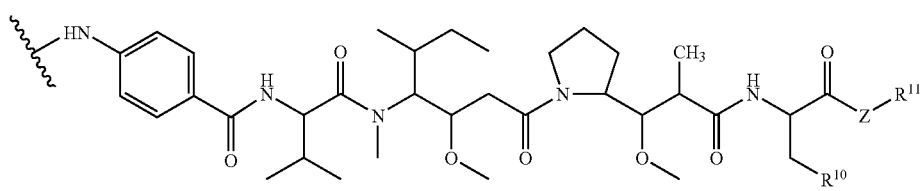

Id wherein, independently at each location:

$R^{10}$ is selected from aryl group or —$C_3$-$C_8$ heterocycle;

Z is —O—, —S—, —NH—, or —$NR^{12}$— where $R^{12}$ is $C_1$-$C_8$ alkyl or aryl; and $R^{11}$ is selected from —H, $C_1$-$C_8$ alkyl, aryl, —$C_3$-$C_8$ heterocycle, —($CH_2CH_2O$)$_n$—H, —($CH_2CH_2O$)$_r$—$CH_3$, and —($CH_2CH_2O$)$_r$—$CH_2CH_2C(O)OH$; wherein r is an integer ranging from 1-10.

In some embodiments, the Drug unit is of the following formula Ie:

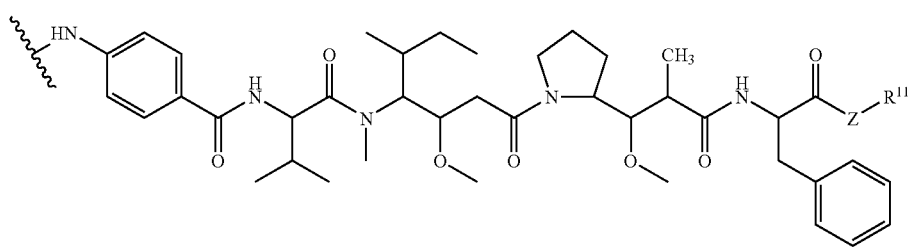

Ie wherein:

Z is —O—, —S—, —NH—, or —$NR^{12}$— where $R^{12}$ is $C_1$-$C_8$ alkyl or aryl; and $R^{11}$ is selected from —H, $C_1$-$C_8$ alkyl, aryl, —$C_3$-$C_8$ heterocycle, —($CH_2CH_2O$)$_r$—H, —($CH_2CH_2O$)$_r$—$CH_3$, and —($CH_2CH_2O$)$_r$—$CH_2CH_2C(O)OH$; wherein r is an integer ranging from 1-10.

In some embodiments, the Drug unit is of the following formula If:

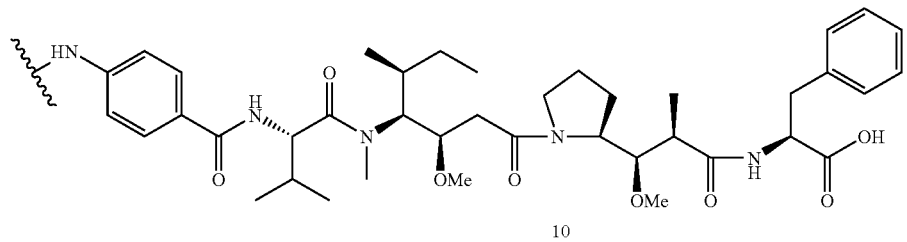

In some embodiments, a Linker-Drug Compound of the following formula IIa is provided:

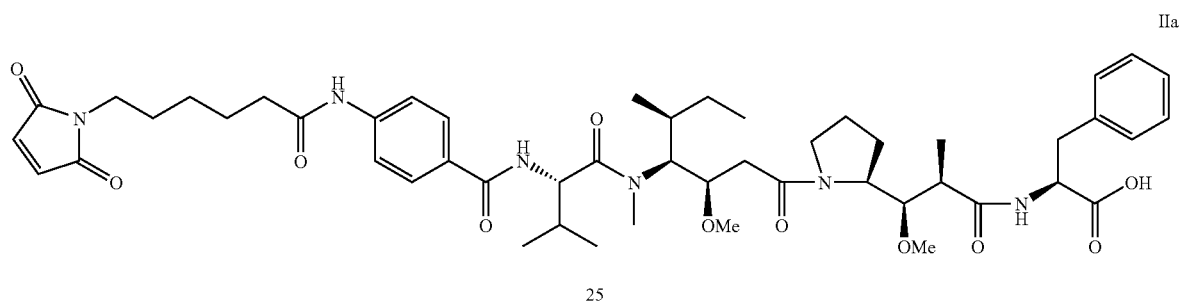

IIa

In some embodiments, a Linker-Drug Compound is of the following formula IIb is provided:

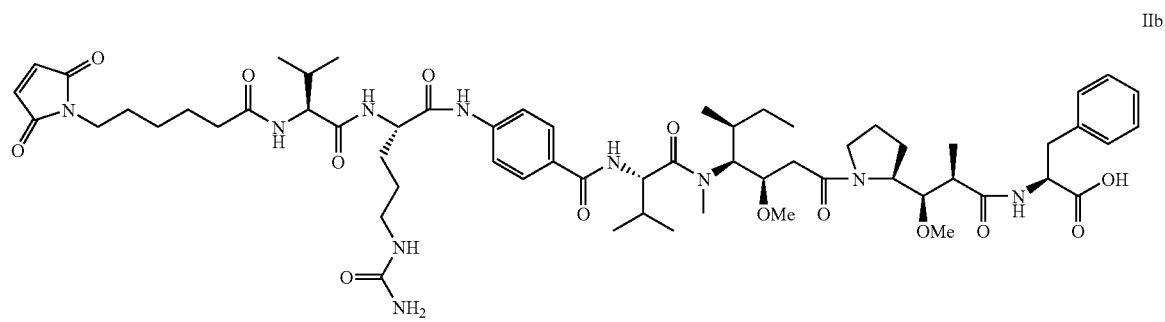

IIb

In some embodiments, a Linker-Drug Compound is of the following formula IIc is provided:

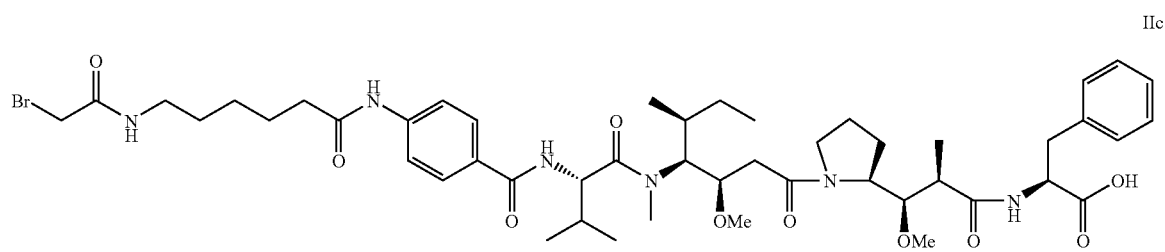

IIc

In related embodiments, Br is substituted by another halogen.

In some embodiments, a Linker-Drug Compound is of the following formula IId is provided:

In related embodiments, Br is substituted by another halogen.

Ligand Unit

The Ligand unit (L-) of the Conjugate Compounds includes within its scope any unit of a Ligand (L) that binds or reactively associates or complexes with a receptor, antigen or other receptive moiety associated with a given target-cell population. A Ligand is a molecule that binds to, complexes with, or reacts with a moiety of a cell population sought to be targeted. In one aspect, the Ligand unit acts to deliver the Drug unit to the particular target cell population with which the Ligand unit reacts. Such Ligands include, but are not limited to, large molecular weight proteins such as, for example, full-length antibodies, antibody fragments, smaller molecular weight proteins, polypeptide or peptides, lectins, glycoproteins, non-peptides, vitamins, nutrient-transport molecules (such as, but not limited to, transferrin), or any other cell binding molecule or substance.

A Ligand unit can form a bond to a Linker Unit or a Drug Unit. A Ligand unit can form a bond to a Linker unit via a heteroatom of the Ligand. Heteroatoms that may be present on a Ligand unit include sulfur (in one embodiment, from a sulfhydryl group of a Ligand), oxygen (in one embodiment, from a carbonyl, carboxyl or hydroxyl group of a Ligand) and nitrogen (in one embodiment, from a primary or secondary amino group of a Ligand). These heteroatoms can be present on the Ligand in the Ligand's natural state, for example a naturally-occurring antibody, or can be introduced into the Ligand via chemical modification.

In one embodiment, a Ligand has a sulfhydryl group and the Ligand bonds to the Linker unit via the sulfhydryl group's sulfur atom. In another embodiment, the Ligand has one or more lysine residues that can be chemically modified to introduce one or more sulfhydryl groups. The Ligand unit bonds to the Linker unit via the sulfhydryl group. Reagents that can be used to modify lysines include, but are not limited to, N-succinimidyl S-acetylthioacetate (SATA) and 2-Iminothiolane hydrochloride (Traut's Reagent).

In another embodiment, the Ligand can have one or more carbohydrate groups that can be chemically modified to have one or more sulfhydryl groups. The Ligand unit bonds to the Linker Unit via the sulfhydryl group's sulfur atom. In yet another embodiment, the Ligand can have one or more carbohydrate groups that can be oxidized to provide an aldehyde (—CHO) group (see, e.g., Laguzza et al., 1989, J. Med. Chem. 32(3):548-55). The corresponding aldehyde can form a bond with a reactive site on a portion of a Linker unit. Reactive sites that can react with a carbonyl group on a Ligand include, but are not limited to, hydrazine and hydroxylamine. Other protocols for the modification of proteins for the attachment or association of Drug units are described in Coligan et al., Current Protocols in Protein Science, vol. 2, John Wiley & Sons (2002), incorporated herein by reference.

The Ligand unit can include, for example a protein, polypeptide, or peptide include, but are not limited to, transferrin, epidermal growth factors ("EGF"), bombesin, gastrin, gastrin-releasing peptide, platelet-derived growth factor, IL-2, IL-6, transforming growth factor ("TGF"), such as TGF-α or TGF-β, vaccinia growth factor ("VGF"), insulin and insulin-like growth factors I and II, lectins and apoprotein from low density lipoprotein.

The Ligand unit can also include an antibody, such as polyclonal antibodies or monoclonal antibodies. The antibody can be directed to a particular antigenic determinant, including for example, a cancer cell antigen, a viral antigen, a microbial antigen, a protein, a peptide, a carbohydrate, a chemical, nucleic acid, or fragments thereof. Methods of producing polyclonal antibodies are known in the art. A monoclonal antibody (mAb) to an antigen-of-interest can be prepared by using any technique known in the art. These include, but are not limited to, the hybridoma technique originally described by Köhler and Milstein (1975, Nature 256, 495-497), the human B cell hybridoma technique (Kozbor et al., 1983, Immunology Today 4:72), and the EBV-hybridoma technique (Cole et al., 1985, Monoclonal Antibodies and Cancer Therapy, Alan R. Liss, Inc., pp. 77-96). Such antibodies may be of any immunoglobulin class including IgG, IgM, IgE, IgA, and IgD and any subclass thereof. The hybridoma producing the mAbs of use in this invention may be cultivated in vitro or in vivo.

The monoclonal antibody can be, for example, a human monoclonal antibody, a humanized monoclonal antibody, an antibody fragment, or a chimeric antibody (e.g., a human-mouse antibody). Human monoclonal antibodies may be made by any of numerous techniques known in the art (e.g., Teng et al., 1983, Proc. Natl. Acad. Sci. USA 80:7308-7312; Kozbor et al., 1983, Immunology Today 4:72-79; and Olsson et al., 1982, Meth. Enzymol. 92:3-16).

The antibody can also be a bispecific antibody. Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, Nature 305:537-539; International Publication No. WO 93/08829, Traunecker et al., 1991, EMBO J. 10:3655-3659.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

For example, the bispecific antibodies can have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690) which is incorporated herein by reference in its entirety.

For further details for generating bispecific antibodies see, for example, Suresh et al., 1986, Methods in Enzymology 121:210; Rodrigues et al., 1993, J. Immunology 151:6954-6961; Carter et al., 1992, Bio/Technology 10:163-167; Carter et al., 1995, J. Hematotherapy 4:463-470; Merchant et al., 1998, Nature Biotechnology 16:677-681. Using such techniques, bispecific antibodies can be prepared for use in the treatment or prevention of disease as defined herein.

Bifunctional antibodies are also described in European Patent Publication No. EPA 0 105 360. As disclosed in this reference, hybrid or bifunctional antibodies can be derived either biologically, i.e., by cell fusion techniques, or chemically, especially with cross-linking agents or disulfide-bridge forming reagents, and may comprise whole antibodies or fragments thereof. Methods for obtaining such hybrid antibodies are disclosed for example, in International Publication WO 83/03679, and European Patent Publication No. EPA 0 217 577, both of which are incorporated herein by reference.

The antibody also can be a functionally active fragment, derivative or analog of an antibody that immunospecifically binds to a target antigen (e.g., a cancer antigen, a viral antigen, a microbial antigen, or other antibodies bound to cells or matrix). In this regard, "functionally active" means that the fragment, derivative or analog is able to recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (see, e.g., Kabat et al., 1991, Sequences of Proteins of Immunological Interest, Fifth Edition, National Institute of Health, Bethesda, Md.; Kabat et al., 1980, J. Immunology 125(3):961-969).

Other useful antibodies include fragments of antibodies such as, but not limited to, F(ab')$_2$ fragments, Fab fragments, Fab', Fv fragments and heavy chain and light chain dimers of antibodies, or any minimal fragment thereof such as Fvs or single chain antibodies (SCAs) (e.g., as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54).

Recombinant antibodies, such as chimeric and humanized monoclonal antibodies, comprising both human and non-human portions, which can be made using standard recombinant DNA techniques, also can be used. (See, e.g., U.S. Pat. No. 4,816,567; and U.S. Pat. No. 4,816,397.) Humanized antibodies are antibody molecules from non-human species having one or more complementarity determining regions (CDRs) from the non-human species and a framework region from a human immunoglobulin molecule. (See, e.g., U.S. Pat. No. 5,585,089.) Chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al., 1988, Science 239:1534; and Beidler et al., 1988, J. Immunol. 141:4053-4060.

Completely human antibodies can be used. Human antibodies can be prepared, for example, using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies. see, e.g., U.S. Pat. Nos. 5,625,126; 5,633, 425; 5,569,825; 5,661,016; and 5,545,806. Other human antibodies can be obtained commercially from, for example, Abgenix, Inc. (Freemont, Calif.) and Genpharm (San Jose, Calif.).

Human antibodies that recognize a selected epitope also can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, Biotechnology 12:899-903.) Human antibodies can also be produced using various techniques known in the art, including phage display libraries (see, e.g., Hoogenboom and Winter, 1991, J. Mol. Biol. 227:381; Marks et al., 1991, J. Mol. Biol. 222:581; Quan and Carter, 2002, "The rise of monoclonal antibodies as therapeutics," in Anti-IgE and Allergic Disease, Jardieu, P. M. and Fick Jr., R. B, eds., Marcel Dekker, New York, N.Y., Chapter 20, pp. 427-469).

In other embodiments, the antibody is a fusion protein of an antibody, or a functionally active fragment thereof. For example, an antibody can be fused via a covalent bond (e.g., a peptide bond) at either the N-terminus or the C-terminus to an amino acid sequence of another protein (or portion thereof, such as at least a 10, 20 or 50 amino acid portion of the protein) that is not the antibody.

Antibodies also include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including but not limited to specific chemical cleavage, acetylation, formylation, metabolic synthesis in the presence of tunicamycin, etc. Additionally, the analog or derivative can contain one or more unnatural amino acids.

The antibodies can have modifications (e.g., substitutions, deletions or additions) in amino acid residues that interact with Fc receptors. In particular, antibodies include antibodies having modifications in amino acid residues identified as involved in the interaction between the anti-Fc domain and the FcRn receptor (see, e.g., International Publication No. WO 97/34631, which is incorporated herein by reference in its entirety). Antibodies immunospecific for a target antigen can be obtained commercially or other source or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

Examples of antibodies available for the treatment of cancer include, but are not limited to, humanized anti HER2 monoclonal antibody, HERCEPTIN® (trastuzumab; Genentech); RITUXAN® (rituximab; Genentech) which is a chimeric anti CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine IgG2a antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (Medimmune, Inc., MD) which is a humanized antibody for the treatment of sarcoma; Campath I/H (Leukosite, MA) which is a humanized IgG1 antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens (exemplary cancers are indicated in parentheses): CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific membrane antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti transferrin receptor (carcinomas), p97 (melanoma), MUC1-KLH (breast cancer), CEA (colorectal), gp100 (melanoma), MART1 (melanoma), prostate specific antigen (PSA) (prostate), IL-2 receptor (T-cell leukemia and lymphomas), CD20 (non Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail et al., 1993, Science 261:212-215), BR64 (Trail et al., 1997, Cancer Research 57:100-105), mAbs against the CD40 antigen, such as S2C6 mAb (Francisco et al., 2000, Cancer Res. 60:3225-3231) and chimeric and humanized variants thereof, mabs against the cD33 antigen; mabs against the EphA2 antigen; mAbs against the CD70 antigen, such as 1F6 mAb and 2F2 mAb and chimeric and humanized variants thereof, and mAbs against the CD30 antigen, such as AC10 (Bowen et al., 1993, J. Immunol. 151:5896-5906; Wahl et al., 2002, Cancer Res. 62(13):3736-42) and chimeric and humanized variants thereof. Many other internalizing antibodies that bind to tumor associated antigens can be used and have been reviewed (see, e.g., Franke et al., 2000, Cancer Biother. Radiopharm. 15:459 76; Murray, 2000, Semin. Oncol. 27:64 70; Breitling et al., Recombinant Antibodies, John Wiley, and Sons, New York, 1998).

In some embodiments, known antibodies for the treatment or prevention of an autoimmune disease are used in accordance with the compositions and methods of the invention. Antibodies immunospecific for an antigen of a cell that is responsible for producing autoimmune antibodies can be obtained from a commercial or other source or produced by any method known to one of skill in the art such as, e.g., chemical synthesis or recombinant expression techniques.

In some embodiments, the antibody is immunospecific for the treatment of an autoimmune disease such as, for example, anti-nuclear antibody; anti-ds DNA; anti-ss DNA, anti-cardiolipin antibody IgM, IgG; anti-phospholipid antibody IgM, IgG; anti-SM antibody; anti-mitochondrial antibody; thyroid antibody; microsomal antibody; thyroglobulin antibody; anti-SCL 70; anti-Jo; anti-U1 RNP; anti-La/SSB; anti-SSA; anti-SSB; anti-perital cells antibody; anti-histones; anti-RNP; C ANCA; P ANCA; anti centromere; anti fibrillarin, and anti-GBM antibody. In one embodiment, the Ligand binds to an activated lymphocyte that is associated with an autoimmune disease.

In certain embodiments, the antibody can bind to a receptor or a receptor complex expressed on a target cell (e.g., an activated lymphocyte). The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD19, CD22, CD28, CD79, CD90, CD152/CTLA 4, PD 1, and ICOS. Non-limiting examples of suitable TNF receptor superfamily members are CD27, CD40, CD95/Fas, CD134/OX40, CD137/4 1BB, TNF R1, TNFR2, RANK, TACI, BCMA, osteoprotegerin, Apo2/TRAIL R1, TRAIL R2, TRAIL R3, TRAIL R4, and APO 3. Non-limiting examples of suitable integrins are CD11a, CD11b, CD11c, CD18, CD29, CD41, CD49a, CD49b, CD49c, CD49d, CD49e, CD49f, CD103, and CD104. Non-limiting examples of suitable lectins are C type, S type, and I type lectin.

In another specific embodiment, useful Ligands immunospecific for a viral or a microbial antigen are monoclonal antibodies. The antibodies may be chimeric, humanized or human monoclonal antibodies. As used herein, the term "viral antigen" includes, but is not limited to, any viral peptide, polypeptide protein (e.g., HIV gp120, HIV nef, RSV F glycoprotein, influenza virus neuraminidase, influenza virus hemagglutinin, HTLV tax, herpes simplex virus glycoprotein (e.g., gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response.

Antibodies immunospecific for a viral or microbial antigen can be obtained commercially, for example, from BD Biosciences (San Francisco, Calif.), Chemicon International, Inc. (Temecula, Calif.), or Vector Laboratories, Inc. (Burlingame, Calif.) or produced by any method known to one of skill in the art such as, e.g., chemical synthesis or recombinant expression techniques. The nucleotide sequence encoding antibodies that are immunospecific for a viral or microbial antigen can be obtained, e.g., from the GenBank database or a database like it, literature publications, or by routine cloning and sequencing.

In a specific embodiment, useful Ligands are those that are useful for the treatment or prevention of viral or microbial infection in accordance with the methods disclosed herein. Examples of antibodies available useful for the treatment of viral infection or microbial infection include, but are not limited to, SYNAGIS (Medimmune, Inc., MD) which is a humanized anti-respiratory syncytial virus (RSV) monoclonal antibody useful for the treatment of patients with RSV infection; PRO542 (Progenics) which is a CD4 fusion antibody useful for the treatment of HIV infection; OSTAVIR (Protein Design Labs, Inc., CA) which is a human antibody useful for the treatment of hepatitis B virus; PROTOVIR (Protein Design Labs, Inc., CA) which is a humanized IgG1 antibody useful for the treatment of cytomegalovirus (CMV); and anti-LPS antibodies.

Other antibodies useful in the treatment of infectious diseases include, but are not limited to, antibodies against the antigens from pathogenic strains of bacteria (e.g., *Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococc aureus, Vibrio colerae, Escherichia coli, Pseudomonas aeruginosa, Campylobacter (Vibrio) fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasma* spp., *Rickettsia prowazeki, Rickettsia tsutsugumushi, Chlamydia* spp.); pathogenic fungi (e.g., *Coccidioides immitis, Aspergillus fumigatus, Candida albicans, Blastomyces dermatitidis, Cryptococcus neoformans, Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or Helminiths (*Enterobius vermicularis, Trichuris trichiura, Ascaris lumbricoides, Trichinella spiralis, Strongyloides stercoralis, Schistosoma ijaponicum, Schistosoma mansoni, Schistosoma haematobium*, and hookworms).

Other antibodies useful in this invention for treatment of viral disease include, but are not limited to, antibodies against antigens of pathogenic viruses, including as examples and not by limitation: Poxyiridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non A/Non B Hepatitis virus, Rhinoviridae, Coronaviridae, Rotoviridae, and Human Immunodeficiency Virus.

The antibody also can be an antibody that is present on a target cell or target cell population. For example, transmembrane polypeptides and other markers can be specifically expressed on the surface of one or more particular type(s) of target cells (e.g., a cancer cell) as compared to on one or more normal (e.g., a non-cancerous cell(s)). Often, such markers are more abundantly expressed on the surface of the target cells, or exhibit greater immunogenicity, as compared to those on the surface of the normal cells. The identification of such cell surface antigen polypeptides has given rise to the ability to specifically target cells for destruction via antibody-based therapies. Thus, in some embodiments, the antibodies include, but are not limited to, antibodies against tumor-associated antigens (TAA). Such tumor-associated antigens are known in the art, and can prepared for use in generating antibodies using methods and information which are well known in the art.

Linker Unit

The Conjugate Compounds typically further include a Linker unit. A "Linker unit" (LU) is a bifunctional compound which can be used to link a Drug unit and a Ligand unit to form a Conjugate Compound. Such conjugates allow the selective delivery of drugs to target cells (e.g., tumor cells). Linkers include a divalent radical such as an alkyldiyl, an aryidiyl, a heteroaryldiyl, moieties such as: —$(CR_2)_nO$ $(CR_2)_n$—, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

The Conjugate Compounds can be prepared using a Linker unit having a reactive site for binding to the Drug unit and Ligand. In some embodiments, a Linker has a reactive site which has an electrophilic group that is reactive to a nucleophilic group present on a Ligand. Useful nucleophilic groups on a Ligand include but are not limited to sulfhydryl, hydroxyl and amino groups. The heteroatom of the nucleophilic group of a Ligand is reactive to an electrophilic group on a Linker and forms a covalent bond to a Linker unit. Useful electrophilic groups include, but are not limited to maleimide and haloacetamide groups. The nucleophilic group on a Ligand provides a convenient site for attachment to a Linker.

In another embodiment, a Linker has a reactive site which has a nucleophilic group that is reactive to an electrophilic group present on a Ligand. Useful electrophilic groups on a Ligand include, but are not limited to, aldehyde and ketone carbonyl groups. The heteroatom of a nucleophilic group of a Linker can react with an electrophilic group on a Ligand and form a covalent bond to a Ligand unit. Useful nucleophilic groups on a Linker include, but are not limited to, hydrazide, oxime, amino, hydrazine, thiosemicarbazone, hydrazine carboxylate, and arylhydrazide. The electrophilic group on a Ligand provides a convenient site for attachment to a Linker.

Carboxylic acid functional groups and chloroformate functional groups are also useful reactive sites for a Linker because they can react with amino groups of a Drug to form an amide linkage. Also useful as a reactive site is a carbonate functional group on a Linker, such as but not limited to p-nitrophenyl carbonate, which can react with an amino group of a Drug to form a carbamate linkage.

In one embodiment, the Linker unit has the formula:

wherein:

-A- is a Stretcher unit;

a is 0 or 1;

each —W— is independently an Amino Acid unit; and w is independently an integer ranging from 0 to 12.

The Stretcher unit (-A-), when present, is capable of linking a Ligand unit to an amino acid unit (—W—). In this regard a Ligand (L) has a functional group that can form a bond with a functional group of a Stretcher. Useful functional groups that can be present on a ligand, either naturally or via chemical manipulation include, but are not limited to, sulfhydryl (—SH), amino, hydroxyl, carboxy, the anomeric hydroxyl group of a carbohydrate, and carboxyl. In one aspect, the Ligand functional groups are sulfhydryl and amino. Sulfhydryl groups can be generated by reduction of an intramolecular disulfide bond of a Ligand. Alternatively, sulfhydryl groups can be generated by reaction of an amino group of a lysine moiety of a Ligand using 2-iminothiolane (Traut's reagent) or another sulfhydryl generating reagent.

In one embodiment, the Stretcher unit forms a bond with a sulfur atom of the Ligand unit. The sulfur atom can be derived from a sulfhydryl group of a Ligand. Representative Stretcher units of this embodiment are depicted within the square brackets of Formulas IIIa and IIIb, wherein L-, —W—, -D, w is defined as above, and $R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_1$ alkylene-($C_3$-$C_8$ heterocyclo)-, —($C_3$-$C_8$ heterocyclo)-$C_1$-$C_{10}$ alkylene-, —($CH_2CH_2O)_r$—, and —($CH_2CH_2O)_r$—$CH_2$—; and r is an integer ranging from 1-10. It is to be understood from all the exemplary embodiments of Formula Ia, such as III-VI, that even where not denoted expressly, from 1 to 20 drug moieties are linked to a Ligand (p=1-20).

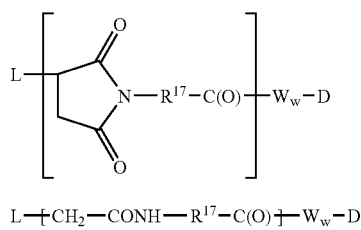

IIIa

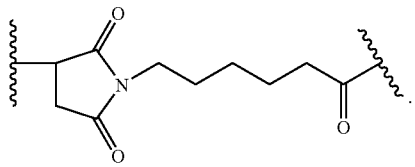

IIIb

An illustrative Stretcher unit is that of Formula IIIa wherein $R^{17}$ is —$(CH_2)_5$—:

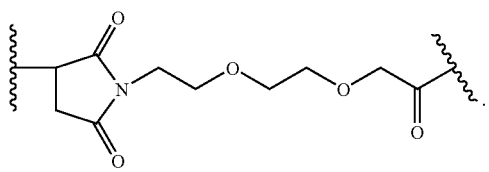

Another illustrative Stretcher unit is that of Formula IIIa wherein $R^{17}$ is —$(CH_2CH_2O)_r$—$CH_2$—; and r is 2:

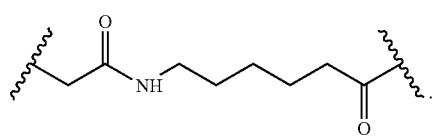

Still another illustrative Stretcher unit is that of Formula IIIb wherein
$R^{17}$ is —$(CH_2)_5$—:

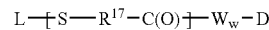

In another embodiment, the Stretcher unit is linked to the Ligand unit via a disulfide bond between a sulfur atom of the Ligand unit and a sulfur atom of the Stretcher unit. A representative Stretcher unit of this embodiment is depicted within the square brackets of Formula IV, wherein $R^{17}$, L-, —W—, -D, w is as defined above.

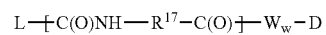

IV

In yet another embodiment, the reactive group of the Stretcher contains a reactive site that can form a bond with a primary or secondary amino group of a Ligand. Example of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —$R^{17}$—, L-, —W—, -D, and w are as defined above;

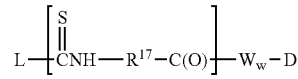

Va

Vb

In yet another aspect, the reactive group of the Stretcher contains a reactive site that is reactive to a modified carbohydrate's (—CHO) group that can be present on a Ligand. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko, T. et al. (1991) Bioconjugate Chem 2:133-41. Representative Stretcher units of this embodiment are depicted within the square brackets of Formulas VIa, VIb, and VIc, wherein —$R^{17}$—, L-, —W—, —Y—, D, w and y are as defined above.

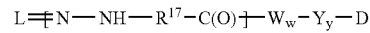

VIa

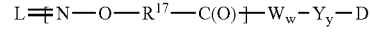

VIb

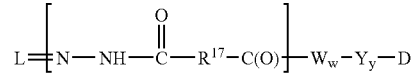

VIc

The Amino Acid unit (—W—), when present, links the Stretcher unit to the Drug moiety, and links the Ligand unit to the Drug unit if the Stretcher unit is absent.

$W_w$— is a dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from to 12:

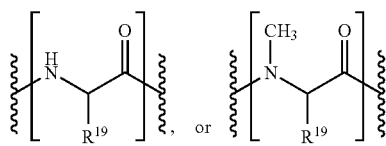

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

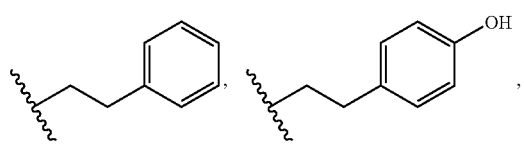

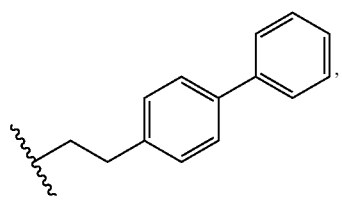

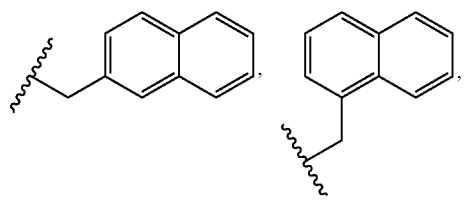

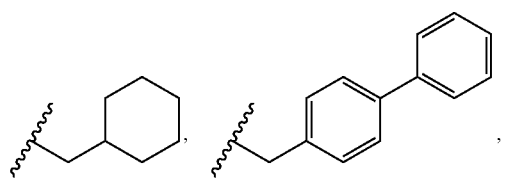

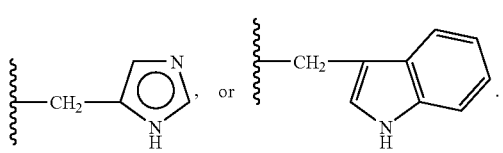

The Amino Acid unit can be enzymatically cleaved by one or more enzymes (e.g., a lysozomal enzyme, a tumor-associated protease, an intracellular enzyme) to liberate the Drug unit (-D), which in one embodiment is protonated in vivo upon release to provide a Drug (D).

Illustrative $W_w$ units are represented by formulas (VII)-(IX):

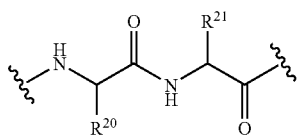

(VII)

wherein $R^{20}$ and $R^{21}$ are as follows:

| $R^{20}$ | $R^{21}$ |
|---|---|
| Benzyl | $(CH_2)_4NH_2$; |
| Methyl | $(CH_2)_4NH_2$; |
| Isopropyl | $(CH_2)_4NH_2$; |
| Isopropyl | $(CH_2)_3NHCONH_2$; |
| benzyl | $(CH_2)_3NHCONH_2$; |
| isobutyl | $(CH_2)_3NHCONH_2$; |
| sec-butyl | $(CH_2)_3NHCONH_2$; |
| 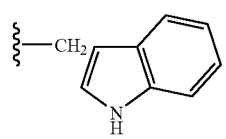 | $(CH_2)_3NHCONH_2$; |
| Benzyl | methyl; and |
| Benzyl | $(CH_2)_3NHC(=NH)NH_2$; |

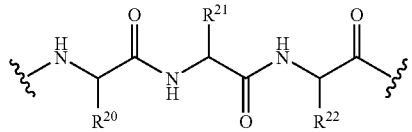

(VIII)

wherein $R^{20}$, $R^{21}$ and $R^{22}$ are as follows:

| $R^{20}$ | $R^{21}$ | $R^{22}$ |
|---|---|---|
| benzyl | benzyl | $(CH_2)_4NH_2$; |
| isopropyl | benzyl | $(CH_2)_4NH_2$; and |
| H | benzyl | $(CH_2)_4NH_2$; |

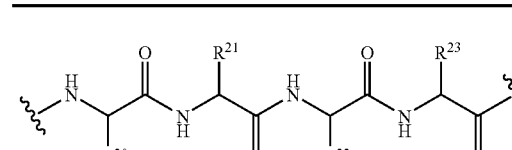

(IX)

wherein $R^{20}$, $R^{21}$, $R^{22}$ and $R^{23}$ are as follows:

| $R^{20}$ | $R^{21}$ | $R^{22}$ | $R^{23}$ |
|---|---|---|---|
| H | Benzyl | isobutyl | H; and |
| methyl | Isobutyl | methyl | isobutyl. |

Exemplary Amino Acid units include, but are not limited to, units of formula (VII) where: $R^{20}$ is benzyl and $R^{21}$ is —$(CH_2)_4NH_2$; $R^{20}$ isopropyl and $R^{21}$ is —$(CH_2)_4NH_2$; or $R^{20}$ isopropyl and $R^{21}$ is —$(CH_2)_3NHCONH_2$. Another exemplary Amino Acid unit is a unit of formula (VIII) wherein $R^{20}$ is benzyl, $R^{21}$ is benzyl, and $R^{22}$ is —$(CH_2)_4NH_2$.

Useful —$W_w$— units can be designed and optimized in their selectivity for enzymatic cleavage by a particular enzymes, for example, a lysozomal enzyme, a tumor-associated protease, or an intracellular enzyme. In one embodiment, a —$W_w$— unit is that whose cleavage is catalyzed by cathepsin B, C and D, or a plasmin protease.

In one embodiment, —$W_w$— is a dipeptide, tripeptide, tetrapeptide or pentapeptide.

When $R^{19}$, $R^{20}$, $R^{21}$, $R^{22}$ or $R^{23}$ is other than hydrogen, the carbon atom to which $R^{19}$, $R^{20}$, $R^{21}$, $R^{22}$ or $R^{23}$ is attached is chiral.

Each carbon atom to which $R^{19}$, $R^{20}$, $R^{21}$, $R^{22}$ or $R^{23}$ is attached is independently in the (S) or (R) configuration.

In one embodiment, the Amino Acid unit is valine-citrulline. In another embodiment, the Amino Acid unit is phenylalanine-lysine (i.e. fk). In yet another embodiment, the Amino Acid unit is N-methylvaline-citrulline. In yet another embodiment, the Amino Acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

In certain embodiments, the Amino Acid unit can comprise natural amino acids. In other embodiments, the Amino Acid unit can comprise non-natural amino acids.

Drug Compound

The Drug Compound is of the dolastatin/auristatin type, which have been shown to interfere with microtubule dynamics, GTP hydrolysis, and/or nuclear and cellular division and have anticancer and/or antifungal activity. D is a Drug unit (moiety) having a nitrogen atom that can form a bond with an Amino Acid unit or a Stretcher unit, or a Ligand unit. It is to be understood that the terms "drug unit" and "drug moiety" are synonymous and used interchangeably herein.

In some embodiments, the Drug Compound has the following Formula I:

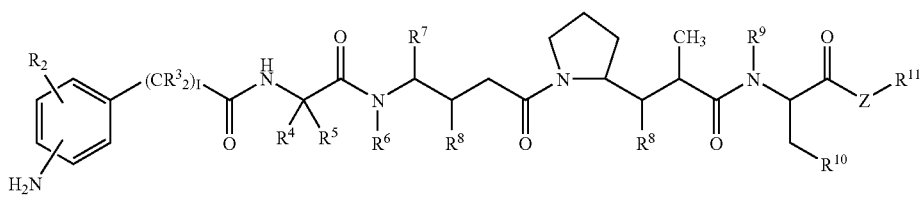

or a pharmaceutically acceptable salt or solvate thereof wherein, independently at each location:

$R^2$ is selected from -hydrogen-$C_1$-$C_8$ alkyl, —O—($C_1$-$C_8$ alkyl), halogen, —$NO_2$, —COOH, and —C(O)$OR^{11}$;

each $R^3$ is selected independently from -hydrogen and —$C_1$-$C_8$ alkyl;

l is an integer ranging from 0-10;

$R^4$ is selected from -hydrogen, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); and $R^5$ is selected from —H and -methyl; or $R^4$ and $R^5$ jointly have the formula —$(CR^aR^b)_n$—, wherein $R^a$ and $R^b$ are independently selected from —H, —$C_1$-$C_8$ alkyl and —$C_3$-$C_8$ carbocycle and n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl($C_3$-$C_8$ heterocycle);

each $R^8$ is independently selected from —H, —OH, —$C_1$-$C_8$ alkyl, —$C_3$-$C_8$ carbocycle, —O-alkyl-($C_1$-$C_8$ carbocycle) and —O—($C_1$-$C_8$ alkyl);

$R^9$ is selected from —H and —$C_1$-$C_8$ alkyl;

$R^{10}$ is selected from aryl group or —$C_3$-$C_8$ heterocycle;

Z is —O—, —S—, —NH—, or —$NR^{12}$— where $R^{12}$ is $C_1$-$C_8$ alkyl; aryl; and $R^{11}$ is selected from —H, β1-C8 alkyl, aryl, —$C_3$-$C_8$ heterocycle, —$(CH_2CH_2O)_r$—H, —$(CH_2CH_2O)_r$—$CH_3$, and —$(CH_2CH_2O)_r$—$CH_2CH_2C(O)OH$; wherein r is an integer ranging from 1-10.

In some embodiments, the Drug Compound has the following formula:

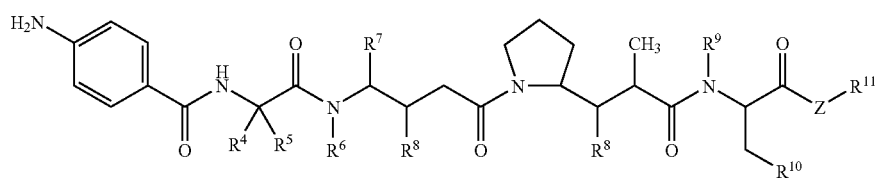

wherein independently at each location:

$R^4$ is selected from -hydrogen, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle); and $R^5$ is selected from —H and -methyl; or $R^4$ and $R^5$ jointly have the formula -$(CR^aR^b)_n$—, wherein $R^a$ and $R^b$ are independently selected from —H, —$C_1$-$C_8$ alkyl and —$C_3$-$C_8$ carbocycle, n is selected from 2, 3, 4, 5 and 6, and form a ring with the carbon atom to which they are attached;

$R^6$ is selected from —H and —$C_1$-$C_8$ alkyl;

$R^7$ is selected from —H, —$C_1$-$C_8$ alkyl, —$C_3$-$C_8$ carbocycle, aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl($C_3$-$C_8$ heterocycle);

each $R^8$ is independently selected from —H, —OH, —$C_1$-$C_8$ alkyl, —$C_3$-$C_8$ carbocycle, —O-alkyl-($C_1$-$C_8$ carbocycle) and —O—($C_1$-$C_8$ alkyl);

$R^9$ is selected from —H and —$C_1$-$C_8$ alkyl;

$R^{10}$ is selected from aryl group or —$C_3$-$C_8$ heterocycle;

Z is —O—, —S—, —NH—, or —$NR^{12}$— where $R^{12}$ is $C_1$-$C_8$ alkyl or aryl; and $R^{11}$ is selected from —H, $C_1$-$C_8$ alkyl, aryl, —$C_3$-$C_8$ heterocycle, —$(CH_2CH_2O)_r$—H, —$(CH_2CH_2O)_r$—$CH_3$, and —$(CH_2CH_2O)_r$—$CH_2CH_2C(O)OH$; wherein r is an integer ranging from 1-10.

In some embodiments, the Drug Compound has the following formula:

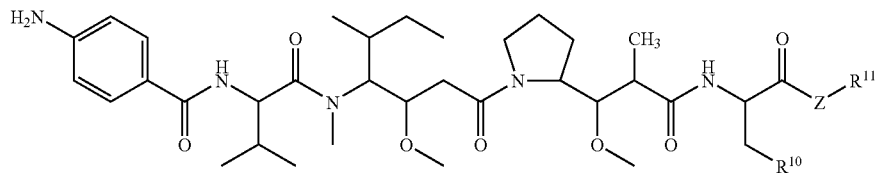

wherein independently as each location:
$R^{10}$ is selected from aryl group or —$C_3$-$C_8$ heterocycle;
Z is —O—, —S—, —NH—, or —$NR^{12}$— where $R^{12}$ is $C_1$-$C_8$ alkyl or aryl; and
$R^{11}$ is selected from —H, $C_1$-$C_8$ alkyl, aryl, —$C_3$-$C_8$ heterocycle, —$(CH_2CH_2O)_r$—H, —$(CH_2CH_2O)_r$—$CH_3$, and —$(CH_2CH_2O)_r$—$CH_2CH_2C(O)OH$; wherein r is an integer ranging from 1-10.

In some embodiments, the Drug Compound has the following formula:

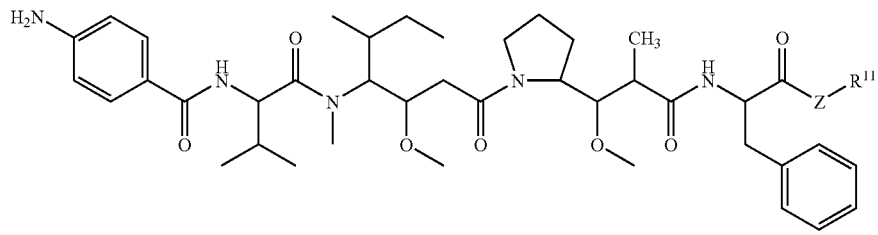

wherein Z is —O—, —S—, —NH—, or —$NR^{12}$— where $R^{12}$ is $C_1$-$C_8$ alkyl or aryl; and
$R^{11}$ is selected from —H, $C_1$-$C_8$ alkyl, aryl, —$C_3$-$C_8$ heterocycle, —$(CH_2CH_2O)_r$—H, —$(CH_2CH_2O)_r$—$CH_3$, and —$(CH_2CH_2O)_r$—$CH_2CH_2C(O)OH$; wherein r is an integer ranging from 1-10.

In some embodiments, the Drug Compound has the following formula:

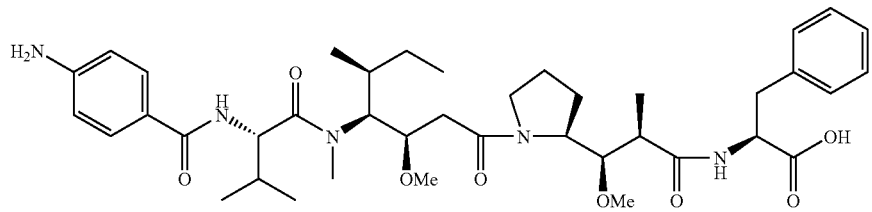

Typically, peptide-based Drugs can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry.

Non-natural amino acids Boc-Dolaproine (Boc-Dap), Dolaisoleuine-OtBu (Dil-OtBu) and dipeptide Cbz-Val-Dil-OtBu can be prepared as described in U.S. Pat. No. 5,635,483 and Peftit et al., 1998, Anti-Cancer Drug Des. p. 243.

The synthesis of illustrative Drugs Compounds of general Formula I (esters 10 or free acids 10a) are depicted in the following Scheme 1.

Scheme 1
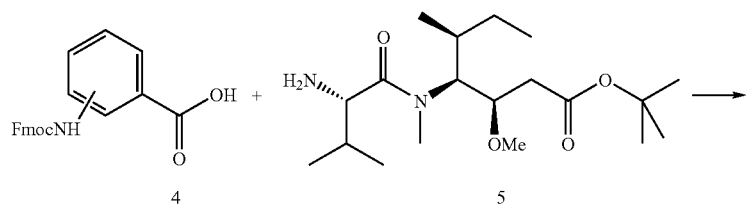
4
5
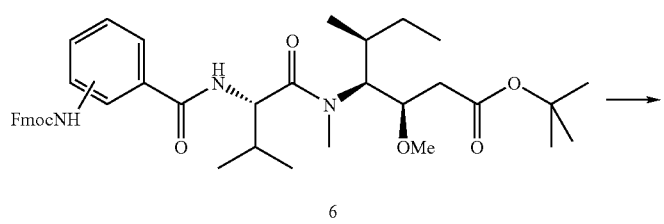
6
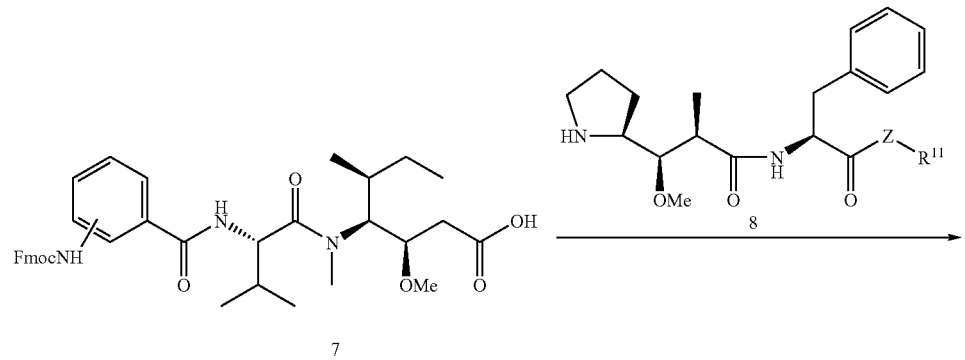
7
8
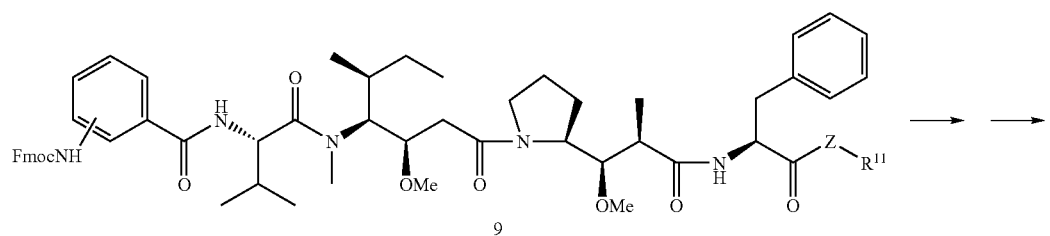
9
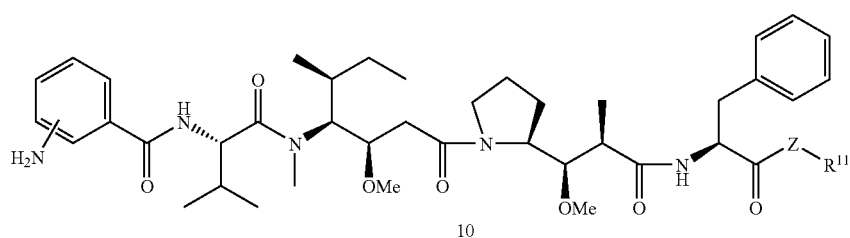
10
When Z = O, $R^{11}$ = t-butyl -continued

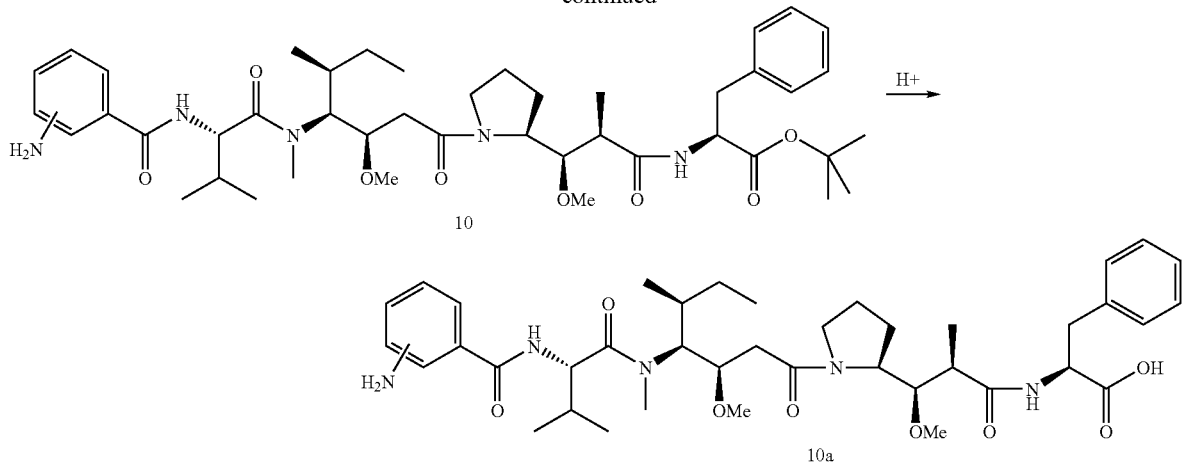

where, Z is —O—, —S—, —NH—, or —NR$^{12}$— where R$^{12}$ is C$_1$-C$_8$ alkyl;

R$^{11}$ is selected from —H, C$_1$-C$_8$ alkyl, aryl, —C$_3$-C$_8$ heterocycle, —(CH$_2$CH$_2$O)$_r$—H, and —(CH$_2$CH$_2$O)$_r$—CH$_3$; r is an integer ranging from 1-10.

In one aspect, compound 10 has Z=O, R$^{11}$=methyl. In another aspect, Z=O, R$^{11}$=tert-butyl. In yet another aspect, Drug Compound 10 has Z=O, R$^{11}$=OH (compound 10a).

The synthesis of an illustrative Stretcher having an electrophilic maleimide group is illustrated in Schemes 2-3. General synthetic methods useful for the synthesis of a Linker are described in Scheme 4. Scheme 5 presents a general outline for the synthesis of a Drug-Linker Compound, while Scheme 6 presents an alternate route for preparing a Conjugate Compound, and Scheme 7 illustrates the synthesis of Conjugate Compounds having, for example but not limited to, 2 or 4 drugs per Ligand.

Scheme 2

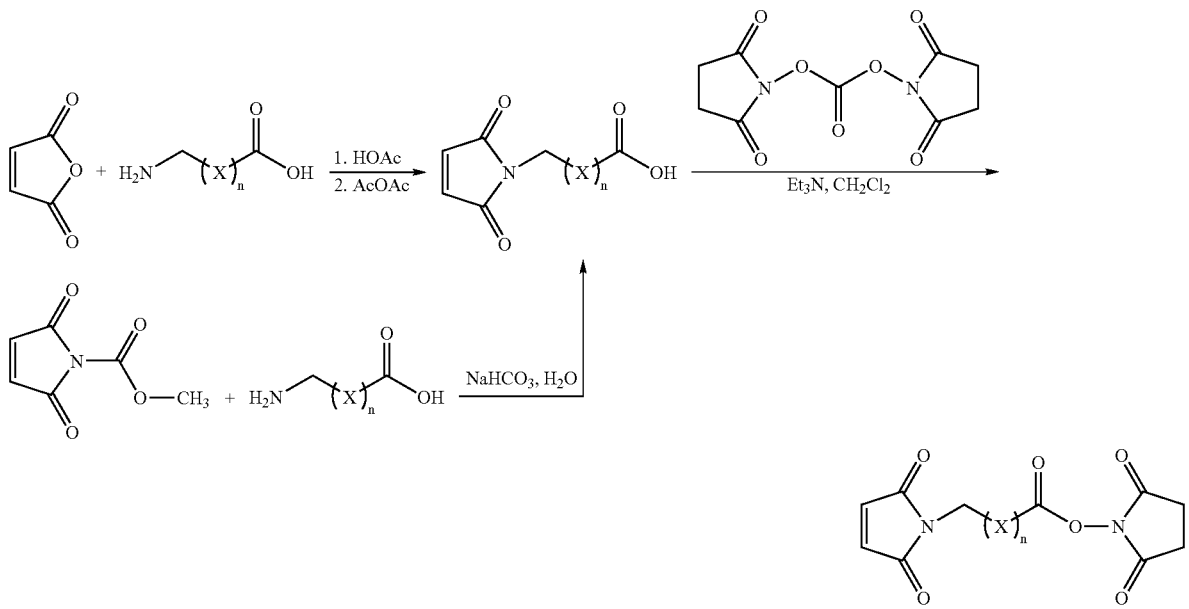

where X is —CH$_2$— or —CH$_2$OCH$_2$—; and n is an integer ranging either from 0-10 when X is —CH$_2$—; or 1-10 when X is —CH$_2$OCH$_2$—.

The method shown in Scheme 3 combines maleimide with a glycol under Mitsunobu conditions to make a polyethylene glycol maleimide Stretcher (see for example, Walker, J. Org. Chem. 1995, 60, 5352-5), followed by installation of a p-nitrophenyl carbonate Reactive Site group.

Scheme 3

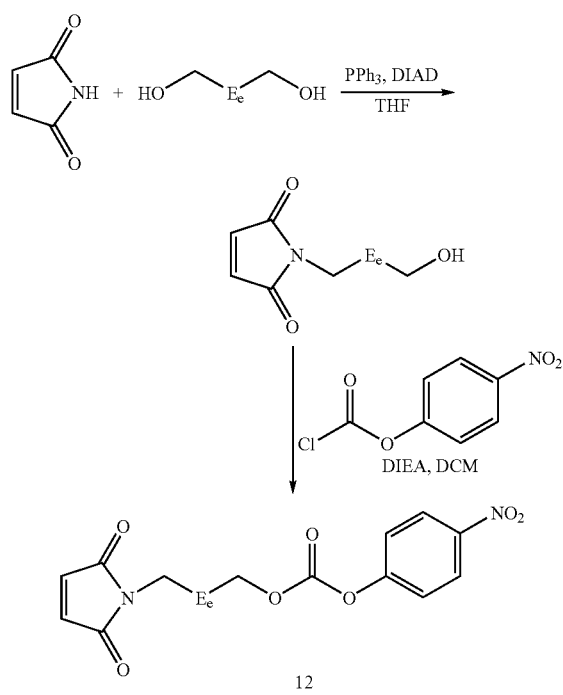

where E is —CH$_2$— or —CH$_2$OCH$_2$—; and e is an integer ranging from 0-100. In some embodiments, e is an integer ranging from 0-8. In other embodiments, e is an integer ranging from 0-10.

Alternatively, PEG-maleimide and PEG-haloacetamide stretchers can be prepared as described by Frisch et al., 1996, Bioconjugate Chem. 7:180-186.

Scheme 4 illustrates a general synthesis of an illustrative Linker unit containing a maleimide Stretcher group.

Scheme 4

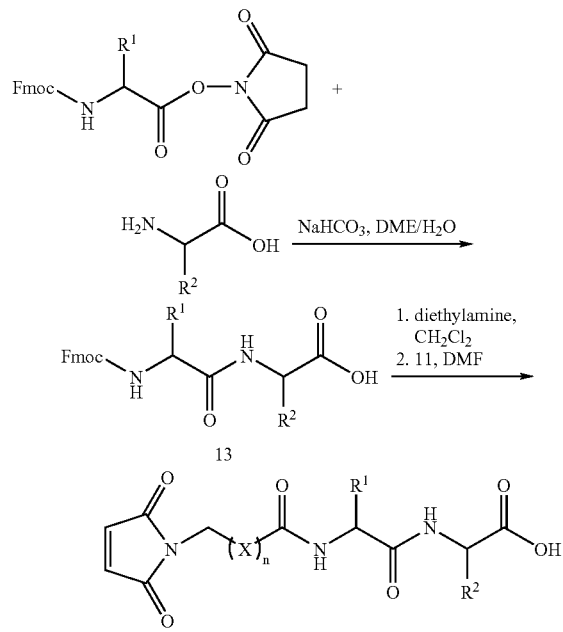

$R^1$ = benzyl; $R^2$ = (CH$_2$)$_4$NHMtr (15)
$R^1$ = isopropyl; $R^2$ = (CH$_2$)$_3$NHCONH$_2$ (16)

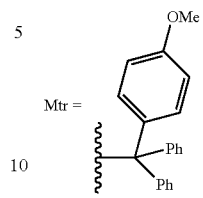

Useful Stretchers may be incorporated into a Linker using the commercially available intermediates from Molecular Biosciences (Boulder, Colo.) described below by utilizing known techniques of organic synthesis.

Stretchers of formula (IIIa) can be introduced into a Linker by reacting the following intermediates with the N-terminus of an Amino Acid unit as depicted in Schemes 7 and 8:

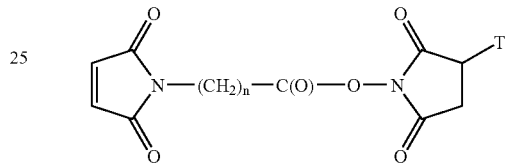

where n is an integer ranging from 1-10 and T is —H or —SO$_3$Na;

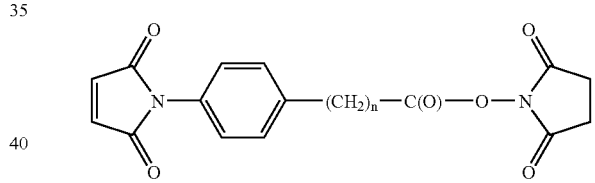

where n is an integer ranging from 0-3;

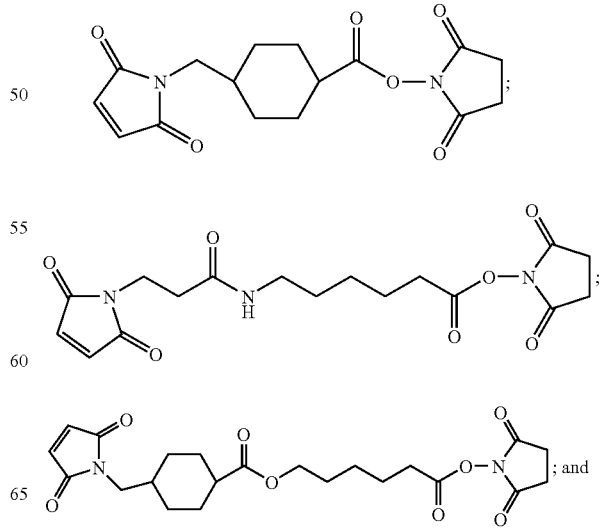

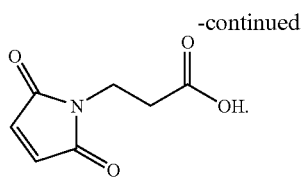

Stretcher units of formula (IIIb) can be introduced into a Linker by reacting the following intermediates with the N-terminus of an Amino Acid unit:

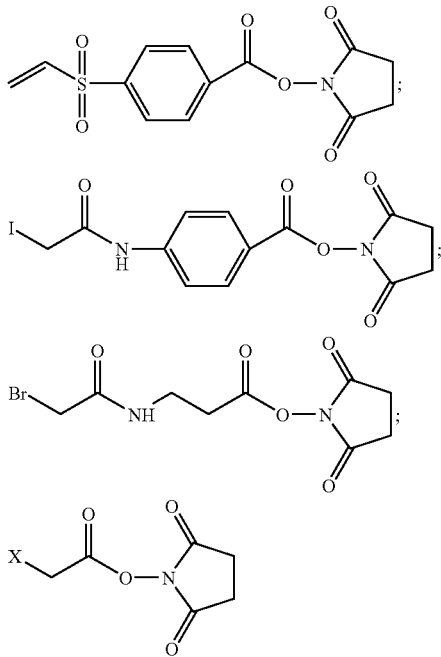

where X is —Br or —I; and

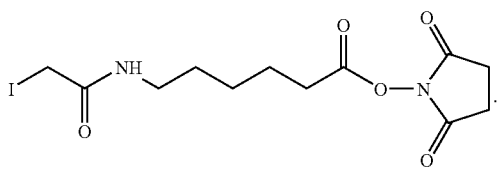

Stretcher units of formula (IV) can be introduced into a Linker by reacting the following intermediates with the N-terminus of an Amino Acid unit:

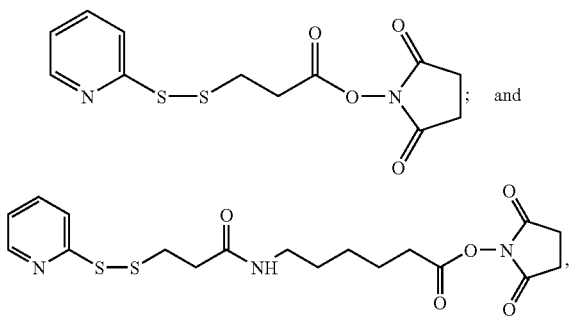

Stretcher units of formula (Va) can be introduced into a Linker by reacting the following intermediates with the N-terminus of an Amino Acid unit:

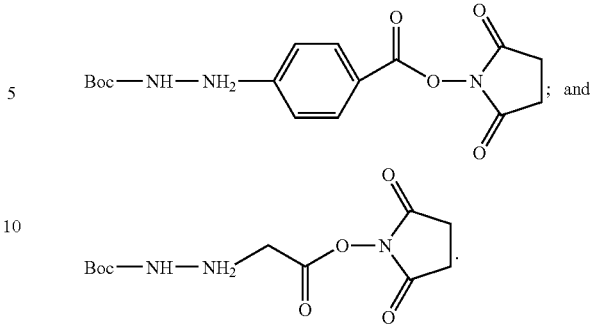

Other useful Stretchers may be synthesized according to known procedures. The Stretchers may have the general Formula Ib

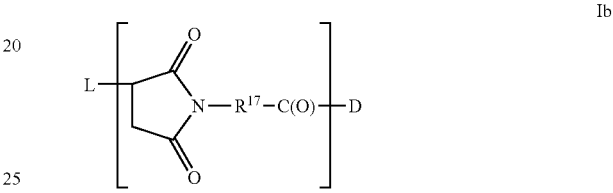

wherein $R^{17}$ is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_r$—, and —$(CH_2CH_2O)_r$—$CH_2$—; and r is an integer ranging from 1-100.

Aminooxy Stretchers of the formula shown below can be prepared by treating alkyl halides with N-Boc-hydroxylamine according to procedures described in Jones et al., 2000, Tetrahedron Letters 41(10):1531-1533; and Gilon et al., 1967, Tetrahedron 23(11):4441-4447.

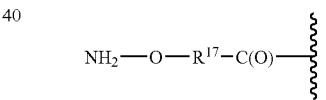

where —$R^{17}$— is selected from —$C_1$-$C_{10}$ alkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$(CH_2CH_2O)_r$—, and —$(CH_2CH_2O)_r$—$CH_2$—; and r is an integer ranging from 1-10;

Isothiocyanate Stretchers of the formula shown below may be prepared from isothiocyanatocarboxylic acid chlorides as described in Angew. Chem., 1975, 87(14):517.

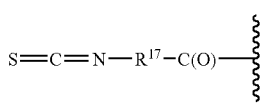

where —$R^{17}$— is as described herein.

As shown in Scheme 5, a Linker can be reacted with an amino group of a Drug Compound 10 to form a Drug-Linker Compound that contains an amide or carbamate group, linking the Drug to the Linker unit. When Reactive Site No. 1 is a carboxylic acid group, as in Linker 29, the coupling reaction can be performed using HATU, DEPC or PyBrop and an appropriate amine base, resulting in a Drug-Linker Compound 30, containing an amide bond between the Drug and the Linker unit. When Reactive Site No. 1 is a carbonate, as in Linker 31, the Linker can be coupled to the Drug using HOBt in a mixture of DMF/pyridine to provide a Drug-Linker Compound 32, containing a carbamate bond between the Drug unit and the Linker unit.

Alternately, when Reactive Site No. 1 is a good leaving group, such as in Linker 70, the Linker can be coupled with an amine group of a Drug via a nucleophilic substitution process to provide a Drug-Linker Compound having an amine linkage (71) between the Drug unit and the Linker unit.

To prepare a Drug-Linker where the Drug is free acid, the ester bond of Drug-Linker compound 30, 31 or 71 is cleaved. Useful esters, cleavable under acidic conditions include, but not limited to tert-butyl ester. Drug 10a or a Drug-Linker when the Drug is a free acid can be prepared from corresponding tert-butyl esters according to General Procedure I.

Illustrative methods useful for linking a Drug to a Ligand to form a Drug-Linker Compound are depicted in Scheme 5 and are outlined in General Procedures G-H.

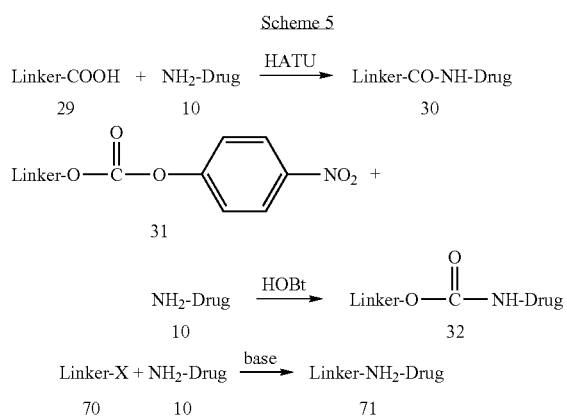

General Procedure G: Amide formation using HATU. A Drug 10 (1.0 eq.) and an N-protected Linker containing a carboxylic acid Reactive site (1.0 eq.) are diluted with a suitable organic solvent, such as dichloromethane, and the resulting solution is treated with HATU (1.5 eq.) and an organic base, preferably pyridine (1.5 eq.). The reaction mixture is allowed to stir under an inert atmosphere, preferably argon, for 6 h, during which time the reaction mixture is monitored using HPLC. The reaction mixture is concentrated and the resulting residue is purified using HPLC to yield the amide 30.

Procedure H: Carbamate formation using HOBt. A mixture of a Linker 31 having a p-nitrophenyl carbonate Reactive site (1.1 eq.) and Drug 10 (1.0 eq.) are diluted with an aprotic organic solvent, such as DMF, to provide a solution having a concentration of 50-100 mM, and the resulting solution is treated with HOBt (2.0 eq.) and placed under an inert atmosphere, preferably argon. The reaction mixture is allowed to stir for 15 min, then an organic base, such as pyridine (1/4 v/v), is added and the reaction progress is monitored using HPLC. The Linker is typically consumed within 16 h. The reaction mixture is then concentrated in vacuo and the resulting residue is purified using, for example, HPLC to yield the carbamate 32.

General Procedure I: Acidic cleavage of tert-butyl ester. A Drug 10 or Linker-Drug-10 (100 mg) is suspended in $CH_2Cl_2$ (4 mL), TFA (2 mL). The reaction mixture is allowed to stir under an inert atmosphere, preferably argon, for 2-4 h, during which time the reaction mixture is monitored using HPLC. The reaction is typically complete in 2 h. The reaction mixture is diluted with toluene (20 mL), concentrated in vacuo. The residue is co-evaporated with toluene (2×10 mL) and dried in vacuum. Product is purified by preparative RP-HPLC if necessary to yield Drug 10a or Linker-Drug-10a.

An alternate method of preparing Drug-Linker Compounds is outlined in Scheme 6. Using the method of Scheme 6, the Drug is attached to a partial Linker unit (19a, for example), which does not have a Stretcher unit attached. This provides intermediate 35, which has an Amino Acid unit having an Fmoc-protected N-terminus. The Fmoc group is then removed and the resulting amine intermediate 36 is then attached to a Stretcher unit via a coupling reaction catalyzed using PyBrop or DEPC. The construction of Drug-Linker Compounds containing either a bromoacetamide Stretcher 37 or a PEG maleimide Stretcher 38 is illustrated in Scheme 6.

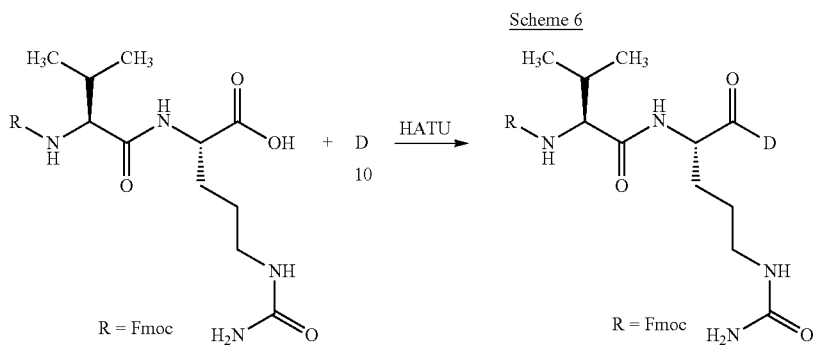

-continued

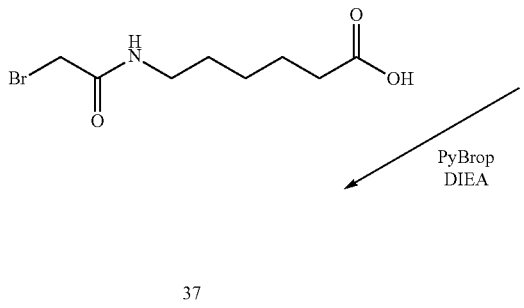

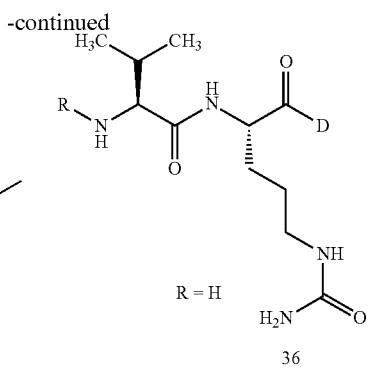

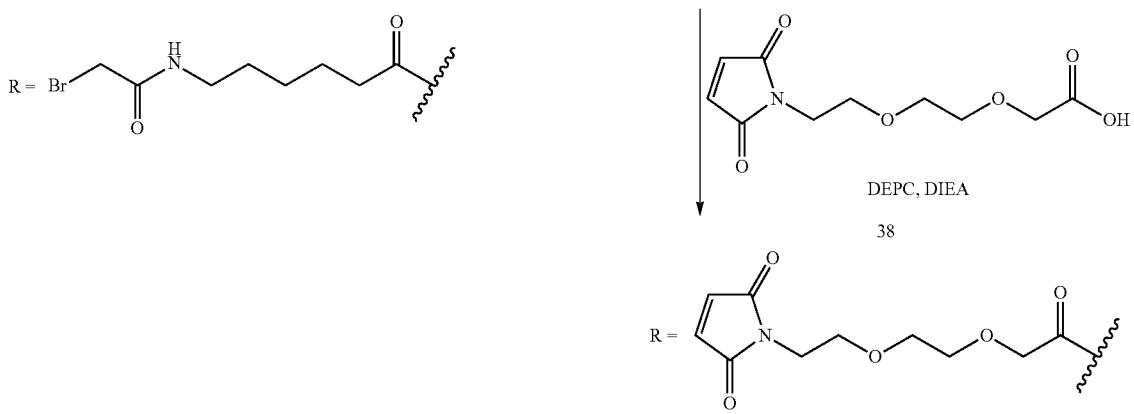

In the Conjugate Compounds, the drug loading is represented by p, the average number of drugs per Ligand unit (e.g., an antibody) in a molecule of Formula Ia. For an antibody, Drug loading may range from 1 to 20 drugs (D) per antibody (Ab or mAb). Compositions of Formula Ia include collections of antibodies conjugated with a range of drugs, from 1 to 20. The average number of drugs per Ligand unit from conjugation reactions may be characterized by conventional means such as UV/visible spectroscopy, mass spectrometry, ELISA assay, and HPLC. The quantitative distribution of Conjugate Compounds in terms of p may also be determined. In some instances, separation, purification, and characterization of homogeneous Conjugate Compounds, where p is a certain value, from Conjugate Compounds with other drug loadings may be achieved by means such as reverse phase HPLC or electrophoresis.

For some Conjugate Compounds, p may be limited by the number of attachment sites on the Ligand. For example, where the attachment is a cysteine thiol, an antibody may have only one or several cysteine thiol groups, or may have only one or several sufficiently reactive thiol groups through which a linker may be attached.

Typically, fewer than the theoretical maximum of drug moieties are conjugated to a Ligand during a conjugation reaction. An antibody may contain, for example, many lysine residues that do not react with the drug-linker intermediate or linker reagent. Only the most reactive lysine groups may react with an amine-reactive linker reagent. Generally, antibodies do not contain many, if any, free and reactive cysteine thiol groups which may be linked to a drug moiety. Most cysteine thiol residues in the antibodies of the compounds of the invention exist as disulfide bridges and must be reduced with a reducing agent such as dithiothreitol (DTT). Additionally, the antibody must be subjected to denaturing conditions to reveal reactive nucleophilic groups such as lysine or cysteine. The loading (drug/antibody ratio) of an antibody drug conjugate may be controlled in several different manners, including: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate, or linker reagent followed by drug moiety reagent, then the resulting product is a mixture of compounds with a distribution of one or more drug moieties attached to an antibody. The average number of drugs per antibody may be calculated from the mixture by dual ELISA antibody assay, specific for antibody and specific for the drug. Individual molecules may be identified in the mixture by mass spectroscopy, and separated by HPLC, e.g., hydrophobic interaction chromatography ("Effect of drug loading on the pharmacology, pharmacokinetics, and toxicity of an anti-CD30 antibody-drug conjugate", Hamblett, K. J., et al, Abstract No. 624, American Association for Cancer Research; 2004 Annual Meeting, Mar. 27-31, 2004, Proceedings of the AACR, Volume 45, March 2004; "Controlling the Location of Drug Attachment in Antibody-Drug Conjugates", Alley, S. C., et al, Abstract No. 627, American Association for Cancer Research; 2004 Annual Meeting, Mar. 27-31, 2004, Proceedings of the AACR, Volume 45, March 2004; Hamblett et al., 2004, Clin Cancer Res. 10(20):7063-70). Thus, a homogeneous ADC with a single loading value may be isolated from the conjugation mixture by electrophoresis or chromatography.

Scheme 7 illustrates methodology useful for making Conjugate Compounds having about 2 to about 4 drugs per Ligand, where Ligand includes an antibody.

Scheme 7

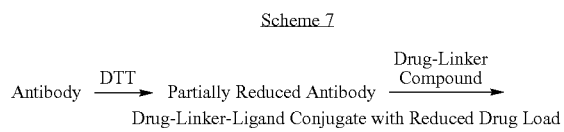

Reduction and Conjugation of Drug-Linker to a partially reduced antibody is described in PCT/US03/24209, incorporated in its entirety herein by reference, and PCT/US05/07239. Other methods of synthesizing Conjugate Compounds and elements thereof are disclosed in U.S. Publication No. 2005-0238649, incorporated in its entirety herein by reference.

Activity Assays for Conjugate Compounds and Drug Compounds

Transgenic animals and cell lines are particularly useful in screening Conjugate Compounds that have potential as prophylactic or therapeutic treatments of diseases or disorders involving overexpression of proteins. Screening for a useful Conjugate Compounds may involve administering a candidate Conjugate Compound(s) over a range of doses to the transgenic animal, and assaying at various time points for the effect(s) of the Conjugate Compound(s) on the disease or disorder being evaluated. Alternatively, or additionally, the drug can be administered prior to or simultaneously with exposure to an inducer of the disease, if applicable. Candidate Conjugate Compounds may be screened serially and individually, or in parallel under medium or high-throughput screening format. The rate at which Conjugate Compounds may be screened for utility for prophylactic or therapeutic treatments of diseases or disorders is limited only by the rate of synthesis or screening methodology, including detecting/measuring/analysis of data.

One embodiment is a screening method comprising (a) transplanting cells from a stable cancer cell line (e.g., a renal cell cancer cell line) into a non-human animal, (b) administering a Conjugate Compound candidate to the non-human animal and (c) determining the ability of the candidate to inhibit the formation of tumors from the transplanted cell line.

Another embodiment is a screening method comprising (a) contacting cells from a stable Hodgkin's disease cell line with a Conjugate Compound candidate and (b) evaluating the ability of the candidate to block ligand activation of CD40.

Another embodiment is a screening method comprising (a) contacting cells from a stable Hodgkin's disease cell line with a Conjugate Compound candidate and (b) evaluating the ability of the candidate to induce cell death. In one embodiment the ability of the candidate to induce apoptosis is evaluated.

One embodiment is a screening method comprising (a) transplanting cells from a stable cancer cell line into a non-human animal, (b) administering a Conjugate Compound candidate to the non-human animal, and (c) determining the ability of the candidate to inhibit the formation of tumors from the transplanted cell line.

Another embodiment is a screening method comprising (a) contacting cells from a stable cancer cell line with a Conjugate Compound candidate and (b) evaluating the ability of the candidate to block ligand activation of a target molecule.

Another embodiment is a screening method comprising (a) contacting cells from a stable cancer cell line with a Conjugate Compound candidate and (b) evaluating the ability of the candidate to induce cell death. In one embodiment the ability of the candidate to induce apoptosis is evaluated.

In one embodiment, candidate Conjugate Compounds are screened by being administered to the transgenic animal over a range of doses, and evaluating the animal's physiological response to the compounds over time. Administration may be oral, or by suitable injection, depending on the chemical nature of the compound being evaluated. In some cases, it may be appropriate to administer the compound in conjunction with co-factors that would enhance the efficacy of the compound. If cell lines derived from the subject transgenic animals are used to screen for compounds useful in treating various disorders, the test compounds are added to the cell culture medium at an appropriate time, and the cellular response to the compound is evaluated over time using the appropriate biochemical and/or histological assays. In some cases, it may be appropriate to apply the compound of interest to the culture medium in conjunction with co-factors that would enhance the efficacy of the compound.

Thus, provided herein are assays for identifying Conjugate Compounds which specifically target and bind a target protein, the presence of which is correlated with abnormal cellular function, and in the pathogenesis of cellular proliferation and/or differentiation that is causally related to the development of tumors.

To identify growth inhibitory compounds that specifically target an antigen of interest, one may screen for compounds which inhibit the growth of cancer cells overexpressing antigen of interest derived from transgenic animals. In some embodiments, the assay described in U.S. Pat. No. 5,677,171 can be performed. According to this assay, cancer cells overexpressing the antigen of interest are grown in a 1:1 mixture of F12 and DMEM medium supplemented with 10% fetal bovine serum, glutamine and penicillin streptomycin. The cells are plated at 20,000 cells in a 35 mm cell culture dish (2 mls/35 mm dish) and the test compound is added at various concentrations. After six days, the number of cells, compared to untreated cells is counted using an electronic COULTER® cell counter. Those compounds which inhibit cell growth by about 20-100% or about 50-100% may be selected as growth inhibitory compounds.

To select for compounds which induce cell death, loss of membrane integrity as indicated by, e.g., PI, trypan blue or 7AAD uptake may be assessed relative to control. The PI uptake assay uses cells isolated from the tumor tissue of interest of a transgenic animal. According to this assay, the cells are cultured in Dulbecco's Modified Eagle Medium (D-MEM):Ham's F-12 (50:50) supplemented with 10% heat-inactivated FBS (Hyclone) and 2 mM L-glutamine. Thus, the assay is performed in the absence of complement and immune effector cells. The cells are seeded at a density of $3 \times 10^6$ per dish in 100×20 mm dishes and allowed to attach overnight. The medium is then removed and replaced with fresh medium alone or medium containing various concentrations of the compound. The cells are incubated for a 3-day time period. Following each treatment, monolayers are washed with PBS and detached by trypsinization. Cells are then centrifuged at 1200 rpm for 5 minutes at 4° C., the pellet resuspended in 3 ml cold $Ca^{2+}$ binding buffer (10 mM Hepes, pH 7.4, 140 mM NaCl, 2.5 mM $CaCl_2$) and aliquoted into 35 mm strainer-capped 12×75 mm tubes (1 ml per tube, 3 tubes per treatment group) for removal of cell clumps. Tubes then receive PI (10 μg/ml). Samples may be analyzed using a FACSCAN® flow cytometer and FACSCONVERT® CellQuest software (Becton Dickinson). Those compounds which induce statistically significant levels of cell death as determined by PI uptake may be selected as cell death-inducing compounds.

In order to select for compounds which induce apoptosis, an annexin binding assay using cells established from the tumor tissue of interest of the transgenic animal is performed.

The cells are cultured and seeded in dishes as discussed in the preceding paragraph. The medium is then removed and replaced with fresh medium alone or medium containing 10 µg/ml of the Conjugate Compound. Following a three-day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g., annexin V-FITC) (1 µg/ml). Samples may be analyzed using a FACSCAN® flow cytometer and FACSCONVERT® CellQuest software (Becton Dickinson). Those compounds which induce statistically significant levels of annexin binding relative to control are selected as apoptosis-inducing compounds.

Generally, the cytotoxic or cytostatic activity of a Conjugate Compound is measured by: exposing mammalian cells having receptor proteins to the Ligand (e.g., an antibody) of the Conjugate Compound in a cell culture medium; culturing the cells for a period from about 6 hours to about 5 days; and measuring cell viability. Cell-based in vitro assays were used to measure viability (proliferation), cytotoxicity, and induction of apoptosis (caspase activation) by the Conjugate Compound(s).

The in vitro potency of Conjugate Compounds can be measured by a cell proliferation assay. The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713 and 5,700, 670). This cell proliferation assay determines the number of viable cells in culture based on quantitation of the ATP present, an indicator of metabolically active cells (see, e.g., Crouch et al., 1993, J. Immunol. Meth. 160:81-88; U.S. Pat. No. 6,602,677). The CellTiter-Glo® Assay can be conducted in 96 well format, making it amenable to automated high-throughput screening (HTS) (see, e.g., Cree et al., 1995, AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with the Conjugate Compound, or they may be treated and separated from Conjugate Compound. Generally, cells treated briefly, i.e., 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g., 96 or 384 well format. Data can be recorded by luminometer or CCD camera imaging device. The luminescence output is presented as relative light units (RLU), measured over time.

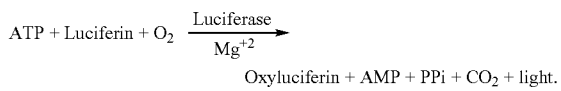

Pharmaceutical Compositions

Pharmaceutical compositions are provided that comprise a Conjugate Compound or Drug Compound and a pharmaceutically acceptable carrier or vehicle. The compositions are suitable for veterinary or human administration. Also provided is the use of a Conjugate Compound or Drug Compound in the preparation of a medicament.

The present compositions can be in any form that allows for the composition to be administered to a patient. For example, the composition can be in the form of a solid, liquid or gas (aerosol), such as a solution, suspension, emulsion, tablet, pill, pellet, capsule, capsule containing liquid, powder, sustained-release formulation, suppository, sprays, or any other form suitable for use. Other examples of suitable pharmaceutical carriers are described in "Remington's Pharmaceutical Sciences" by E. W. Martin.

Typical routes of administration include, without limitation, parenteral, oral, topical, sublingual, rectal, vaginal, ocular, intra-tumor, and intranasal. Parenteral administration includes subcutaneous injections, intravenous, intramuscular, intrasternal injection or infusion techniques. In one aspect, the compositions are administered parenterally. In yet another aspect, the compositions are administered intravenously.

Pharmaceutical compositions can be formulated so as to allow a Conjugate Compound or Drug Compound to be bioavailable upon administration of the composition to a patient. Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the Conjugate Compound or Drug Compound, the manner of administration, and the composition employed.

In some embodiments, the composition is in the form of a liquid, e.g., an emulsion, solution, solution, elixir or syrup. In a composition for administration by injection, one or more of a surfactant, preservative, wetting agent, dispersing agent, suspending agent, buffer, stabilizer and isotonic agent can be included. The liquid can be useful for oral administration or for delivery by injection.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

When intended for oral administration, the composition is preferably in solid or liquid form, where semi-solid, semi-liquid, suspension and gel forms are included within the forms considered herein as either solid or liquid. When intended for oral administration, a composition can comprise one or more of a sweetening agent, preservatives, dye/colorant and flavor enhancer.

As a solid composition, the composition can be formulated into a powder, granule, compressed tablet, pill, capsule, chewing gum, wafer or the like form. Such a solid composition typically contains one or more inert diluents. In addition, one or more of the following can be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it can contain, in addition to materials of the above type, a liquid carrier such as polyethylene glycol, cyclodextrin or a fatty oil.

The amount of the Conjugate Compound or Drug Compound that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a Conjugate Compound or Drug Compound such that a suitable dosage will be obtained. Typically, this amount is at least about 0.01% of a Conjugate Compound or Drug Compound by weight of the composition. When intended for oral administration, this amount can be varied to range from about 0.1% to about 80% by weight of the composition. In one aspect, oral compositions can comprise from about 4% to about 50% of a Conjugate Compound and/or Drug Compound by weight of the composition. In yet another aspect, present compositions are prepared so that a parenteral dosage unit contains from at least about 0.01% to about 2% or more by weight of the Conjugate Compound or Drug Compound.

For intravenous administration, the composition can comprise from about 0.01 to about 100 mg of a Conjugate Compound or Drug Compound per kg of the animal's body weight. In one aspect, the composition can include from about 1 to about 100 mg of a Conjugate Compound or Drug Compound per kg of the animal's body weight. In another aspect, the amount administered will be in the range from about 0.1 to about 25 mg/kg of body weight of the Conjugate Compound or Drug Compound.

Generally, the dosage of a Conjugate Compound or Drug Compound administered to a patient is typically about 0.01 mg/kg to about 2000 mg/kg of the animal's body weight. In one aspect, the dosage administered to a patient is between about 0.01 mg/kg to about 20 mg/kg of the animal's body weight. In another aspect, the dosage administered to a patient is between about 0.1 mg/kg and about 250 mg/kg of the animal's body weight. In yet another aspect, the dosage administered to a patient is between about 0.1 mg/kg and about 20 mg/kg of the animal's body weight. In yet another aspect the dosage administered is between about 0.1 mg/kg to about 15 mg/kg of the animal's body weight, in yet another aspect, the dosage administered is between about 1 mg/kg to about 15 mg/kg of the animal's body weight; and in yet another aspect, the dosage administered is between about 1 mg/kg to about 10 mg/kg of the animal's body weight.

The Conjugate Compound or Drug Compound can be administered by any convenient route, for example by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a Conjugate Compound or Drug Compound.

In certain embodiments, more than one Conjugate Compound or Drug Compound is administered to a patient.

In specific embodiments, it can be desirable to administer one or more a Conjugate Compound or Drug Compound locally to the area in need of treatment. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, nonporous, or gelatinous material, including membranes, such as sialastic membranes, or fibers. In one embodiment, administration can be by direct injection at the site (or former site) of a cancer, tumor or neoplastic or pre-neoplastic tissue. In another embodiment, administration can be by direct injection at the site (or former site) of a manifestation of an autoimmune disease.

In certain embodiments, it can be desirable to introduce one or more a Conjugate Compound or Drug Compound into the central nervous system by any suitable route, including intraventricular and intrathecal injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

In yet another embodiment, the Conjugate Compound or Drug Compound can be delivered in a controlled release system, such as but not limited to, a pump or various polymeric materials can be used. In yet another embodiment, a controlled-release system can be placed in proximity of the target of the Conjugate Compound or Drug Compound, e.g., the brain, thus requiring only a fraction of the systemic dose (see, e.g., Goodson, in Medical Applications of Controlled Release, supra, vol. 2, pp. 115-138 (1984)). Other controlled-release systems discussed in the review by Langer (Science 249:1527-1533 (1990)) can be used.

The term "carrier" refers to a diluent, adjuvant or excipient, with which a Conjugate Compound or Drug Compound is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a patient, the Conjugate Compound or Drug Compound and pharmaceutically acceptable carriers are sterile. Water is an exemplary carrier when the Conjugate Compound or Drug Compound is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

In an embodiment, the Conjugate Compound or Drug Compound are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where a Conjugate Compound or Drug Compound is to be administered by infusion, it can be dispensed, for example, with an infusion bottle containing sterile pharmaceutical grade water or saline. Where the Conjugate Compound or Drug Compound is administered by injection, an ampoule of sterile water for injection or saline can be provided so that the ingredients can be mixed prior to administration.

Compositions for oral delivery can be in the form of tablets, lozenges, aqueous or oily suspensions, granules, powders, emulsions, capsules, syrups, or elixirs, for example. Orally administered compositions can contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compounds. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used.

The compositions can be intended for topical administration, in which case the carrier may be in the form of a solution, emulsion, ointment or gel base. If intended for transdermal administration, the composition can be in the form of a transdermal patch or an iontophoresis device. Topical formulations can comprise a concentration of a Conjugate Compound or Drug Compound of from about 0.05% to about 50% w/v (weight per unit volume of composition), in another aspect, from 0.1% to 10% w/v.

The composition can be intended for rectal administration, in the form, e.g., of a suppository which will melt in the rectum and release the Conjugate Compound or Drug Compound.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can consist of gaseous dosage units, e.g., it can be in the form of an aerosol. The term aerosol is used to denote a variety of systems ranging from those of colloidal nature to systems consisting of pressurized packages. Delivery can be by a liquefied or compressed gas or by a suitable pump system that dispenses the active ingredients.

The Conjugate Compound or Drug Compound are useful for treating cancer, an autoimmune disease, an infectious disease or other disease or disorder in a patient.

In some embodiments, the Conjugate Compounds and Drug Compounds are useful for inhibiting the multiplication of a tumor cell or cancer cell, causing apoptosis in a tumor or cancer cell, or for treating cancer in a patient. The Conjugate Compounds and Drug Compounds can be used accordingly in a variety of settings for the treatment of animal cancers. The Conjugate Compounds can be used to deliver a Drug or Drug unit to a tumor cell or cancer cell. Without being bound by theory, in one embodiment, the Ligand unit of a Conjugate Compound binds to or associates with a cancer-cell or a tumor-cell-associated antigen, and the Conjugate Compound can be taken up inside a tumor cell or cancer cell through receptor-mediated endocytosis. The antigen can be attached to a tumor cell or cancer cell or can be an extracellular matrix protein associated with the tumor cell or cancer cell. Once inside the cell, one or more specific peptide sequences within the Linker unit are hydrolytically cleaved by one or more tumor-cell or cancer-cell-associated proteases, resulting in release of a Drug, a Drug-Linker Compound or a Drug-Linker fragment (which may include a portion of the Ligand unit). The released Drug, Drug-Linker Compound, Drug-Linker fragment is then free to migrate within the cell and induce cytotoxic or cytostatic activities. In an alternative embodiment, the Drug or Drug unit is cleaved from the Conjugate Compound outside the tumor cell or cancer cell, and the Drug, Drug-Linker Compound or Drug-Linker fragment subsequently penetrates the cell.

In one embodiment, the Ligand unit binds to the tumor cell or cancer cell.

In another embodiment, the Ligand unit binds to a tumor cell or cancer cell antigen which is on the surface of the tumor cell or cancer cell.

In another embodiment, the Ligand unit binds to a tumor cell or cancer cell antigen which is an extracellular matrix protein associated with the tumor cell or cancer cell.

The specificity of the Ligand unit for a particular tumor cell or cancer cell can be important for determining those tumors or cancers that are most effectively treated. For example, Conjugate Compounds having a BR96 Ligand unit can be useful for treating antigen positive carcinomas including those of the liver, lung, breast, colon, ovaries, rectum, and pancreas. Conjugate Compounds having an anti-CD30, anti-CD33, anti-CD19, or an anti-CD40 Ligand unit can be useful for treating hematologic malignancies.

Other particular types of cancers that can be treated with the Conjugate Compound(s) or Drug Compound(s) include, but are not limited to, those disclosed in Table 1.

TABLE 1

| Solid tumors, including but not limited to: |
| --- |
| sarcoma |
| fibrosarcoma |
| myxosarcoma |
| liposarcoma |
| chondrosarcoma |
| osteogenic sarcoma |

TABLE 1-continued chordoma
angiosarcoma
endotheliosarcoma
lymphangiosarcoma
lymphangioendotheliosarcoma
synovioma
mesothelioma
Ewing's tumor
leiomyosarcoma
rhabdomyosarcoma
colon cancer
colorectal cancer
kidney cancer
pancreatic cancer
bone cancer
breast cancer
ovarian cancer
prostate cancer
esophogeal cancer
stomach cancer (e.g., gastrointestinal cancer)
oral cancer
nasal cancer
throat cancer
squamous cell carcinoma (e.g., of the lung)
basal cell carcinoma
adenocarcinoma (e.g., of the lung)
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
cervical cancer
uterine cancer
testicular cancer
small cell lung carcinoma
bladder carcinoma
lung cancer
non-small cell lung cancer
epithelial carcinoma
glioma
glioblastoma multiforme
astrocytoma
medulloblastoma
craniopharyngioma
ependymoma
pinealoma
hemangioblastoma
acoustic neuroma
oligodendroglioma
meningioma
skin cancer
melanoma
neuroblastoma
retinoblastoma
blood-borne cancers, including but not limited to:

acute lymphoblastic leukemia "ALL"
acute lymphoblastic B-cell leukemia
acute lymphoblastic T-cell leukemia
acute myeloblastic leukemia "AML"
acute promyelocytic leukemia "APL"
acute monoblastic leukemia
acute erythroleukemic leukemia
acute megakaryoblastic leukemia
acute myelomonocytic leukemia
acute nonlymphocytic leukemia
acute undifferentiated leukemia
chronic myelocytic leukemia "CML"
chronic lymphocytic leukemia "CLL"
hairy cell leukemia
multiple myeloma TABLE 1-continued acute and chronic leukemias:

lymphoblastic
myelogenous
lymphocytic
myelocytic leukemias
Lymphomas:

Hodgkin's disease
non-Hodgkin's Lymphoma
Multiple myeloma
Waldenström's macroglobulinemia
Heavy chain disease
Polycythemia vera
Other cancers:

Peritoneal cancer
Hepatocellular cancer
Hepatoma
Salivary cancer
Vulval cancer
Thyroid
Penile cancer
Anal cancer
Head and neck cancer
Renal cell carcinoma
Acute anaplastic large cell carcinoma
Cutaneous anaplastic large cell carcinoma Cancers, including, but not limited to, a tumor, metastasis, or other disease or disorder characterized by uncontrolled cell growth, can be treated or prevented by administration of a Conjugate Compound or Drug Compound.

In other embodiments, methods for treating or preventing cancer are provided, including administering to a patient in need thereof an effective amount of a Conjugate Compound or Drug Compound and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Conjugate Compound or Drug Compound can be administered to a patient that has also undergone surgery as treatment for the cancer.

In one embodiment, the additional method of treatment is radiation therapy.

In a specific embodiment, the Conjugate Compound is administered concurrently with the chemotherapeutic agent or with radiation therapy. In another specific embodiment, the chemotherapeutic agent or radiation therapy is administered prior or subsequent to administration of a Conjugate Compound, in one aspect at least an hour, five hours, 12 hours, a day, a week, a month, in further aspects several months (e.g., up to three months), prior or subsequent to administration of a Conjugate Compound.

A chemotherapeutic agent can be administered over a series of sessions. Any one or a combination of the chemotherapeutic agents listed in Table 2 can be administered. With respect to radiation, any radiation therapy protocol can be used depending upon the type of cancer to be treated. For example, but not by way of limitation, x-ray radiation can be administered; in particular, high-energy megavoltage (radiation of greater that 1 MeV energy) can be used for deep tumors, and electron beam and orthovoltage x-ray radiation can be used for skin cancers. Gamma-ray emitting radioisotopes, such as radioactive isotopes of radium, cobalt and other elements, can also be administered.

Additionally, methods of treatment of cancer with an Conjugate Compound or Drug Compound are provided as an alternative to chemotherapy or radiation therapy where the chemotherapy or the radiation therapy has proven or can prove too toxic, e.g., results in unacceptable or unbearable side effects, for the subject being treated. The animal being treated can, optionally, be treated with another cancer treatment such as surgery, radiation therapy or chemotherapy, depending on which treatment is found to be acceptable or bearable.

The Conjugate Compound or Drug Compounds can also be used in an in vitro or ex vivo fashion, such as for the treatment of certain cancers, including, but not limited to leukemias and lymphomas, such treatment involving autologous stem cell transplants. This can involve a multi-step process in which the animal's autologous hematopoietic stem cells are harvested and purged of all cancer cells, the animal's remaining bone-marrow cell population is then eradicated via the administration of a high dose of an Conjugate Compound or Drug Compound with or without accompanying high dose radiation therapy, and the stem cell graft is infused back into the animal. Supportive care is then provided while bone marrow function is restored and the animal recovers.

Methods for treating cancer further include administering to a patient in need thereof an effective amount of a Conjugate Compound and another therapeutic agent that is an anti-cancer agent are disclosed. Suitable anticancer agents include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, cytoxan, etoposide, 5-fluorouracil, BCNU, irinotecan, camptothecins, bleomycin, doxorubicin, idarubicin, daunorubicin, actinomycin D, dactinomycin, plicamycin, mitoxantrone, asparaginase, vinblastine, vincristine, vindesine, vinorelbine, paclitaxel, and docetaxel.

Other examples of chemotherapeutic agents include alkylating agents such as thiotepa and CYTOXAN® cyclosphosphamide; alkyl sulfonates such as busulfan, treosulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; triazines such as decarbazine; nitrosureas such as carmustine, chlorozotocin, fotemustine, lomustine, nimustine, and ranimnustine; epipodophyllins, such as etoposide, teniposide, topotecan, 9-aminocamptothecin, camptothecin orcrisnatol; bisphosphonates, such as clodronate; antibiotics such as the enediyne antibiotics (e.g., calicheamicin, especially calicheamicin gamma1I and calicheamicin omega1 (see, e.g., Agnew, Chem. Intl. Ed. Engl., 33:183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins (e.g., A2 and B2), cactinomycin, carabicin, caminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; photodynamic therapies, such as vertoporfin (BPD-MA), phthalocyanine, photosensitizer Pc4, and demethoxy-hypocrellin A (2BA-2-DMHA); folic acid analogues such as denopterin, pteropterin, and trimetrexate; dpurine analogs such as fludarabine, 6-mercaptopurine, thiamiprine, and thioguanine; pyrimidine analogs such as ancitabine, azacitidine, 6-azauridine, carmofur, cytarabine, cytosine arabinoside, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate and trimetrexate; anti-metabolites such as 5-fluorouracil (5-FU) and its prodrugs such as UFT, S-1 and capecitabine, floxuridine, doxifluridine and ratitrexed; and thymidylate synthase inhibitors and glycinamide ribonucleotide formyltransferase inhibitors such as raltitrexed (TOMUDEXRM, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); velcade; revlimid; thalidomide; IMiD3; lovastatin; verapamil; thapsigargin; 1-methyl-4-phenylpyridinium; cell cycle inhibitors such as staurosporine; novantrone; edatrexate; daunomycin; mtoxantrone; aminopterin; xeloda; ibandronate; topoisomerase inhibitor RFS 2000; difluoromethylornithine (DMFO); vitamin D3 analogs, such as EB 1089, CB 1093 and KH 1060; retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATINTM) combined with 5-FU and leucovorin.

Anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, megastrol, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, bicalutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

Examples of antibodies available for the treatment of cancer include, but are not limited to, humanized anti HER2 monoclonal antibody, HERCEPTIN® (trastuzumab; Genentech); RITUXAN® (rituximab; Genentech) which is a chimeric anti CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine IgG2a antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; Campath I/H (Leukosite, MA) which is a humanized IgG1 antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens (exemplary cancers are indicated in parentheses): CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific membrane antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti transferrin receptor (carcinomas), p97 (melanoma), MUC1-KLH (breast cancer), CEA (colorectal), gp100 (melanoma), MART1 (melanoma), prostate specific antigen (PSA) (prostate), IL-2 receptor (T-cell leukemia and lymphomas), CD20 (non Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail et al., 1993, Science 261:212-215), BR64 (Trail et al., 1997, Cancer Research 57:100-105), mAbs against the CD40 antigen, such as S2C6 mAb (Francisco et al., 2000, Cancer Res. 60:3225-3231) and chimeric and humanized variants thereof, mabs against the cD33 antigen; mabs against the EphA2 antigen; mAbs against the CD70 antigen, such as 1F6 mAb and 2F2 mAb and chimeric and humanized variants thereof, and mAbs against the CD30 antigen, such as AC10 (Bowen et al., 1993, J. Immunol. 151:5896-5906; Wahl et al., 2002, Cancer Res. 62(13):3736-42) and chimeric and humanized variants thereof. Many other internalizing antibodies that bind to tumor associated antigens can be used and have been reviewed (see, e.g., Franke et al., 2000, Cancer Biother. Radiopharm. 15:459 76; Murray, 2000, Semin. Oncol. 27:64 70; Breitling et al., Recombinant Antibodies, John Wiley, and Sons, New York, 1998).

The Conjugate Compounds and Drug Compounds are useful for killing or inhibiting the replication of a cell that produces an autoimmune disease or for treating an autoimmune disease. The Conjugate Compounds and Drug Compounds can be used accordingly in a variety of settings for the treatment of an autoimmune disease in a patient. The Conjugate Compounds can be used to deliver a Drug to a target cell. Without being bound by theory, in one embodiment, the Conjugate Compound associates with an antigen on the surface of a target cell, and the Conjugate Compound is then taken up inside a target-cell through receptor-mediated endocytosis. Once inside the cell, one or more specific peptide sequences within the Linker unit are enzymatically or hydrolytically cleaved, resulting in release of an intracellular metabolite, such as a Drug, a Drug-Linker Compound or a Drug-Linker fragment. The released intracellular metabolite is then free to migrate in the cytosol and induce cytotoxic or cytostatic activities. In an alternative embodiment, the Drug is cleaved from the Conjugate Compound outside the target cell, and the Drug subsequently penetrates the cell.

In one embodiment, the Ligand unit binds to an autoimmune antigen. In one aspect, the antigen is on the surface of a cell involved in an autoimmune condition.

In another embodiment, the Ligand unit binds to an autoimmune antigen which is on the surface of a cell.

In one embodiment, the Ligand binds to activated lymphocytes that are associated with the autoimmune disease state.

In a further embodiment, the Conjugate Compounds and Drug Compounds kill or inhibit the multiplication of cells that produce an autoimmune antibody associated with a particular autoimmune disease.

Particular types of autoimmune diseases that can be treated with the Conjugate Compounds include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); and those disclosed in Table 2.

TABLE 2

Active Chronic Hepatitis
Addison's Disease
Allergic Alveolitis
Allergic Reaction
Allergic Rhinitis
Alport's Syndrome
Anaphlaxis
Ankylosing Spondylitis
Anti-phosholipid Syndrome
Arthritis
Ascariasis
Aspergillosis
Atopic Allergy
Atropic Dermatitis
Atropic Rhinitis
Behcet's Disease
Bird-Fancier's Lung
Bronchial Asthma
Caplan's Syndrome
Cardiomyopathy
Celiac Disease
Chagas' Disease
Chronic Glomerulonephritis
Cogan's Syndrome
Cold Agglutinin Disease
Congenital Rubella Infection
CREST Syndrome
Crohn's Disease
Cryoglobulinemia
Cushing's Syndrome
Dermatomyositis
Discoid Lupus
Dressler's Syndrome
Eaton-Lambert Syndrome
Echovirus Infection
Encephalomyelitis
Endocrine opthalmopathy
Epstein-Barr Virus Infection
Equine Heaves
Erythematosis
Evan's Syndrome
Felty's Syndrome
Fibromyalgia
Fuch's Cyclitis
Gastric Atrophy
Gastrointestinal Allergy
Giant Cell Arteritis
Glomerulonephritis
Goodpasture's Syndrome
Graft v. Host Disease
Graves' Disease
Guillain-Barre Disease
Hashimoto's Thyroiditis
Hemolytic Anemia
Henoch-Schonlein Purpura
Idiopathic Adrenal Atrophy
Idiopathic Pulmonary Fibritis
IgA Nephropathy
Inflammatory Bowel Diseases
Insulin-dependent Diabetes Mellitus
Juvenile Arthritis
Juvenile Diabetes Mellitus (Type I)
Lambert-Eaton Syndrome
Laminitis
Lichen Planus
Lupoid Hepatitis
Lupus
Lymphopenia
Meniere's Disease TABLE 2-continued Mixed Connective Tissue Disease
Multiple Sclerosis
Myasthenia Gravis
Pernicious Anemia
Polyglandular Syndromes
Presenile Dementia
Primary Agammaglobulinemia
Primary Biliary Cirrhosis
Psoriasis
Psoriatic Arthritis
Raynauds Phenomenon
Recurrent Abortion
Reiter's Syndrome
Rheumatic Fever
Rheumatoid Arthritis
Sampter's Syndrome
Schistosomiasis
Schmidt's Syndrome
Scleroderma
Shulman's Syndrome
Sjorgen's Syndrome
Stiff-Man Syndrome
Sympathetic Ophthalmia
Systemic Lupus Erythematosis
Takayasu's Arteritis
Temporal Arteritis
Thyroiditis
Thrombocytopenia
Thyrotoxicosis
Toxic Epidermal Necrolysis
Type B Insulin Resistance
Type I Diabetes Mellitus
Ulcerative Colitis
Uveitis
Vitiligo
Waldenstrom's Macroglobulemia
Wegener's Granulomatosis Methods for treating an autoimmune disease are also disclosed including administering to a patient in need thereof an effective amount of a Conjugate Compound or Drug Compound and another therapeutic agent known for the treatment of an autoimmune disease. In one embodiment, the anti-autoimmune disease agent includes, but is not limited to, agents listed in Table 3.

TABLE 3 cyclosporine
cyclosporine A
mycophenylate mofetil
sirolimus
tacrolimus
enanercept
prednisone
azathioprine
methotrexate cyclophosphamide
prednisone
aminocaproic acid
chloroquine
hydroxychloroquine
hydrocortisone
dexamethasone
chlorambucil
DHEA
danazol
bromocriptine
meloxicam
infliximab The Conjugate Compounds are useful for killing or inhibiting the multiplication of a cell that produces an infectious disease or for treating an infectious disease. The Conjugate Compounds can be used accordingly in a variety of settings for the treatment of an infectious disease in a patient. The Conjugate Compounds can be used to deliver a Drug to a target cell. In one embodiment, the Ligand unit binds to the infectious disease cell.

In one embodiment, the Conjugates kill or inhibit the multiplication of cells that produce a particular infectious disease.

Particular types of infectious diseases that can be treated with the Conjugate Compounds and Drug Compounds include, but are not limited to, those disclosed in Table 4.

TABLE 4

Bacterial Diseases:

Diphtheria
Pertussis
Occult Bacteremia
Urinary Tract Infection
Gastroenteritis
Cellulitis
Epiglottitis
Tracheitis
Adenoid Hypertrophy
Retropharyngeal Abcess
Impetigo
Ecthyma
Pneumonia
Endocarditis
Septic Arthritis
Pneumococcal
Peritonitis
Bactermia
Meningitis
Acute Purulent Meningitis
Urethritis
Cervicitis
Proctitis
Pharyngitis
Salpingitis
Epididymitis
Gonorrhea
Syphilis
Listeriosis
Anthrax
Nocardiosis
Salmonella
Typhoid Fever
Dysentery
Conjunctivitis
Sinusitis
Brucellosis
Tullaremia
Cholera
Bubonic Plague
Tetanus
Necrotizing Enteritis
Actinomycosis
Mixed Anaerobic Infections
Syphilis
Relapsing Fever
Leptospirosis
Lyme Disease
Rat Bite Fever
Tuberculosis
Lymphadenitis
Leprosy
Chlamydia
Chlamydial Pneumonia
Trachoma
Inclusion Conjunctivitis
Systemic Fungal Diseases:

Histoplamosis
Coccidiodomycosis
Blastomycosis
Sporotrichosis
Cryptococcsis
Systemic Candidiasis
Aspergillosis
Mucormycosis TABLE 4-continued Mycetoma
Chromomycosis
Rickettsial Diseases:

Typhus
Rocky Mountain Spotted Fever
Ehrlichiosis
Eastern Tick-Borne Rickettsioses
Rickettsialpox
Q Fever
Bartonellosis
Parasitic Diseases:

Malaria
Babesiosis
African Sleeping Sickness
Chagas' Disease
Leishmaniasis
Dum-Dum Fever
Toxoplasmosis
Meningoencephalitis
Keratitis
Entamebiasis
Giardiasis
Cryptosporidiasis
Isosporiasis
Cyclosporiasis
Microsporidiosis
Ascariasis
Whipworm Infection
Hookworm Infection
Threadworm Infection
Ocular Larva Migrans
Trichinosis
Guinea Worm Disease
Lymphatic Filariasis
Loiasis
River Blindness
Canine Heartworm Infection
Schistosomiasis
Swimmer's Itch
Oriental Lung Fluke
Oriental Liver Fluke
Fascioliasis
Fasciolopsiasis
Opisthorchiasis
Tapeworm Infections
Hydatid Disease
Alveolar Hydatid Disease
Viral Diseases:

Measles
Subacute sclerosing panencephalitis
Common Cold
Mumps
Rubella
Roseola
Fifth Disease
Chickenpox
Respiratory syncytial virus infection
Croup
Bronchiolitis
Infectious Mononucleosis
Poliomyelitis
Herpangina
Hand-Foot-and-Mouth Disease
Bornholm Disease
Genital Herpes
Genital Warts
Aseptic Meningitis
Myocarditis
Pericarditis
Gastroenteritis
Acquired Immunodeficiency Syndrome (AIDS)
Human Immunodeficiency Virus (HIV)
Reye's Syndrome
Kawasaki Syndrome
Influenza
Bronchitis
Viral "Walking" Pneumonia

TABLE 4-continued

Acute Febrile Respiratory Disease
Acute pharyngoconjunctival fever
Epidemic keratoconjunctivitis
Herpes Simplex Virus 1 (HSV-1)
Herpes Simplex Virus 2 (HSV-2)
Shingles
Cytomegalic Inclusion Disease
Rabies
Progressive Multifocal Leukoencephalopathy
Kuru
Fatal Familial Insomnia
Creutzfeldt-Jakob Disease
Gerstmann-Straussler-Scheinker Disease
Tropical Spastic Paraparesis
Western Equine Encephalitis
California Encephalitis
St. Louis Encephalitis
Yellow Fever
Dengue
Lymphocytic choriomeningitis
Lassa Fever
Hemorrhagic Fever
Hantvirus Pulmonary Syndrome
Marburg Virus Infections
Ebola Virus Infections
Smallpox Methods for treating an infectious disease are disclosed including administering to a patient in need thereof a Conjugate Compound and another therapeutic agent that is an anti-infectious disease agent. In one embodiment, the anti-infectious disease agent is, but not limited to, agents listed in Table 5.

TABLE 5

β-Lactam Antibiotics:

Penicillin G
Penicillin V
Cloxacilliin
Dicloxacillin
Methicillin
Nafcillin
Oxacillin
Ampicillin
Amoxicillin
Bacampicillin
Azlocillin
Carbenicillin
Mezlocillin
Piperacillin
Ticarcillin
Aminoglycosides:

Amikacin
Gentamicin
Kanamycin
Neomycin
Netilmicin
Streptomycin
Tobramycin
Macrolides:

Azithromycin
Clarithromycin
Erythromycin
Lincomycin
Clindamycin
Tetracyclines:

Demeclocycline
Doxycycline
Minocycline
Oxytetracycline
Tetracycline

TABLE 5-continued

Quinolones:

Cinoxacin
Nalidixic Acid
Fluoroquinolones:

Ciprofloxacin
Enoxacin
Grepafloxacin
Levofloxacin
Lomefloxacin
Norfloxacin
Ofloxacin
Sparfloxacin
Trovafloxicin
Polypeptides:

Bacitracin
Colistin
Polymyxin B
Sulfonamides:

Sulfisoxazole
Sulfamethoxazole
Sulfadiazine
Sulfamethizole
Sulfacetamide
Miscellaneous Antibacterial Agents:

Trimethoprim
Sulfamethazole
Chloramphenicol
Vancomycin
Metronidazole
Quinupristin
Dalfopristin
Rifampin
Spectinomycin
Nitrofurantoin
Antiviral Agents:
General Antiviral Agents:

Idoxuradine
Vidarabine
Trifluridine
Acyclovir
Famcicyclovir
Pencicyclovir
Valacyclovir
Gancicyclovir
Foscarnet
Ribavirin
Amantadine
Rimantadine
Cidofovir
Antisense Oligonucleotides
Immunoglobulins
Inteferons
Drugs for HIV infection:

Tenofovir
Emtricitabine
Zidovudine
Didanosine
Zalcitabine
Stavudine
Lamivudine
Nevirapine
Delavirdine
Saquinavir
Ritonavir
Indinavir
Nelfinavir The invention is further described in the following examples, which are in not intended to limit the scope of the invention.

EXAMPLE 1

Preparation of 4-Abz-Val-Dil-Dap-Phe-OtBu
(Compound 100)

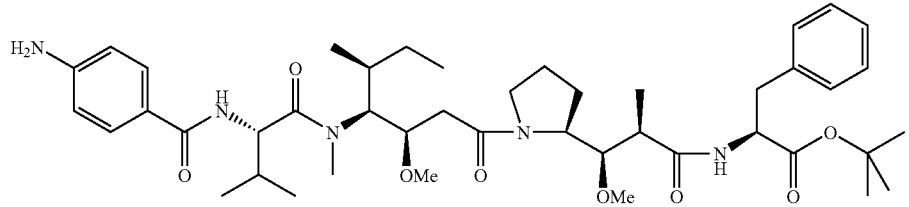

To a room temperature suspension of Val-Dil-OtBu (1.17 g, 2.7 mmol) and Fmoc-4-Abz-OH in anhydrous DMF (5 mL) was added DEPC (0.82 mL, 5.4 mmol) and DIEA (1.88 mL, 10.8 mmol). HPLC analysis indicated complete reaction after 1 h. The reaction mixture was diluted with ethyl acetate (350 mL) and extracted sequentially with 0.1 M HCl (450 mL×2) and H$_2$O (450 mL). The organic phase was concentrated in vacuo and filtered through a small plug of silica gel. Fmoc-4-Abz-Val-Dil-OtBu was isolated by preparatory RP-HPLC, using a Phenomenex C$_{12}$ Synergi Max-RP 80 Å Column (250×50.00 mm). Eluent: linear gradient 10% to 90% MeCN/0.05% TFA (aq) over 20 minutes, then isocratic 90% MeCN/0.05% TFA (aq) for an additional 30 minutes. A total of 1.39 g of pure Fmoc-4-Abz-Val-Dil-OtBu (1.99 mmol, 74% yield) was obtained.

To a room temperature suspension of Fmoc-4-Abz-Val-Dil-OtBu (1.39 g, 1.99 mmol) in anhydrous CH$_2$Cl$_2$ (40 mL) was added TFA (10 mL). HPLC analysis indicated complete reaction after 3.5 h. Volatile organics were evaporated in vacuo. Thus prepared Fmoc-4-Abz-Val-Dil was used in the next step without purification.

Phenylalanine t-butyl ester HCl salt (868 mg, 3 mmol), N-Boc-Dolaproine (668 mg, 1 eq.), DEPC (820 μL, 1.5 eq.), and DIEA (1.2 mL) were diluted with dichloromethane (3 mL). After 2 h at room temperature (about 28 degrees Celcius), the reaction mixture was diluted with dichloromethane (20 mL), and washed successively with saturated aqueous (aq.) NaHCO$_3$ (2×10 mL), saturated aq. NaCl (2×10 mL). The organic layer was separated and concentrated. The resulting residue was re-suspended in ethyl acetate and was purified via flash chromatography in ethyl acetate. The relevant fractions were combined and concentrated to provide the dipeptide as a white solid: 684 mg (46% yield). ES-MS m/z 491.3 [M+H]$^+$.

For selective Boc cleavage in the presence of t-butyl ester, the above dipeptide (500 mg, 1.28 mmol) was diluted with dioxane (2 mL). 4M HCl/dioxane (960 μL, 3 eq.) was added, and the reaction mixture was stirred overnight at room temperature. Almost complete Boc deprotection was observed by RP-HPLC with minimal amount of t-butyl ester cleavage. The mixture was cooled down on an ice bath, and triethylamine (500 μL) was added. After 10 min., the mixture was removed from the cooling bath, diluted with dichloromethane (20 mL), washed successively with saturated aq. NaHCO$_3$ (2×10 mL), saturated aq. NaCl (2×10 mL). The organic layer was concentrated to give a yellow foam: 287 mg (57%). The intermediate was used without further purification.

To a room temperature suspension of Fmoc-4-Abz-Val-Dil (0.96 g, 1.49 mmol) and Dap-Phe-OtBu (0.58 g, 1.49 mmol) in anhydrous CH$_2$Cl$_2$ (20 mL) was added DEPC (0.34 mL, 2.98 mmol) and DIEA (1.04 mL, 5.96 mmol). The reaction mixture was allowed to stir for 84 h, then volatile organics were evaporated in vacuo, and the crude residue diluted with ethyl acetate (200 mL), and extracted with 0.1 M HCl (300 mL×2). The organic phase was concentrated in vacuo and the crude residue was purified by centrifugal TLC using a 0-1-2% MeOH/CH$_2$Cl$_2$ step-gradient, resulting in 0.73 g (0.72 mmol, 48% yield) of Fmoc-4-Abz-Val-Dil-Dap-Phe-OtBu. ES-MS m/z 1016.39 [M+H]$^+$.

Fmoc-4-Abz-Val-Dil-Dap-Phe-OtBu (700 mg, 0.689 mmol) was suspended in anhydrous CH$_2$Cl$_2$ (10 mL), and to it was added diethyl amine (DEA, 5 mL). This mixture was stirred for ~16 h. Volatile organics were evaporated in vacuo. Crude product was partially purified by centrifugal TLC (0-5% gradient: MeOH/CH$_2$Cl$_2$) to remove fmoc-related compounds. The enriched product was purified by preparatory RP-HPLC, using a Phenomenex C$_{12}$ Synergi Max-RP 80A Column (250×50.00 mm). Eluent: linear gradient 10% to 90% MeCN/0.1% formic acid (aq) over 20 minutes, then isocratic 90% MeCN/0.1% formic acid (aq) for an additional 30 minutes. A total of 0.35 g of pure 4-Abz-Val-Dil-Dap-Phe-OtBu (compound 100, 0.44 mmol, 64% yield) was obtained. ES-MS m/z 794.38 [M+H]$^+$; 816.73 [M+Na]$^+$.

EXAMPLE 2

Preparation of MC-4-Abz-Val-Dil-Dap-Phe-OtBu
(Compound 101)

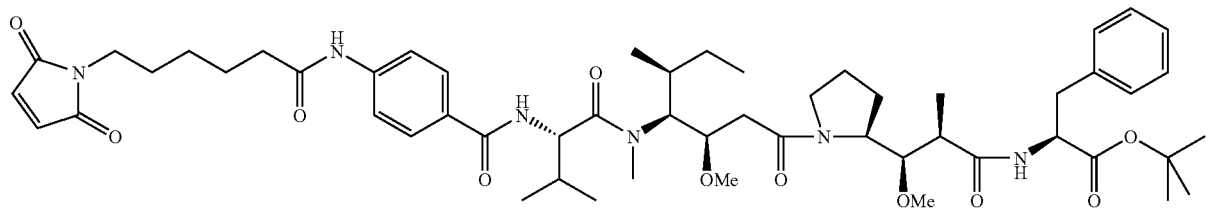

To a room temperature suspension of compound 100 (150 mg, 0.189 mmol) and maleimidocaproic acid (MC-OH, 44 mg, 0.208 mmol, Molecular Biosciences, Inc., Boulder Colo.) in anhydrous CH$_2$Cl$_2$ (10 mL) was added HATU (101 mg, 0.265 mmol, 1.4 eq) and DIEA (0.13 mL, 0.756 mmol). After 16 h, the reaction was not complete, so additional reagents (0.567 mmol of MC-OH; 1.7 mmol of HATU; and 2.84 mmol of DI EA) were added over the following 72 h. Product was isolated by preparatory RP-HPLC, using a Phenomenex C$_{12}$ Synergi Max-RP 80A Column (250×21.20 mm). Eluent: linear gradient 10% to 90% MeCN/0.05% TFA (aq) over 20 minutes, then isocratic 90% MeCN/0.05% TFA (aq) for an additional 30 minutes. MC-4-Abz-Val-Dil-Dap-Phe-OtBu was obtained in 42% yield (78 mg, 0.079 mmol). ES-MS m/z 987.19 [M+H]$^+$; 985.26 [M−H]$^−$.

EXAMPLE 3

Preparation of MC-4-Abz-Val-Dil-Dap-Phe (Compound 102)

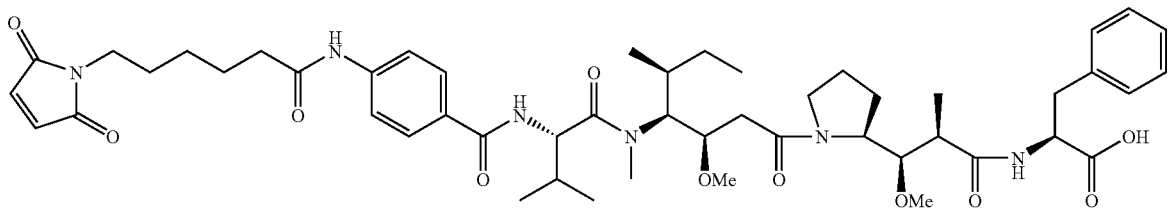

To a room temperature suspension of compound 101 (70 mg, 0.071 mmol) in anhydrous CH$_2$Cl$_2$ (4 mL) was added TFA (2 mL). After 2 h, volatile organics were evaporated in vacuo, resulting in a pure white solid (66 mg, 0.071 mmol) which was used without purification. ES-MS m/z 931.26 [M+H]$^+$; 929.33 [M−H]$^−$.

EXAMPLE 4

Preparation of 4-Abz-Val-Dil-Dap-Phe (Compound 103)

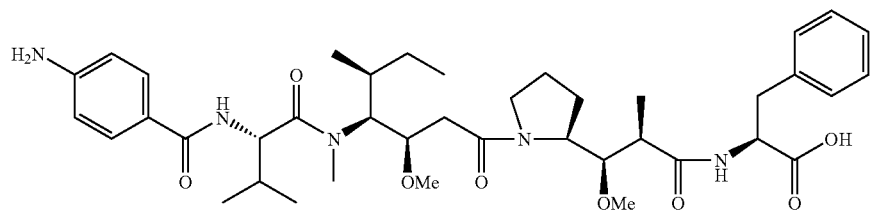

To a room temperature suspension of compound 100 (50 mg, 0.063 mmol) in acetonitrile (20 mL) was added HCl (4 M in dioxane, 5 mL). The reaction was stirred 72 h, and then volatile organics were evaporated in vacuo. Product was obtained as the HCl salt (48 mg, 0.063 mmol). ES-MS m/z 738.37 [M+H]$^+$; 736.50 [M−H]$^−$.

EXAMPLE 5

Preparation of MC-Val-Cit (Compound 104)

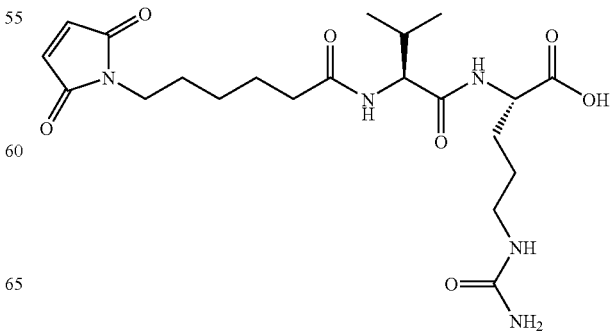

To a room temperature solution of Fmoc-Val-Cit (2.18 g, 4.4 mmol, U.S. Pat. No. 6,214,345 to Firestone et al.) in anhydrous DMF (10 mL) was added DEA (10 mL). The reaction mixture was stirred at ambient temperature for 20 minutes. The reaction mixture was concentrated in vacuo to thick oil, and then was added drop wise to a flask containing diethyl ether (~500 mL) to precipitate the crude product. The white precipitate was collected by filtration and washed with ethyl acetate (2×250 mL). After drying material in vacuo, it was dissolved in DMSO (30 mL), and maleimidocaproic acid-N-hydroxysuccinimide ester (1.42 g, 1.05 eq, Molecular Biosciences, Inc., Boulder Colo.) was added, followed by the addition or DIEA (0.843 mL, 1.1 eq). The reaction mixture was stirred ~6 h, the DMSO solution was concentrated in vacuo to a volume of ~2 mL. Product was purified on a semi-preparative HPLC system (stationary phase: C12, mobile phase: 0.1% TFA/H$_2$O/MeCN) to give 1.19 g (2.55 mmol, 58% yield). ES-MS m/z 468.23 [M+H]$^+$. $^1$H NMR (d$_6$-DMSO) □: 8.15 (d, J=7.2 Hz, 1H), 7.75 (d, J=9.2 Hz, 1 H), 7.00 (s, 1 H), 5.93 (br s, 1 H), 5.38 (br s, 1 H), 4.21 (dd, J$_1$=6.8 Hz, J$_2$=2.148, 1 H), 4.1 (m, 1 H), 2.94 (br s, 2 H), 2.22-2.05 (m, 2 H), 1.93 (q, J=6.8, 1 H), 1.68 (m, 1 H), 1.6-1.2 (m, 7 H), 1.17 (t, J=7.6, 2 H), 0.86-0.80 (dd, J$_1$=6.8 Hz, J$_2$=9.0, 6 H).

EXAMPLE 6

Preparation of MC-Val-Cit-4-Abz-Val-Dil-Dap-Phe-OtBu (Compound 105)

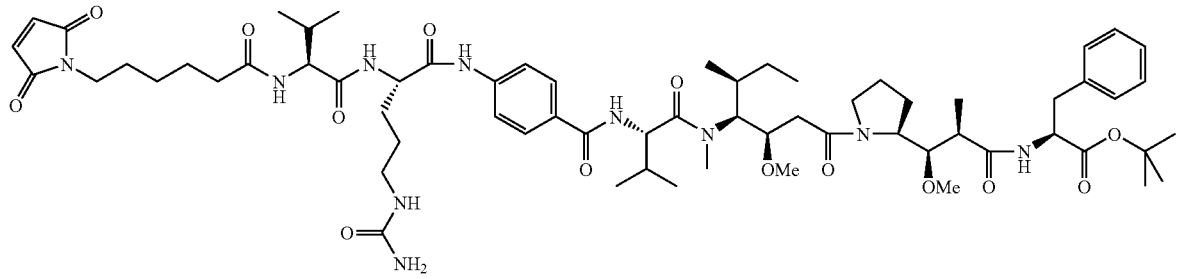

4-Abz-Val-Dil-Dap-Phe-OtBu (compound 100, 97 mg, 0.122 mmol) and MC-Val-Cit-OH (compound 104, 69 mg, 0.146 mmol) were suspended in anhydrous DMF (3 mL). HATU (70 mg, 0.183 mmol, 1.5 eq) was added followed by pyridine (0.04 mL, 0.488 mmol). After 16 h at room temperature, the reaction was not complete, so additional reagents (0.024 mmol of MC-Val-Cit-OH; and 0.024 mmol of HATU) were added and the reaction mixture was stirred for an additional 16 h. The solution was diluted with CH$_2$Cl$_2$ (60 mL) and washed with 0.1 M HCl (aq) (2×100 mL). The organic layer was concentrated in vacuo, and the crude residue was purified by radial chromatography (Chromatotron) using a 0-5-10% MeOH/CH$_2$Cl$_2$ step-gradient, resulting in 80 mg (0.064 mmol, 53% yield) of compound 105. ES-MS m/z 1243.26 [M+H]$^+$; 1265.13 [M+Na]$^+$; 1241.35 [M−H]$^−$.

EXAMPLE 7

Preparation of MC-Val-Cit-4-Abz-Val-Dil-Dap-Phe (Compound 106)

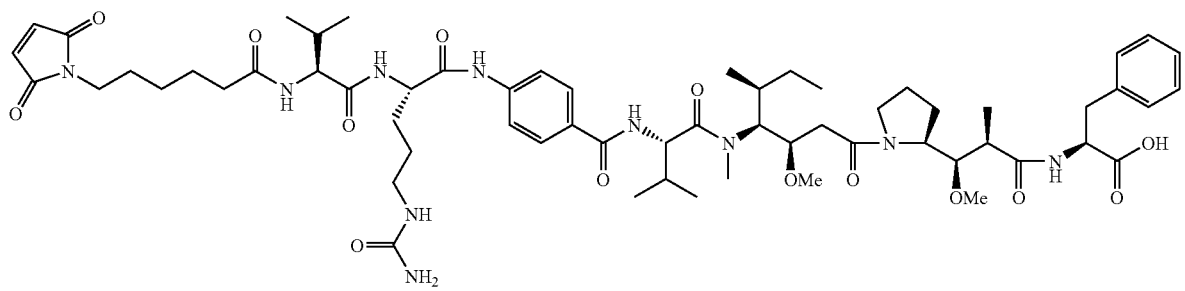

Compound 105 (80 mg, 0.064 mmol) was suspended in anhydrous $CH_2Cl_2$ (5 mL) and TFA (5 mL). This reaction mixture was stirred at room temperature for 3 h. Volatile organics were evaporated in vacuo, and product was isolated by preparatory RP-HPLC, using a Phenomenex C12 Synergi Max-RP 80A Column (250×21.20 mm). Eluent: linear gradient 10% to 90% MeCN/0.05% TFA (aq) over 8 minutes, then isocratic 90% MeCN/0.05% TFA (aq) for an additional 12 minutes. The product was obtained as a white solid (69 mg, 0.058 mmol, 91% yield). ES-MS m/z 1187.41 $[M+H]^+$; 1185.63 $[M-H]^-$.

EXAMPLE 8

Preparation of 4-Abz-Val-Dil-Dap-Phe-OMe (Compound 107)

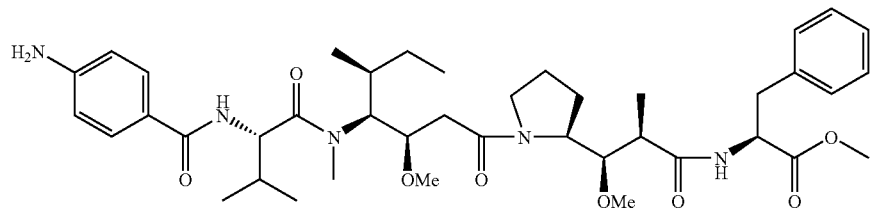

To a room temperature suspension of Boc-Dap-OH (6.31 g, 22 mmol) in anhydrous $CH_2Cl_2$ (100 mL) was added HCl× Phe-OMe (5.2 g, 24.2 mmol), DEPC (6.7 mL, 44 mmol) and DIEA (11.5 mL, 65.9 mmol). This reaction mixture was stirred for 16 h, diluted with ethyl acetate (500 mL) and washed sequentially with 0.1 M HCl (2×300 mL), $H_2O$ (300 mL), saturated $NaHCO_3$ (2×300 mL) and $H_2O$ (300 mL). The organic layer was dried over anhydrous $MgSO_4$, filtered and concentrated in vacuo. This crude oil was purified by silica gel flash column chromatography using a 20-100% ethyl acetate/hexanes gradient. Boc-Dap-Phe-OMe was obtained as white foam (8.85 g, 19.7 mmol, 90% yield).

To a suspension of Cbz-Val-Dil-OH (3.35 g, 7.68 mmol) and Boc-Dap-Phe-OMe (3.44 g, 7.68 mmol) in anhydrous $CH_2Cl_2$ (10 mL) was added TFA (10 mL). This reaction mixture was allowed to stir at room temperature for 2 h. The reaction mixture was diluted with toluene and xylenes (1:1, 50 mL) and all volatile organics were evaporated in vacuo. The crude residue was diluted in anhydrous $CH_2Cl_2$, followed by the addition of DIEA (5.35 mL, 30.7 mmol) and DEPC (1.75 mL, 11.5 mmol). This mixture was stirred at room temperature for 16 h, volatile organics were removed in vacuo, and the crude residue diluted with ethyl acetate (250 mL). This crude solution was washed sequentially with 0.1 M aq. HCl (2×300 mL), $H_2O$ (300 mL), saturated aq. $NaHCO_3$ (2×300 mL) and $H_2O$ (300 mL). The organic layer was dried over anhydrous $MgSO_4$, filtered and concentrated in vacuo. This crude oil was purified by silica gel flash column chromatography using a 20-100% ethyl acetate/hexanes gradient. Cbz-Val-Dil-Dap-Phe-OMe was obtained as lightly-yellow foam (3.5 g, 4.56 mmol, 59% yield) and used directly in the following step.

Cbz-Val-Dil-Dap-Phe-OMe (3.50 g, 4.56 mmol) was dissolved in anhydrous ethanol (100 mL) and to it was added 10% palladium/carbon (~1 g). The air in the flask was replaced with hydrogen gas, and this room temperature mixture was stirred for 16 h. The mixture was then filtered through celites (pre-washed with methanol), and concentrated in vacuo resulting in white foam (2.81 g, 4.44 mmol, 97% yield). ES-MS m/z 633.47 $[M+H]^+$.

To a suspension of Val-Dil-Dap-Phe-OMe (59 mg, 0.093 mmol) in anhydrous $CH_2Cl_2$ (2 mL) was added Boc-4-Abz-OH (24 mg, 0.103 mmol), DEPC (0.028 ml, 0.186 mmol) and DIEA (0.057 mL, 0.326 mmol). The reaction was allowed to stir for 16 h at room temperature. Product was purified by radial chromatography (Chromatotron, 0-5% gradient: MeOH/$CH_2Cl_2$). ES-MS m/z 852.56 [M+H]$^+$; 874.54 [M+Na]$^+$; 850.66 [M−H]$^−$.

Boc-4-Abz-Val-Dil-Dap-Phe-OMe was diluted in anhydrous $CH_2Cl_2$ (2 mL). 4 M HCl in dioxane (1 mL) was added, and the reaction was stirred for 3 hr. Volatile organics were evaporated in vacuo, and the residue was purified by radial chromatography (Chromatotron, 075% gradient: MeOH/$CH_2Cl_2$). 4-Abz-Val-Dil-Dap-Phe-OMe (compound 107) was isolated as a white solid (31 mg, 0.0393 mmol, 42% yield). ES-MS m/z 752.52 [M+H]$^+$; 774.49 [M+Na]$^+$; 750.63 [M−H]$^−$.

EXAMPLE 9

Preparation of MC-Val-Cit-4-Abz-Val-Dil-Dap-Phe-OMe (Compound 108)

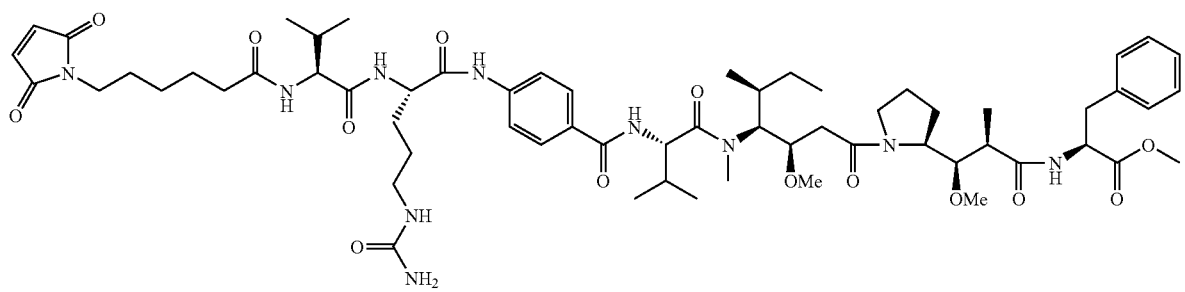

4-Abz-Val-Dil-Dap-Phe-OMe (compound 107, 31 mg, 0.039 mmol) and MC-Val-Cit-OH (18 mg, 0.039 mmol) were suspended in anhydrous DMF (0.5 mL). HATU (18 mg, 0.047 mmol, 1.2 eq) was added followed by pyridine (0.01 mL, 0.12 mmol) and DIEA (0.007 mL, 0.039 mmol). After 16 h, the reaction mixture was concentrated in vacuo, and the residue was purified first by radial chromatography (Chromatotron, 0-5-10% MeOH/$CH_2Cl_2$ step-gradient), then by preparatory RP-HPLC, using a Phenomenex $C_{12}$ Synergi Max-RP 80A Column (250×21.20 mm). Eluent: linear gradient 10% to 90% MeCN/0.05% TFA (aq) over 8 minutes, then isocratic 90% MeCN/0.05% TFA (aq) for an additional 12 minutes. MC-Val-Cit-4-Abz-Val-Dil-Dap-Phe-OMe (compound 108) was obtained as a glass-like solid (1.34 mg, 0.001 mmol, 2.8% yield). ES-MS m/z 1201.46 [M+H]$^+$; 1223.43 [M+Na]$^+$; 1199.55 [M−H]$^−$.

EXAMPLE 10

Preparation of 3-Abz-Val-Dil-Dap-Phe-OtBu (Compound 109)

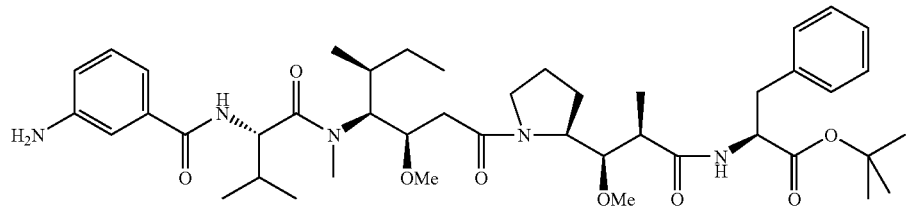

Compound 109 was prepared as described in Example 1 using Fmoc-3-Abz-OH. ES-MS m/z 794.38 [M+H]$^+$.

EXAMPLE 11

Preparation of 3-Abz-Val-Dil-Dap-Phe
(Compound 110)

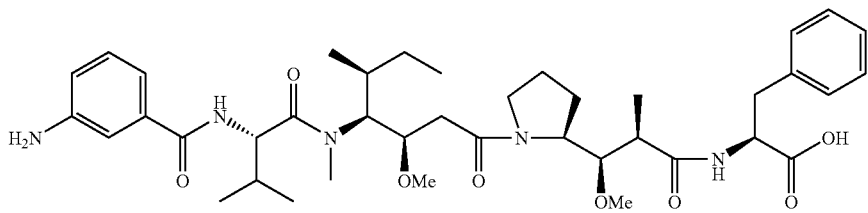

Compound 110 was prepared from Compound 109 as described in the Example 4. ES-MS m/z 738.37 $[M+H]^+$.

EXAMPLE 12

Preparation of MC-Val-Cit-4-Abz-Val-Dil-Dap-Phe
(Compound 111)

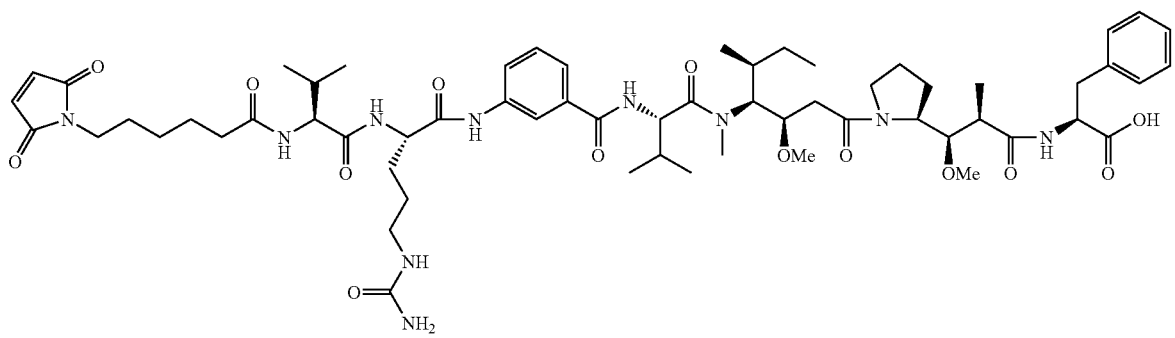

Compound III was prepared from Compound 109 according to procedures described in Examples 6 and 7. ES-MS m/z 1187.41 $[M+H]^+$.

EXAMPLE 13

In Vitro Cytotoxicity Data for Drugs

Table 6 summarizes cytotoxic activity of MMAF, 100, 103, 107 on H3396 human breast carcinoma and Karpas-299 anaplastic large cell lymphoma cell lines assayed. To evaluate the cytotoxicity of Compounds 100, 103, and 107, cells were seeded at approximately 10,000 per well in 150 µl of culture medium containing graded doses of Compounds 100, 103, and 107 in quadruplicates at the initiation of assay. Cytotoxicity assays were usually carried out for 96 hours. Fifty µl of the alamarBlue™ dye was added to each well during the last 4 to 6 hours of the incubation to assess viable cells at the end of culture. Dye reduction was determined by fluorescence spectrometry using the excitation and emission wavelengths of 535 nm and 590 nm, respectively. For analysis, the extent of alamarBlue™ reduction by the treated cells was compared to that of the untreated control cells.

The data shows that the drugs of invention have similar potency to the corresponding MMAF derivatives.

TABLE 6

| | $IC_{50}$ values (nM) | |
|---|---|---|
| Drugs | H3396 | karpas 299 |
| MMAE | 0.8 | 0.13 |
| MMAF | 104 | 130 |
| Compound 100 | 17.8 | 1.8 |
| Compound 103 | >100 | 43 |
| Compound 107 | 0.003 | 0.12 |

EXAMPLE 14

In Vitro Cytotoxicity Data for Conjugates

Table 7 shows cytotoxic effect of the cAC10 Conjugates having in average 4 drugs per antibody, assayed as described above on a CD30+ cell line Karpas 299.

TABLE 7

| Conjugates (all 4 drugs/Ab) | IC50 (ng/mL) |
|---|---|
| cAC10-vc-MMAF | 0.75 |
| cAC10-102 | 1.0 |
| cAC10-106 | 1.3 |
| cAC10-108 | 2.5 |

EXAMPLE 15

Mouse Toxicity Data for cAC10-108 Conjugate

FIG. 1 shows toxicity of cAC10-108 conjugate in mice. Groups of mice (3/group) were treated with 100 mg/kg antibody component of cAC10-Val-Cit-PABC-MMAF and cAC10-108 having an average 4 drugs per antibody. As shown in the Figure, cAC10-108 exhibits little toxicity in mice.

EXAMPLE 16

In Vivo Efficacy Data for cAC10-108 Conjugate

Figure 2:
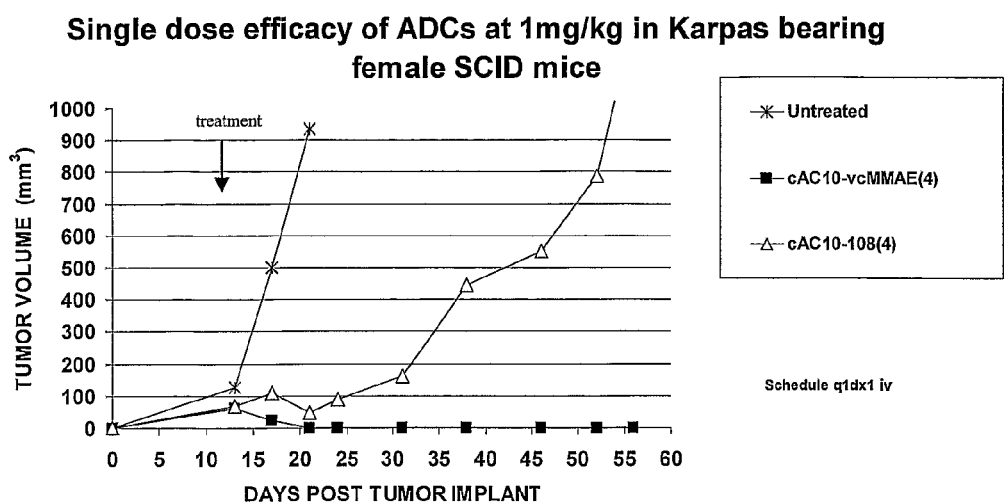
FIG. 2 shows efficacy of the cAC10 conjugates having an average of 4 drugs per antibody in SCID mice.

FIG. 2 shows efficacy of the cAC10 conjugates having an average 4 drugs per antibody in SCID mice. Groups of mice (4/group) with subcutaneous Karpas 299 human ALCL tumors (cAC10 Ag$^+$) of approximately 100 mm$^3$ average in size were treated with cAC10-Val-Cit-PABC-MMAE or cAC10-108 at 1 mg/kg of antibody component. As shown in the Figure, treatment with cAC10-108 reduces tumor size, as compared with the untreated controls.

No license is expressly or implicitly granted to any patent or patent applications referred to or incorporated herein. The discussion above is descriptive, illustrative and exemplary and is not to be taken as limiting the scope defined by any appended claims.

Various references, including patent applications, patents, and scientific publications, are cited herein, the disclosures of each of which is incorporated herein by reference in its entirety.

The invention claimed is:

1. A Conjugate Compound having the Formula Ia:

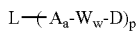

or a pharmaceutically acceptable salt thereof;
wherein:
L- is a Ligand Unit;
-A$_a$-W$_w$— is a Linker Unit (LU), wherein:
-A- is a Stretcher Unit,
a is 0 or 1,
each —W— is independently an Amino Acid Unit,
w is an integer ranging from 0 to 12,
p is an integer ranging from 1 to about 20; and
-D is a Drug Unit of the formula

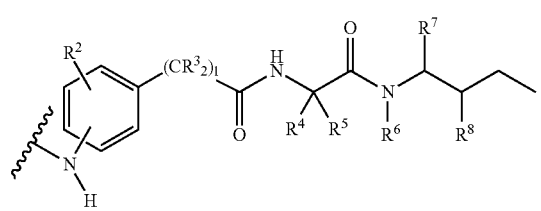

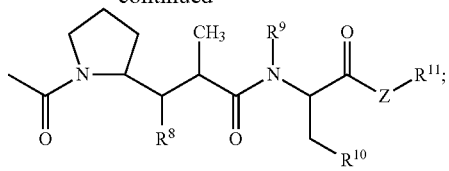

wherein independently at each location:

R$^2$ is selected from the group consisting of -hydrogen, —C$_1$-C$_8$ alkyl, —O—(C$_1$-C$_8$ alkyl), -halogen, —NO$_2$, —COOH, and —C(O)OR$^{11}$;

each R$^3$ is selected independently from the group consisting of -hydrogen and —C$_1$-C$_8$alkyl;

I is an integer ranging from 0-10;

R$^4$ is selected from the group consisting of -hydrogen, —C$_1$-C$_8$ alkyl, —C$_3$-C$_8$ carbocycle, -aryl, —C$_1$-C$_8$ alkyl-aryl, —C$_1$-C$_8$ alkyl-(C$_3$-C$_8$ carbocycle), —C$_3$-C$_8$ heterocycle and —C$_1$-C$_8$ alkyl-(C$_3$-C$_8$ heterocycle); and R$^5$ is selected from the group consisting of —H and -methyl; or R$^4$ and R$^5$ jointly have the formula —(CR$^a$R$^b$)$_n$—, wherein R$^a$ and R$^b$ are independently selected from the group consisting of —H, —C$_1$-C$_8$ alkyl and —C$_3$-C$_8$ carbocycle, n is selected from the group consisting of 2, 3, 4, 5 and 6, and form a ring with the carbon atom to which they are attached;

R$^6$ is selected from the group consisting of —H and —C$_1$-C$_8$ alkyl;

R$^7$ is selected from the group consisting of —H, —C$_1$-C$_8$ alkyl, —C$_3$-C$_8$ carbocycle, aryl, —C$_1$-C$_8$ alkyl-aryl, —C$_1$-C$_8$ alkyl-(C$_3$-C$_8$carbocycle), —C$_3$-C$_8$ heterocycle and —C$_1$-C$_8$ alkyl-(C$_3$-C$_8$ heterocycle);

each R$^8$ is independently selected from the group consisting of —H, —OH, —C$_1$-C$_8$ alkyl, —C$_3$-C$_8$ carbocycle, —O-alkyl-(C$_1$-C$_8$ carbocycle) and —O—(C$_1$-C$_8$ alkyl);

R$^9$ is selected from the group consisting of —H and —C$_1$-C$_8$ alkyl;

R$^{10}$ is selected from the group consisting of aryl group and —C$_3$-C$_8$ heterocycle;

Z is selected from the group consisting of —O—, —S—, —NH—, and —NR$^{12}$— where R$^{12}$ is C$_1$-C$_8$ alkyl or aryl; and R$^{11}$ is selected from the group consisting of —H, C$_1$-C$_8$ alkyl, aryl, —C$_3$-C$_8$ heterocycle, —(CH$_2$CH$_2$O)$_r$—H, —(CH$_2$CH$_2$O)$_r$—CH$_3$, and —(CH$_2$CH$_2$O)$_r$—CH$_2$CH$_2$C(O)OH;

wherein r is an integer ranging from 1-10.

2. The Conjugate Compound of claim 1 or a pharmaceutically acceptable salt thereof, wherein the Linker Unit has the general Formula Ib:

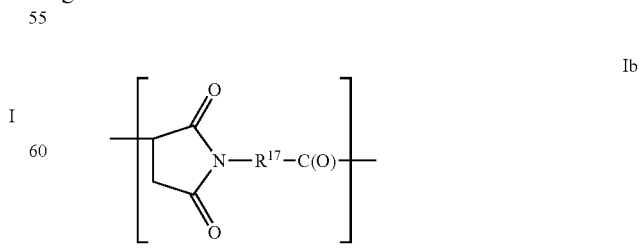

wherein R$^{17}$ is selected from the group consisting of —C$_1$-C$_{10}$ alkylene-, —C$_3$-C$_8$ carbocyclo-, —O—(C$_1$-C$_8$ alkyl)-, -arylene-, —C₁-C₁₀ alkylene-arylene-, -arylene—C₁-C₁₀ alkylene-, —C₁-C₁₀ alkylene-(C₃-C₈ carbocyclo)-, -(C₁-C₈ carbocyclo)—C₁-C₁₀ alkylene-, —C₃-C₈ heterocyclo-, —C₁-C₈ alkylene-(C₃-C₈ heterocyclo)-, —(C₃-C₈ heterocyclo)—C₁-C₁₀ alkylene-, —(CH₂CH₂O)$_r$—, and —(CH₂CH₂O)$_r$—CH₂—; and r is an integer ranging from 1-100.

3. The Conjugate Compound of claim 1 or a pharmaceutically acceptable salt thereof, wherein the Drug Unit has the following formula:

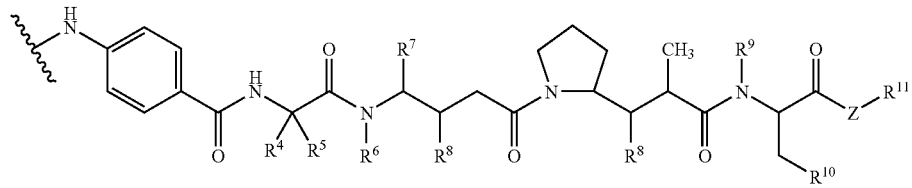

I wherein independently at each location:

R⁴ is selected from the group consisting of -hydrogen, —C₁-C₈ alkyl, —C₃-C₈ carbocycle, -aryl, —C₁-C₈ alkyl-aryl, —C₁-C₈ alkyl-(C₃-C₈ carbocycle), —C₃-C₈ heterocycle and —C₁-C₈ alkyl-(C₃-C₈ heterocycle); and R⁵ is selected from the group consisting of —H and -methyl; or R⁴ and R⁵ jointly have the formula —(CR$^a$R$^b$)$_n$—, wherein R$^a$ and R$^b$ are independently selected from the group consisting of —H, —C₁-C₈ alkyl and —C₃-C₈ carbocycle, n is selected from the group consisting of 2, 3, 4, 5 and 6, and form a ring with the carbon atom to which they are attached;

R⁶ is selected from the group consisting of —H and —C₁-C₈ alkyl;

R⁷ is selected from the group consisting of —H, —C₁-C₈ alkyl, —C₃-C₈ carbocycle, aryl, —C₁-C₈ alkyl-aryl, —C₁-C₈ alkyl-(C₃-C₈ carbocycle), —C₃-C₈ heterocycle and —C₁-C₈ alkyl-(C₃-C₈ heterocycle);

each R⁸ is independently selected from the group consisting of —H, —OH, —C₁-C₈ alkyl, —C₃-C₈ carbocycle, —O-alkyl-(C₁-C₈ carbocycle) and —O—(C₁-C₈ alkyl);

R⁹ is selected from the group consisting of —H and —C₁-C₈ alkyl;

R¹⁹ is selected from the group consisting of aryl group and —C₃-C₈ heterocycle;

Z is selected from the group consisting of —O—, —S—, —NH—, and —NR¹²— where R¹² is C₁-C₈ alkyl or aryl; and R¹¹ is selected from the group consisting of —H, C₁-C₈ alkyl, aryl, —C₃-C₈ heterocycle, —(CH₂CH₂O)$_r$—H, —(CH₂CH₂O)$_r$—CH₃, and —(CH₂CH₂O)$_r$—CH₂CH₂C(O)OH;

wherein r is an integer ranging from 1-10.

4. The Conjugate Compound of claim 3 or a pharmaceutically acceptable salt thereof, wherein the Drug Unit has the following formula:

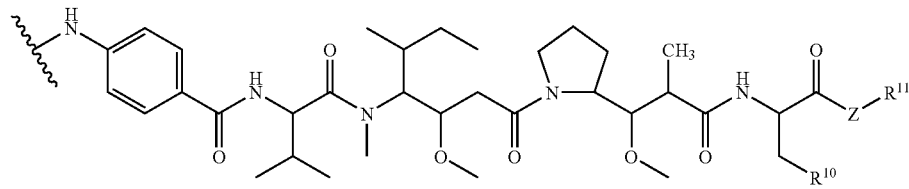

wherein independently as each location:
R$^{10}$ is selected from the group consisting of aryl group and —C$_3$-C$_8$ heterocycle;
Z is selected from the group consisting of —O—, —S—, —NH—, and —NR$^{12}$—where R$^{12}$ is C$_1$-C$_8$ alkyl or aryl; and
R$^{11}$ is selected from the group consisting of —H, C$_1$-C$_8$ alkyl, aryl, —C$_3$-C$_8$ heterocycle, —(CH$_2$CH$_2$O)$_r$—H, —(CH$_2$CH$_2$O)$_r$—CH$_3$, and —(CH$_2$CH$_2$O)$_r$—CH$_2$CH$_2$C(O)OH;
wherein r is an integer ranging from 1-10.

5. The Conjugate Compound of claim 4 or a pharmaceutically acceptable salt thereof, wherein the Drug Unit has the following formula:

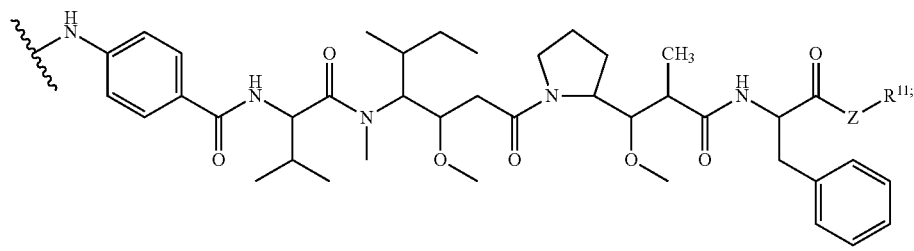

wherein Z is selected from the group consisting of —O—, —S—, —NH—, and —NR$^{12}$—; where R$^{12}$ is C$_1$-C$_8$ alkyl or aryl; and
R$^{11}$ is selected from the group consisting of —H, C$_1$-C$_8$ alkyl, aryl, —C$_3$-C$_8$ heterocycle, —(CH$_2$CH$_2$O)$_r$—H, —(CH$_2$CH$_2$O)$_r$—CH$_3$, and —(CH$_2$CH$_2$O)$_r$—CH$_2$CH$_2$C(O)OH;
wherein r is an integer ranging from 1-10.

6. The Conjugate Compound of claim 5 or a pharmaceutically acceptable salt thereof, wherein the Drug Unit has the following formula:

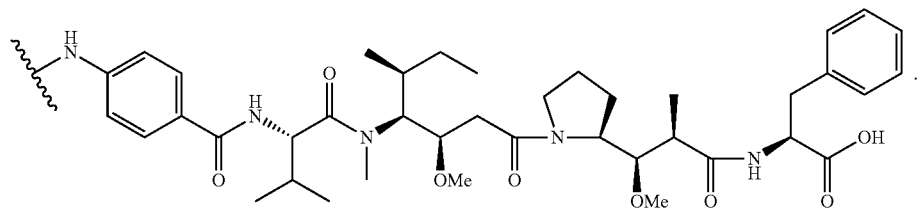

7. The Conjugate Compound of claim 1 or a pharmaceutically acceptable salt thereof, wherein the Ligand Unit is an antibody that binds to an antigen.

8. The Conjugate Compound of claim 7 or a pharmaceutically acceptable salt thereof, wherein the antibody a chimeric antibody, a humanized antibody, or a functionally active fragment thereof.

9. The Conjugate Compound of claim 7 or a pharmaceutically acceptable salt thereof, wherein the antibody is attached to the Linker Unit through a cysteine residue of the antibody.

10. The Conjugate Compound of claim 7 or a pharmaceutically acceptable salt thereof, wherein p is 2 to 8.

11. The Conjugate Compound of claim 10 or a pharmaceutically acceptable salt thereof, wherein p is 4.

12. The Conjugate Compound of claim 7, having the formula:

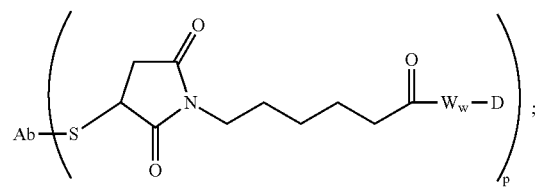

or a pharmaceutically acceptable salt thereof, wherein Ab is an antibody, and S is a sulfur atom of the antibody.

13. The Conjugate Compound of claim 7 or a pharmaceutically acceptable salt thereof, having the formula:

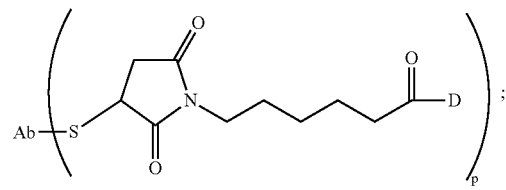

wherein Ab is an antibody, and S is a sulfur atom of the antibody.

14. The Conjugate Compound of claim 7, having the formula:

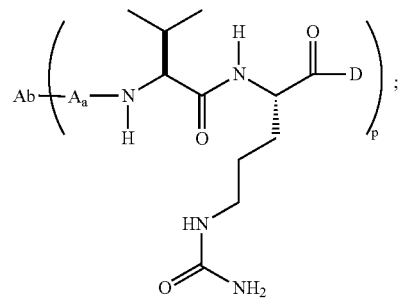

or a pharmaceutically acceptable salt thereof, wherein Ab is an antibody, and S is a sulfur atom of the antibody.

15. The Conjugate Compound of claim 14 having the formula:

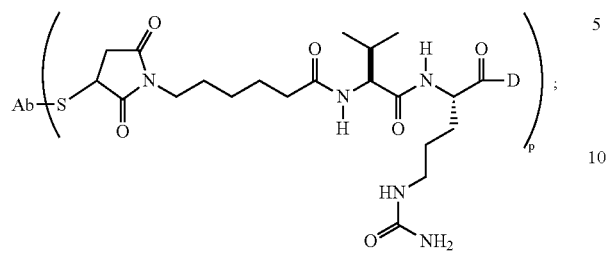

or a pharmaceutically acceptable salt thereof, wherein Ab is an antibody, and S is a sulfur atom of the antibody.

16. The Conjugate Compound of claim 7, wherein a Drug Linker Unit of the following formula or a pharmaceutically acceptable salt thereof is conjugated to the antibody:

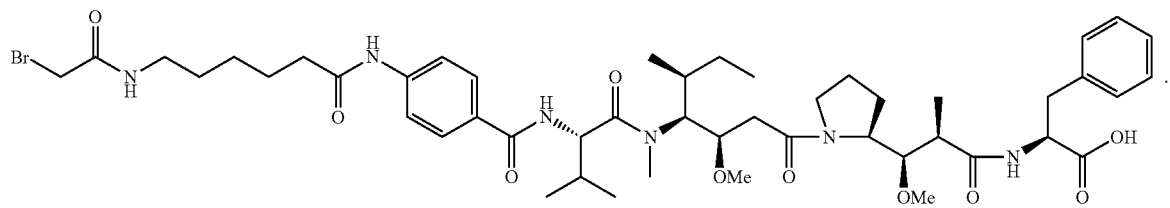

17. The Conjugate Compound of claim 7, wherein a Drug Linker Unit of the following formula or a pharmaceutically acceptable salt thereof is conjugated to the antibody:

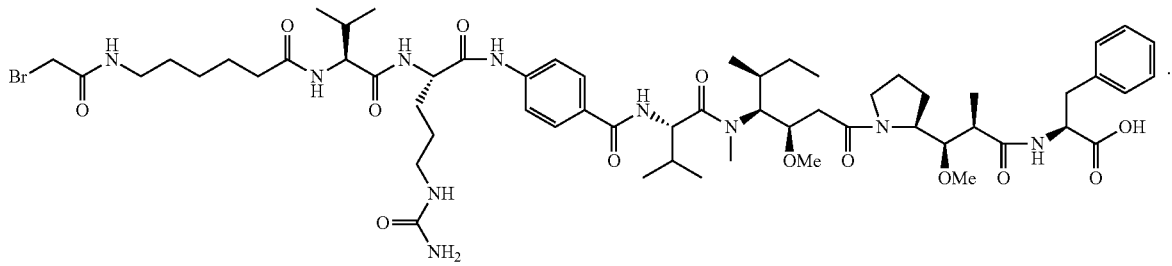

18. A pharmaceutical composition, comprising
a Conjugate Compound of claim 1 or a pharmaceutically acceptable salt thereof;
a container; and
a package insert or label indicating that the compound can be used to treat cancer.

19. A Drug Compound having the Formula I:

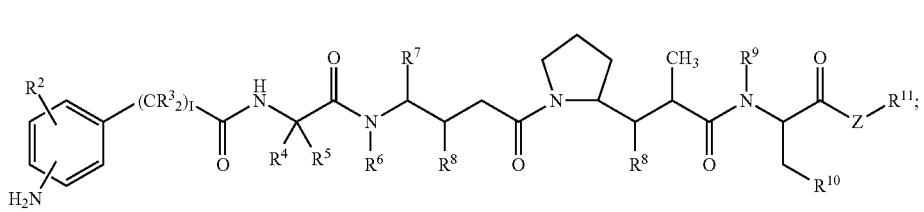

or a pharmaceutically acceptable salt or solvate thereof; wherein, independently at each location:

$R^2$ is selected from the group consisting of -hydrogen —$C_1$-$C_8$ alkyl, —O—($C_1$-$C_8$ alkyl), -halogen, —$NO_2$, —COOH, and —C(O)OR";

each $R^3$ is selected independently from the group consisting of -hydrogen and —$C_1$-$C_8$ alkyl;

I is an integer ranging from 0-10;

$R^4$ is selected from the group consisting of -hydrogen, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_1$-$C_8$ heterocycle);

$R^5$ is selected from the group consisting of —H and -methyl; or $R^4$ and $R^5$ jointly have the formula —$(CR^a R^b)_n$—, wherein $R^a$ and $R^b$ are independently selected from the group consisting of —H, —$C_1$-$C_8$ alkyl and —$C_3$-$C_8$ carbocycle and n is selected from the group consisting of 2, 3, 4, 5 and 6, and form a ring with the carbon atom to which they are attached;

$R^6$ is selected from the group consisting of —H and —$C_1$-$C_8$ alkyl;

$R^7$ is selected from the group consisting of —H, —$C_1$-$C_8$ alkyl, —$C_3$-$C_8$ carbocycle, aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from the group consisting of —H, —OH, —$C_1$-$C_8$ alkyl, —$C_3$-$C_8$ carbocycle, —O-alkyl-($C_1$-$C_8$ carbocycle) and —O—($C_1$-$C_8$ alkyl);

$R^9$ is selected from the group consisting of —H and —$C_1$-$C_8$ alkyl;

$R^{10}$ is selected from the group consisting of aryl group and —$C_3$-$C_8$ heterocycle;

Z is selected from the group consisting of —O—, —S—, —NH—, and —$NR^{12}$—where $R^{12}$ is $C_1$-$C_8$ alkyl; or aryl; and $R^{11}$ is selected from the group consisting of —H, $C_1$-$C_8$ alkyl, aryl, —$C_3$-$C_8$ heterocycle, —$(CH_2CH_2O)_r$—H, —$(CH_2CH_2O)_r$—$CH_3$, and —$(CH_2CH_2O)_r$—$CH_2CH_2C(O)OH$;

wherein r is an integer ranging from 1-10.

20. The Drug Compound of claim 19 having the following formula:

or a pharmaceutically acceptable salt thereof; wherein independently at each location:

$R^4$ is selected from the group consisting of -hydrogen, —$C_1$-$C_8$ alkyl, —$C_3$-$C_8$ carbocycle, -aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

$R^5$ is selected from the group consisting of —H and -methyl; or $R^4$ and $R^5$ jointly have the formula —$(CR^a R^b)_n$—, wherein $R^a$ and $R^b$ are independently selected from the group consisting of —H, —$C_1$-$C_8$ alkyl and —$C_3$-$C_8$ carbocycle, n is selected from the group consisting of 2, 3, 4, 5 and 6, and form a ring with the carbon atom to which they are attached;

$R^6$ is selected from the group consisting of —H and —$C_1$-$C_8$ alkyl;

$R^7$ is selected from the group consisting of —H, —$C_1$-$C_8$ alkyl, —$C_3$-$C_8$ carbocycle, aryl, —$C_1$-$C_8$ alkyl-aryl, —$C_1$-$C_8$ alkyl-($C_3$-$C_8$ carbocycle), —$C_3$-$C_8$ heterocycle and —$C_1$-$C_8$ alkyl-($C_3$-$C_8$ heterocycle);

each $R^8$ is independently selected from the group consisting of —H, —OH, —$C_1$-$C_8$ alkyl, —$C_3$-$C_8$ carbocycle, —O-alkyl-($C_1$-$C_8$ carbocycle) and —O—($C_1$-$C_8$ alkyl);

$R^9$ is selected from the group consisting of —H and —$C_1$-$C_8$ alkyl;

$R^{10}$ is selected from the group consisting of aryl group and —$C_3$-$C_8$ heterocycle;

Z is selected from the group consisting of —O—, —S—, —NH—, and —$NR^{12}$—where $R^{12}$ is $C_1$-$C_8$ alkyl or aryl; and $R^{11}$ is selected from the group consisting of —H, $C_1$-$C_8$ alkyl, aryl, —$C_3$-$C_8$ heterocycle, —$(CH_2CH_2O)_r$—H, —$(CH_2CH_2O)_r$—$CH_3$, and —$(CH_2CH_2O)_r$—$CH_2CH_2C(O)OH$;

wherein r is an integer ranging from 1-10.

21. The Drug Compound of claim 20 having the following formula:

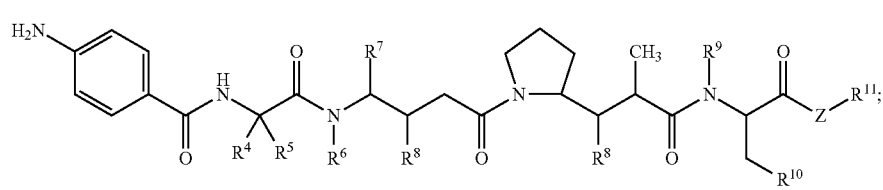

I

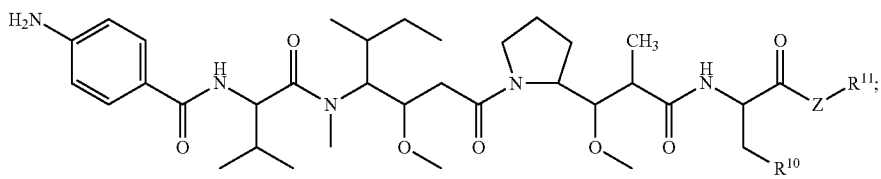

or a pharmaceutically acceptable salt thereof; wherein independently as each location:
$R^{10}$ is selected from the group consisting of aryl group and —$C_3$-$C_8$ heterocycle;
Z is selected from the group consisting of —O—, —S—, —NH—, and —$NR^{12}$— where $R^{12}$ is $C_1$-$C_8$ alkyl or aryl; and
$R^{11}$ is selected from the group consisting of —H, $C_1$-$C_8$ alkyl, aryl, —$C_3$-$C_8$ heterocycle, —($CH_2CH_2O)_r$—H, —($CH_2CH_2O)_r$—$CH_3$, and —($CH_2CH_2O)_r$—$CH_2CH_2C(O)OH$;
wherein r is an integer ranging from 1-10.

22. The Drug Compound of claim 21 having the following formula:

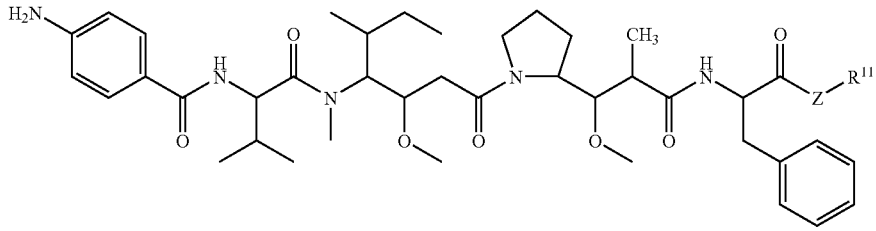

or a pharmaceutically acceptable salt thereof; wherein Z is selected from the group consisting of —O—, —S—, —NH—, and —$NR^{12}$—; where $R^{12}$ is $C_1$-$C_8$ alkyl and aryl; and
$R^{11}$ is selected from the group consisting of —H, $C_1$-$C_8$ alkyl, aryl, —$C_3$-$C_8$ heterocycle, —($CH_2CH_2O)_r$—H, —($CH_2CH_2O)_r$—$CH_3$, and —($CH_2CH_2O)_r$—$CH_2CH_2C(O)OH$;
wherein r is an integer ranging from 1-10.

23. The Drug Compound of claim 22 having the following formula:

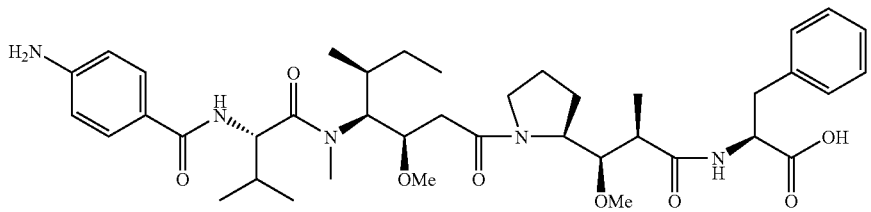

or a pharmaceutically acceptable salt thereof.

24. A Linker Drug Conjugate having the following formula:

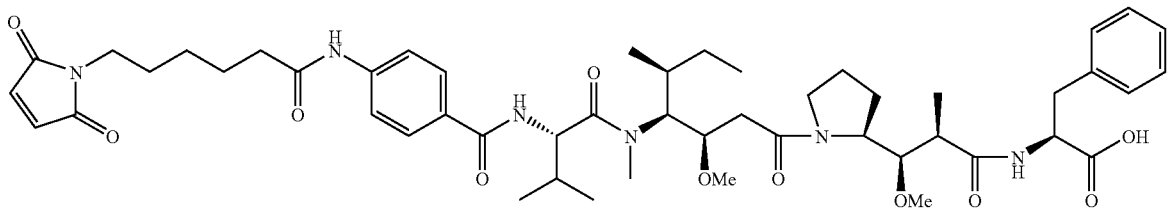

or a pharmaceutically acceptable salt thereof.

25. A Linker Drug Conjugate having the following formula:

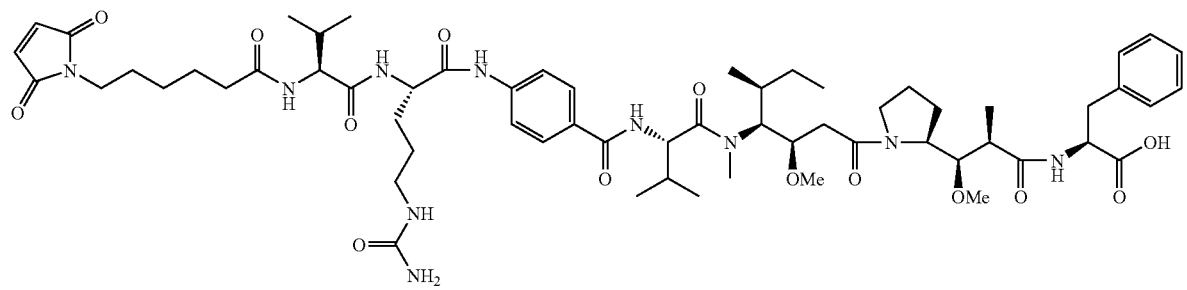

or a pharmaceutically acceptable salt thereof.

26. A Linker Drug Conjugate having the following formula:

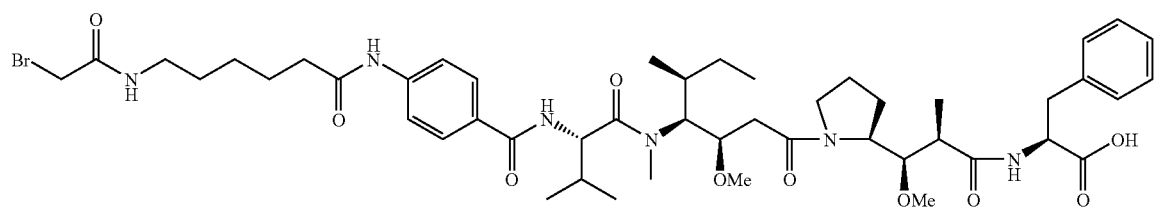

or a pharmaceutically acceptable salt thereof.

27. A Linker Drug Conjugate having the following formula:

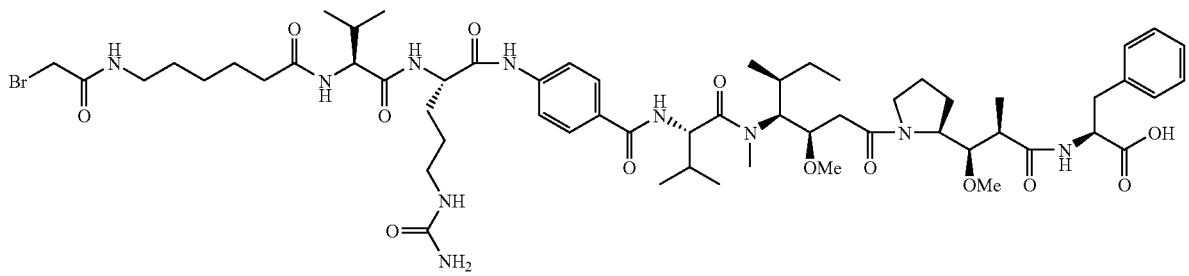

or a pharmaceutically acceptable salt thereof.

28. A Conjugate Compound of claim 15, having the following formula:

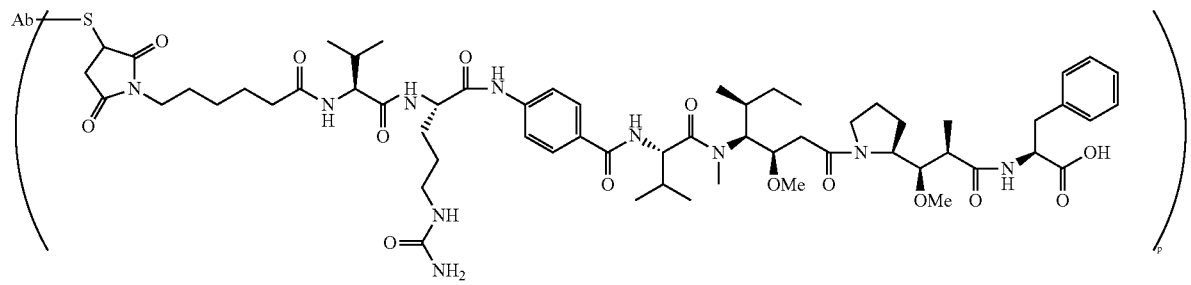

or a pharmaceutically acceptable salt thereof.

* * * * *

UNITED STATES PATENT AND TRADEMARK OFFICE
CERTIFICATE OF CORRECTION

PATENT NO. : 8,288,352 B2
APPLICATION NO. : 11/667437
DATED : October 16, 2012
INVENTOR(S) : Svetlana O. Doronina et al.

Page 1 of 1

It is certified that error appears in the above-identified patent and that said Letters Patent is hereby corrected as shown below:

In the Claims:

Claim 3, Column 82, Line 43, please delete "$^{19}$" and insert --$^{10}$--

Claim 19, Column 87, Line 1, please delete "or solvate"

Signed and Sealed this
Twenty-second Day of January, 2013

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,288,352 B2 | Page 1 of 1 |
| APPLICATION NO. | : 11/667437 | |
| DATED | : October 16, 2012 | |
| INVENTOR(S) | : Doronina et al. | |

It is certified that error appears in the above-identified patent and that said Letters Patent is hereby corrected as shown below:

In the Claims:

Claim 3, Column 82, Line 6: after the chemical structure, please insert a --;--.

Claim 4, Column 82, Line 58: after the chemical structure, please insert a --;--.

Claim 8, Column 84, Line 55: after "antibody" please insert --is--.

Claim 22, Column 89, Line 23: after the chemical structure, please insert a --;--.

Claim 23, Column 89, Line 43: after the chemical structure, please insert a --;--.

Claim 24, Column 89, Line 48: after the chemical structure, please insert a --;--.

Claim 25, Column 91, Line 48: after the chemical structure, please insert a --;--.

Claim 26, Column 91, Line 29: after the chemical structure, please insert a --;--.

Claim 27, Column 91, Line 34: after the chemical structure, please insert a --;--.

Claim 28, Column 91, Line 40: after the chemical structure, please insert a --;--.

Signed and Sealed this
Twenty-sixth Day of February, 2013

Teresa Stanek Rea
*Acting Director of the United States Patent and Trademark Office*